(12) United States Patent
Gang et al.

(10) Patent No.: US 9,381,063 B2
(45) Date of Patent: Jul. 5, 2016

(54) METHOD AND APPARATUS FOR MAGNETICALLY GUIDED CATHETER FOR RENAL DENERVATION EMPLOYING MOSFET SENSOR ARRAY

(75) Inventors: Eli Gang, Los Angeles, CA (US);
Yehoshua Josh Shachar, Santa Monica, CA (US)

(73) Assignee: Magnetecs Inc., Inglewood, CA (US)

( * ) Notice: Subject to any disclaimer, the term of this patent is extended or adjusted under 35 U.S.C. 154(b) by 818 days.

(21) Appl. No.: 13/549,341

(22) Filed: Jul. 13, 2012

(65) Prior Publication Data
US 2014/0018792 A1 Jan. 16, 2014

(51) Int. Cl.
*A61B 18/04* (2006.01)
*A61B 18/14* (2006.01)
*A61B 5/05* (2006.01)
*A61B 18/00* (2006.01)

(52) U.S. Cl.
CPC ............. *A61B 18/1492* (2013.01); *A61B 34/73* (2016.02); *A61B 5/05* (2013.01); *A61B 18/04* (2013.01); *A61B 2018/00404* (2013.01); *A61B 2018/00434* (2013.01); *A61B 2018/00511* (2013.01); *A61B 2018/00577* (2013.01); *A61B 2018/00839* (2013.01)

(58) Field of Classification Search
CPC ........... A61N 1/00; A61N 1/18; A61N 1/375; A61N 2/00; A61N 5/00; A61B 5/00; A61B 6/00; A61M 25/0133
See application file for complete search history.

(56) References Cited

U.S. PATENT DOCUMENTS

| | | | |
|---|---|---|---|
| 7,280,863 B2 | 10/2007 | Shachar |
| 7,617,005 B2 | 11/2009 | Demarais |
| 7,620,451 B2 | 11/2009 | Demarais |
| 7,647,115 B2 | 1/2010 | Levin |
| 7,653,438 B2 | 1/2010 | Deem |
| 7,769,427 B2 | 8/2010 | Shachar |
| 7,869,854 B2 | 1/2011 | Shachar |
| 7,937,143 B2 | 5/2011 | Demarais |
| 2006/0114088 A1 | 6/2006 | Shachar |
| 2006/0116633 A1 | 6/2006 | Shachar |
| 2006/0116634 A1 | 6/2006 | Shachar |
| 2006/0142801 A1 | 6/2006 | Demarais |
| 2006/0206150 A1 | 9/2006 | Demarais |
| 2006/0212078 A1 | 9/2006 | Demarais |
| 2006/0265014 A1 | 11/2006 | Demarais |
| 2006/0276852 A1 | 12/2006 | Demarais |
| 2007/0016006 A1 | 1/2007 | Shachar |
| 2007/0129720 A1 | 6/2007 | Demarais |
| 2007/0197891 A1 | 8/2007 | Shachar |
| 2007/0265687 A1 | 11/2007 | Deem |

(Continued)

*Primary Examiner* — Christopher D Koharski
*Assistant Examiner* — Elizabeth K So
(74) *Attorney, Agent, or Firm* — Marcus C. Dawes; Daniel L. Dawes

(57) ABSTRACT

A system for a mapping and ablation catheter. The catheter includes a MOSFET sensor array that provides better fidelity of the signal measurements as well as data collection and reduces the error generated by spatial distribution of the isotropic and anisotropic wave fronts and error associated with near and far field's signal averages. The system maps the change in bioelectric potential in the vicinity of an activation wave front. During measurement, the manifold carrying the sensor array translates and rotates so as to achieve a measure of high potential employing an impedance value. The system of guiding and controlling the movement of the catheter distal end is able to deliver energy for ablating the renal artery nerve and thereby providing a safe and efficient method and apparatus for neuromodulation.

20 Claims, 25 Drawing Sheets

(56) References Cited

U.S. PATENT DOCUMENTS

| | | |
|---|---|---|
| 2007/0293896 A1 | 12/2007 | Haefner |
| 2008/0027313 A1 | 1/2008 | Shachar |
| 2008/0213331 A1 | 9/2008 | Gelfand |
| 2008/0249395 A1 | 10/2008 | Shachar |
| 2008/0255642 A1 | 10/2008 | Zarins |
| 2009/0036948 A1 | 2/2009 | Levin |
| 2009/0076409 A1 | 3/2009 | Wu |
| 2009/0248014 A1 | 10/2009 | Shachar |
| 2009/0253985 A1 | 10/2009 | Shachar |
| 2009/0275828 A1 | 11/2009 | Shachar |
| 2010/0130854 A1 | 5/2010 | Shachar |
| 2010/0145179 A1 | 6/2010 | Lin |
| 2010/0160737 A1* | 6/2010 | Shachar et al. ............... 600/202 |
| 2010/0168739 A1 | 7/2010 | Wu |
| 2010/0174282 A1 | 7/2010 | Demarais |
| 2010/0191112 A1 | 7/2010 | Demarais |
| 2010/0222854 A1 | 9/2010 | Demarais |
| 2010/0249773 A1 | 9/2010 | Clark |
| 2011/0137200 A1 | 6/2011 | Yin |
| 2011/0200171 A1 | 8/2011 | Beetel |
| 2011/0257564 A1 | 10/2011 | Demarais |
| 2011/0264011 A1 | 10/2011 | Wu |
| 2011/0264075 A1 | 10/2011 | Leung |

* cited by examiner

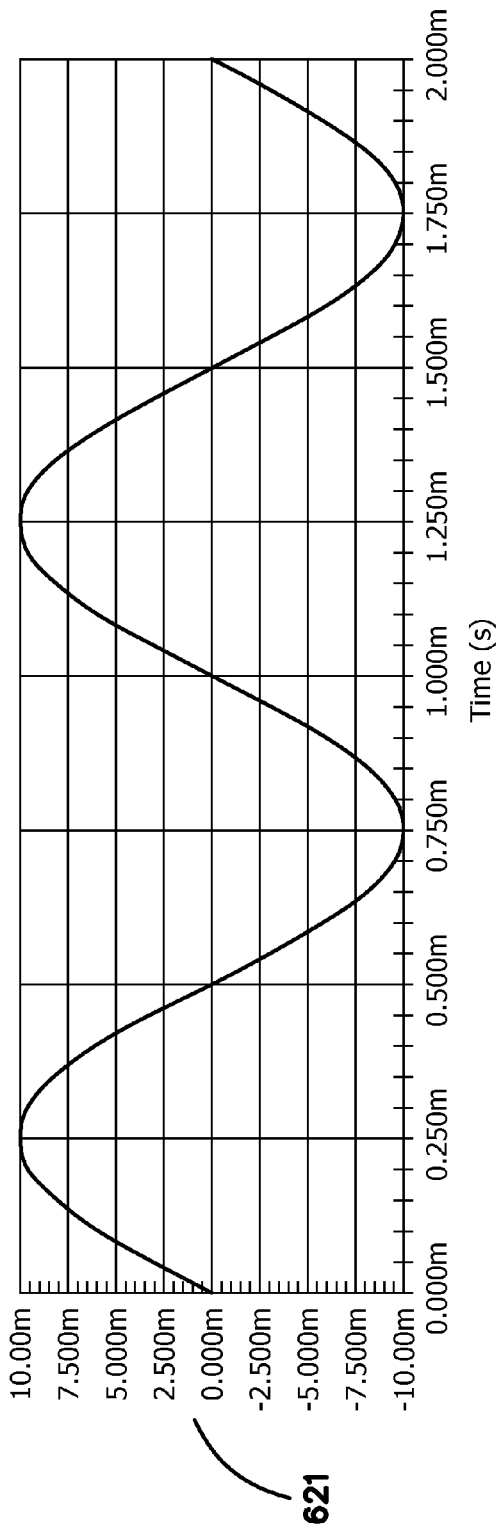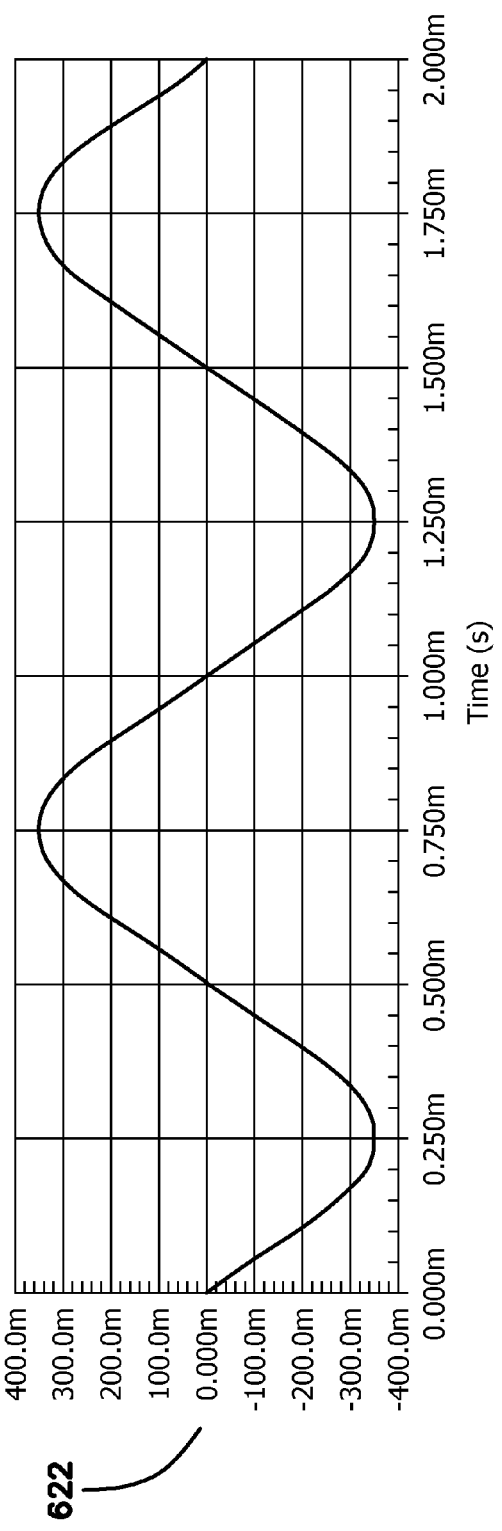
FIG. 1C

A. EEG NORMAL
B. EEG NORMAL
C. EPILEPSY
D. UNCONSCIOUSNESS
E. EEG ISCHEMIA STATE
F. EEG RETRACTOR OVER PRESSURE

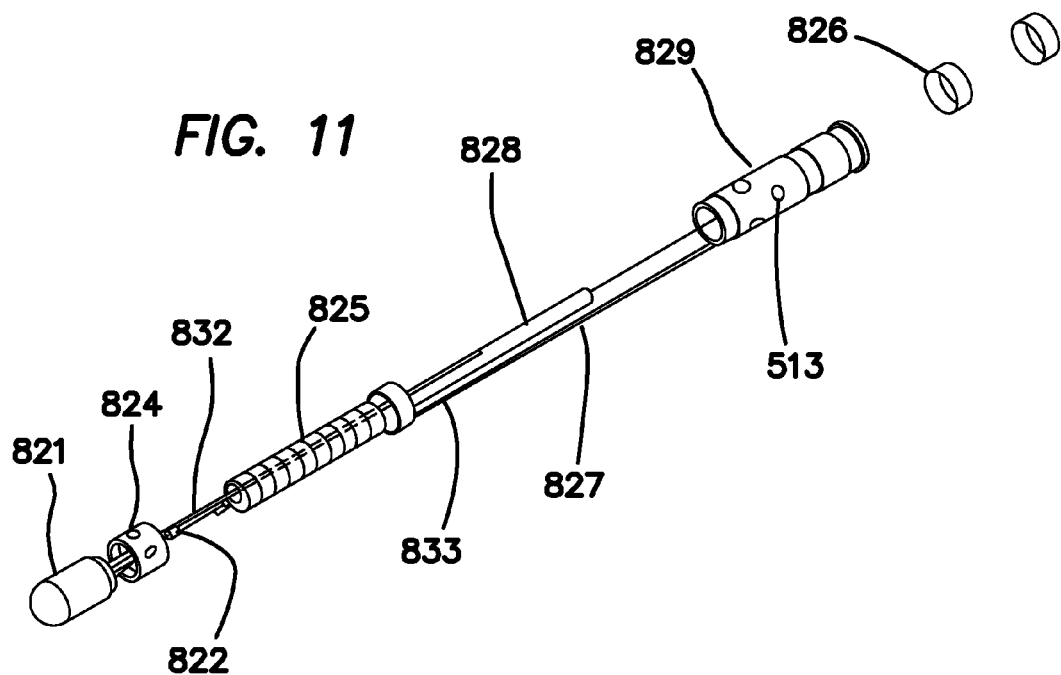

ADV=w1*TTV+w2*TPV/Rm(d)

METHOD AND APPARATUS FOR MAGNETICALLY GUIDED CATHETER FOR RENAL DENERVATION EMPLOYING MOSFET SENSOR ARRAY

RELATED APPLICATIONS

The present application is related to U.S. Pat. No. 7,869,854, filed on Feb. 23, 2006, and U.S. Pat. No. 7,769,427, filed on Jul. 15, 2003, which both are incorporated herein by reference in their entirety and which disclose the MOSFET module referenced below.

BACKGROUND

1. Field of the Technology

The disclosure generally relates to the field of magnetically guided catheters. Specifically, to a mapping and ablation catheter having an embedded MOSFET sensor array for detecting local electrophysiological parameters such as biopotential signals and tissue contact pressure within an arterial structure and more specifically in the renal artery plexus, and further for providing a means to remotely guide, control, and deliver the catheter fitted with a magnetic element. The apparatus with its sensor array and the means for guiding and controlling the movement of the device is described in connection with the current clinical method of neuro-modulation so as to normalize a patient's blood pressure.

2. Description of the Prior Art

Clinical Observation on Renal Denervation Procedure

It has long been known that the kidneys play an important role in the genesis and maintenance of hypertension (HTN). The seminal studies of Goldblatt in 1934 showed that reduction of blood flow to a kidney can cause severe hypertension, now known to be the result of activation of the renin-angiotensin-aldosterone system (RAS). The RAS peptide chain-reaction that results in HTN can be reversed by restoring blood flow to the affected kidney in this model of vascular disease of the kidneys.

The kidney's role in hypertension is not only restricted to instances of decreased blood flow. It is known that the kidney has a rich innervation by sympathetic efferent nerve terminals and by a rich network of afferent (sensory) nerve endings. The efferent nerve endings cause renal vascular constriction, stimulate renin release and also enhance sodium and water retention, all of which lead to HTN. The afferent nerve endings appear to signal the brain of changes in the chemical composition of blood and urine and mechanical changes in the renal pelvis. These signals appear to evoke sympathetic excitation, resulting in activation of the sympathetic efferent nerves and resultant HTN. Renal nerves have also been implicated in the progression of chronic kidney disease associated with chronic hypertension. Of great importance to the concept of renal artery denervation, the renal artery is the site of many of the afferent and efferent nerve endings.

Based on the above physiology, surgeons first began in the 1930s to attempt to disconnect the autonomic nervous system from the kidney by performing surgical sympathectomy in patients with hypertension. These surgical approaches were ultimately abandoned because they were associated with unacceptable peri-operative morbidity and mortality.

The old concept of treating refractory HTN with renal denervation has recently been resurrected in the form of catheter based RF energy ablation of renal nerve endings within the renal artery. Initial positive results have spawned larger trials designed to show that application of RF energy within the lumen of both renal arteries can reduce blood pressure in selected patients with drug-resistant HTN. In essence, the RF catheter is advanced into the renal arteries and 4-6 discrete low-power RF energy applications are applied along the length of both arteries. This is done on a purely anatomic basis, without acute physiologic or electric endpoints for energy application. For example, it is currently unknown whether the ablative energy destroys the afferent or efferent nerve endings, neither, or both. Long-term complications from random application of RF energy into the renal arteries, such as late renal artery stenosis, are an obvious concern that needs to be evaluated.

Hypertension, heart failure, and chronic kidney disease represent a significant and growing global health issue. Current therapeutic strategies for these conditions are mainly based on lifestyle interventions and pharmacological approaches, but the rates of control of blood pressure and the therapeutic efforts to prevent progression of heart failure, chronic kidney disease, and their sequelae remain unsatisfactory, and additional options are required.

The contribution of renal sympathetic nerve activity to the development and progression of these disease states has been convincingly demonstrated in both preclinical and human experiments. Preclinical experiments in models of hypertension, myocardial infarction, heart failure, chronic kidney disease, and diabetic nephropathy have successfully used renal denervation as both an experimental tool and a therapeutic strategy.

Surgical renal denervation has been shown to be an effective means of reducing sympathetic outflow to the kidneys, increasing urine output and reducing renin release, without adversely affecting other functions of the kidney. The human transplant experience has clearly demonstrated that the denervated kidney reliably supports electrolyte and volume homeostasis in free-living humans. On the basis of these findings and in view of the demand for alternative treatment options, targeting the renal sympathetic nerves as a major player in the pathophysiology of hypertension, kidney disease, and heart failure is a very attractive therapeutic approach.

Role of Renal Sympathetic Nerves in Cardiovascular and Kidney Disease

The renal sympathetic nervous system has been identified as a major contributor to the complex pathophysiology of hypertension, states of volume overload (such as heart failure), and progressive renal disease, both experimentally and in humans. (See DiBona GF, "The sympathetic nervous system and hypertension: recent developments," Hypertension, 2004; 43:147-150). It is now widely accepted that essential hypertension is commonly neurogenic, both initiated and sustained by sympathetic nervous system over activity, (see, Esler M, Jennings G, Lambert G. Norepinephrine, "Release and the pathophysiology of primary human hypertension," Am J. Hypertens. 1989; 2:140S-146S)

There is now compelling evidence to suggest that sensory afferent signals originating from the diseased kidneys are major contributors to initiate and sustain renal sympathetic efferent activation in this patient group, which facilitates the occurrence of the well-known adverse consequences of chronic sympathetic over activity, such as hypertension, (see, Schlaich M P, Lambert E, Kaye D M, Krozowski Z, Campbell D J, Lambert G, Hastings J, Aggarwal A, Esler M D, "Sympathetic augmentation in hypertension: role of nerve firing, norepinephrine reuptake, and angiotensin neuromodulation," Hypertension, 2004; 43:169-175).

The sympathetic nerves to the kidneys terminate in the blood vessels, the juxtaglomerular apparatus, and the renal tubules. Stimulation of the renal sympathetic nerves causes increased renin release, increased sodium reabsorption, and a reduction of renal blood flow, (see, Zanchetti AS, "Neural regulation of renin release: experimental evidence and clinical implications in arterial hypertension," Circulation, 1977; 56:691-698).

Pharmacological strategies to thwart the consequences of renal efferent sympathetic stimulation include centrally acting sympatholytic drugs, Beta-blockers. However the current pharmacological strategies have significant limitations, including limited efficacy, compliance issues, adverse effects, and others. Thus, a compelling need for additional or alternative therapies exists. Renal denervation potentially offers a more direct, organ-specific strategy by targeting a mechanism crucially involved in initiating this vicious cycle. The kidneys communicate with integral structures in the central nervous system via the renal sensory afferent nerves, Renal sensory afferent nerve activity directly influences sympathetic outflow to the kidney.

Abrogation of renal sensory afferent nerves has been demonstrated in various models to have salutary effects not only on blood pressure but also on organ-specific damage caused by chronic sympathetic over activity, (see, DiBona GF, "Sympathetic nervous system and the kidney in hypertension," Curr Opin Nephrol Hypertens. 2002; 11:197-200). Thus, renal denervation is likely to be valuable in the treatment of several clinical conditions characterized by increased overall and particularly renal sympathetic activity.

Therapeutic renal denervation in humans suffers from a treatment which enables the physician to perform the procedure in an optimal and safe mode, with consistent and repeatable outcome. The irregular success of the procedure (notably in the reduction of blood pressure) might appropriately be attributed to the occasional renal denervation that was effected by the surgical procedure. The occasional dramatic success of the unproven surgical strategy fuels enthusiasm for the development of a safe, effective, and targeted procedure to functionally denervate the human kidneys.

Surgical methods of sympathectomy were associated with high perioperative morbidity and mortality, as well as long-term complications, including bowel, bladder, and erectile dysfunction, in addition to profound postural hypotension, (see, Smithwick R H, Thompson J E, "Splanchnicectomy for essential hypertension; results in 1,266 cases," JAMA. 1953; 152:1501-1504). The renal sympathetic nerves are derived from numerous spinal ganglia, and paraspinal ganglionectomy has been associated with severe and systemic adverse effects. The sympathetic renal nerves arborize throughout the adventitia of the renal artery, eliminating convenient anatomic access.

The retroperitoneal location of the kidney increases the technical difficulty of access to the nerves. In spite of these many obstacles, recent developments appear to have the potential to overcome these anatomic and technical difficulties and to provide new hope for the treatment of resistant hypertension and perhaps other clinical conditions commonly associated with increased renal sympathetic nerve activity.

In a recently published safety and proof-of-concept trial, a novel, percutaneous, catheter-based approach was applied to selectively ablate the renal sympathetic nerves without affecting other abdominal, pelvic, or lower extremity innervations, (see, Krum H, Schlaich M, Whitbourn R, Sobotka P A, Sadowski J, Bartus K, Kapelak B, Walton A, Sievert H, Thambar S, Abraham WT, Esler M., "Catheter-based renal sympathetic denervation for resistant hypertension: a multicentre safety and proof-of-principle cohort study," Lancet. 2009; 373: 1275-1281).

In spite of these many obstacles, recent developments appear to have the potential to overcome these anatomic and technical difficulties and to provide new hope for the treatment of resistant hypertension.

In summary, catheter-based therapeutic renal denervation appears to be a quick and safe procedure that resulted in a large and persistent decrease in blood pressure in patients resistant to multiple existing antihypertensive drug classes. Taken together, the safety and efficacy findings of these initial studies confirm the importance of renal sympathetic nerves in resistant hypertension and suggest that renal sympathetic denervation has the potential of therapeutic benefit in this patient population, (see, Markus P. Schlaich, Paul A. Sobotka, Henry Krum, Robert Whitbourn, Anthony Walton and Murray D. Esler, "Renal Denervation as a Therapeutic Approach for Hypertension: Novel Implications for an Old Concept,", Hypertension 2009, 54:1195-1201).

Discussion of Prior Art

The prior art discussion is centered on three fundamental aspects of the technology: The ability of the physician to navigate and control the translation and rotation of the catheter within the vasculature tree branching safely and accurately, the ability of the mapping system to identify specific location of the renal plexus active area by measuring the biopotential, and the ability of the guidance and control system to deliver the necessary amount of energy safely and accurately.

The literature provides us with evidence that due to the fact that renal sympathetic nerves are derived from numerous spinal ganglia, and paraspinal ganglionectomy has been associated with severe and systemic adverse effects. The sympathetic renal nerves arborize throughout the adventitia of the renal artery, eliminating convenient anatomic access. Surgical methods of sympathectomy were associated with high perioperative morbidity and mortality, as well as long-term complications, including bowel, bladder, and erectile dysfunction, in addition to profound postural hypotension, (see Smithwick R H, Thompson J E, "Splanchnicectomy for essential hypertension; results in 1,266 cases," JAMA. 1953; 152: 1501-1504).

The retroperitoneal location of the kidney increases the technical difficulty of access to the nerves. In spite of these many obstacles, recent developments appear to have the potential to overcome these anatomic and technical difficulties and to provide new hope for the treatment of resistant hypertension and perhaps other clinical conditions commonly associated with increased renal sympathetic nerve activity.

To achieve such outcome the system must be able to drive the diagnostic and therapeutic tool or catheter through the arterial tree by providing the necessary translational as well as rotational forces so as to travel safely to the target, such as the renal artery plexus. This task is best described in by the prior art as a "magnetically guided catheter".

Guidance and Control

There is a considerable library of prior patents wherein attempts have been made to control the movement of a catheter through the body lumens. The prior art of guiding and controlling a catheter for the specific diagnostic and therapeutic procedure involving renal denervation and generally the ability of a manual manipulation of catheter to perform neuromodulation, suffers from the fundamental inability of controlling a tethered device while being suspended in a lumen of the body cavity. The inherent instability of a tethered device is known to those familiar with the art of guiding and controlling a permanent magnet in three dimensional spaces with five degrees of freedom, a condition described formally as the Earnshaw exclusion principle.

The disclosed solutions so far provided by the prior art fail to address the fact that a medical device such as catheter with a specific mass necessitates a magnetic force and force gradient sufficient to rotate and translate such device in a suspended state. The prior art provides for literal descriptions of such alleged physical control, but do not disclose any solution that practically enables such control. This failure to enable a solution to the problem renders such prior art embodiments impractical and unusable.

Because of these drawbacks, what is needed is further development of the method and system such as described by the embodiments in Shachar, "Apparatus And Method For Catheter Guidance Control And Imaging", U.S. Pat. No. 7,769,427, which discloses a magnetically guided catheter, a system describing a magnetic guidance control and imaging method, and an apparatus using a magnetic field and field gradient to rotate, translate and levitate a medical device within a body cavity while navigating such tool or catheter through the arterial tree.

Recently, magnetic systems have been disclosed wherein magnetic fields produced by one or more electromagnets are used to guide and advance a magnetically-tipped device. The electromagnets in such systems produce large magnetic fields that are potentially dangerous to medical personnel and that can be disruptive to other equipment. A novel solution to the limitations noted by the art was developed by the introduction of a magnetic guidance system titled "*Catheter Guidance Control and Imaging apparatus (CGCI)*", by Magnetecs corp. of Inglewood Calif. The properties and embodiments of the "CGCI" apparatus and methods are detailed by the following patents and patent application publications: U.S. Pat. No. 7,769,427, Apparatus and Method for Catheter Guidance Control and Imaging; 2006/0116634, System and Method for Controlling Movement of a Surgical Tool; 2006/0114088, Apparatus and Method for Generating a Magnetic Field; 2006/0116633, System and Method for a Magnetic Catheter Tip; U.S. Pat. No. 7,280,863, System and Method for Radar-Assisted Catheter Guidance and Control; 2008/0027313, System and Method for Radar-Assisted Catheter Guidance and Control; 2007/0016006, Apparatus and Method for Shaped Magnetic Field Control for Catheter, Guidance, Control, and Imaging; 2007/0197891, Apparatus for Magnetically Deployable Catheter with Mosfet Sensor and Method for Mapping and Ablation; 2009/0248014, Apparatus for Magnetically Deployable Catheter with Mosfet Sensor and Method for Mapping and Ablation; 2008/0249395, Method And Apparatus for Controlling Catheter Positioning and Orientation; Ser. No. 12/103,518, Magnetic Linear Actuator for Deployable Catheter Tools; 2009/0253985, Apparatus and Method for Lorentz-Active Sheath Display and Control of Surgical Tools; 2009/0275828, Method and Apparatus for Creating a High Resolution Map of the Electrical and Mechanical Properties of the Heart; 2010/0130854, System and Method for a Catheter Impedance Seeking Device; Ser. No. 12/475,370, Method and Apparatus for Magnetic Waveguide Forming a Shaped Field Employing a Magnetic Aperture for Guiding and Controlling a Medical Device; Ser. No. 12/582,588, Method for Acquiring High Density Mapping Data With a Catheter Guidance System; Ser. No. 12/582,621, Method for Simulating a Catheter Guidance System for Control, Development and Training Applications; Ser. No. 12/615,176, Method for Targeting Catheter Electrodes; Ser. No. 12/707,085, System and Method for Using Tissue Contact Information in the Automated Mapping of Coronary Chambers Employing Magnetically Shaped Fields; PCT/US2009/064439, System and Method for a Catheter Impedance Seeking Device; PCT/US2010/036149, Method and Apparatus for Magnetic Waveguide Forming a Shaped Field Employing a Magnetic Aperture for Guiding and Controlling a Medical Device; PCT/US2010/052696, Method for Acquiring High Density Mapping Data With a Catheter Guidance System; and PCT/US2010/052684, Method for Simulating a Catheter Guidance System for Control, Development and Training Applications. Each of the above listed patents and patent application publications are incorporated in their entirety by reference herein.

Prior Art and Current Renal Denervation Procedures

The prior art and its various embodiments as annotated by the patents and patent application publications noted below and are centered on the ability of the devices and systems to achieve the clinical outcome of affecting neuromodulation by means defined by the embodiments of this application.

Beetel, Robert J. et al., U.S. Pat. Application No. 2011/0200171, "Methods and apparatus for renal neuromodulation via stereotactic radiotherapy," describes methods and apparatus for renal neuromodulation via stereotactic radiotherapy for the treatment of hypertension, heart failure, chronic kidney disease, diabetes, insulin resistance, metabolic disorder or other ailments. Renal neuromodulation may be achieved by locating renal nerves and then utilizing stereotactic radiotherapy to expose the renal nerves to a radiation dose sufficient to reduce neural activity. A neural location element may be provided for locating target renal nerves, and a stereotactic radiotherapy system may be provided for exposing the located renal nerves to a radiation dose sufficient to reduce the neural activity, with reduced or minimized radiation exposure in adjacent tissue. Renal nerves may be located and targeted at the level of the ganglion and/or at postganglionic positions, as well as at pre-ganglionic positions.

Deem, Mark et al., U.S. Pat. No. 7,653,438, "Methods and apparatus for renal neuromodulation," describes methods and apparatus for renal neuromodulation using a pulsed electric field to effectuate electroporation or electrofusion. It is expected that renal neuromodulation (e.g., denervation) may, among other things, reduce expansion of an acute myocardial infarction, reduce or prevent the onset of morphological changes that are affiliated with congestive heart failure, and/or be efficacious in the treatment of end stage renal disease. Embodiments of the present invention are configured for percutaneous intravascular delivery of pulsed electric fields to achieve such neuromodulation.

Demarais, Denise et al., U.S. Pat. Application No. 2006/0206150, "Methods and apparatus for treating acute myocardial infarction," describes methods and apparatus for treating acute myocardial infarction, e.g., via a pulsed electric field, via a stimulation electric field, via localized drug delivery, via high frequency ultrasound, via thermal techniques, etc. Such neuromodulation may effectuate irreversible electroporation or electrofusion, necrosis and/or inducement of apoptosis, alteration of gene expression, action potential attenuation or blockade, changes in cytokine up-regulation and other conditions in target neural fibers. In some embodiments, neuromodulation is applied to neural fibers that contribute to renal function. In some embodiments, such neuromodulation is performed in a bilateral fashion. Bilateral renal neuromodulation may provide enhanced therapeutic effect in some patients as compared to renal neuromodulation performed unilaterally, i.e., as compared to renal neuromodulation performed on neural tissue innervating a single kidney.

Gelfand, Mark et al., U.S. Pat. Application No. 2008/0213331, "Methods and devices for renal nerve blocking," describes a method and apparatus for treatment of cardiac and renal diseases associated with the elevated sympathetic renal nerve activity by implanting a device to block the renal nerve signals to and from the kidney. The device can be a drug pump or a drug eluding implant for targeted delivery of a nerve-blocking agent to the periarterial space of the renal artery.

Demarais, Denise et al., U.S. Pat. Application No 2010/0191112, "Ultrasound apparatuses for thermally-induced renal neuromodulation," describes methods and apparatus for thermally-induced renal neuromodulation. Thermally-induced renal neuromodulation may be achieved via direct and/or via indirect application of thermal energy to heat or cool neural fibers that contribute to renal function, or of vascular structures that feed or perfuse the neural fibers. In some embodiments, parameters of the neural fibers, of non-target tissue, or of the thermal energy delivery element, may be monitored via one or more sensors for controlling the thermally-induced neuromodulation. In some embodiments, protective elements may be provided to reduce a degree of thermal damage induced in the non-target tissues.

Wu, Andrew et al., U.S. Pat. Application No. 2011/0264011, "Multi-directional deflectable catheter apparatuses, systems, and methods for renal neuromodulation," describes multi-directional deflectable catheter apparatuses, systems, and methods for achieving renal neuromodulation by intravascular access. One aspect of the present application, for example, is directed to apparatuses, systems, and methods that incorporate a catheter treatment device comprising an elongated shaft. The elongated shaft is sized and configured to deliver a thermal element to a renal artery via an intravascular path. Thermally or electrical renal neuromodulation may be achieved via direct and/or via indirect application of thermal and/or electrical energy to heat or cool, or otherwise electrically modulate, neural fibers that contribute to renal function, or of vascular structures that feed or perfuse the neural fibers.

Demarais, Denise et al., U.S. Pat. No. 7,617,005, "Methods and apparatus for thermally-induced renal neuromodulation," describes methods and apparatus for thermally-induced renal neuromodulation. Thermally-induced renal neuromodulation may be achieved via direct and/or via indirect application of thermal energy to heat or cool neural fibers that contribute to renal function, or of vascular structures that feed or perfuse the neural fibers. In some embodiments, parameters of the neural fibers, of non-target tissue, or of the thermal energy delivery element, may be monitored via one or more sensors for controlling the thermally-induced neuromodulation. In some embodiments, protective elements may be provided to reduce a degree of thermal damage induced in the non-target tissues.

Zarins, Denise et al., U.S. Pat. Application No. 2008/0255642, "Methods and systems for thermally-induced renal neuromodulation," describes methods and system for thermally-induced renal neuromodulation. Thermally-induced renal neuromodulation may be achieved via direct and/or via indirect application of thermal energy to heat or cool neural fibers that contribute to renal function, or of vascular structures that feed or perfuse the neural fibers. In some embodiments, parameters of the neural fibers, of non-target tissue, or of the thermal energy delivery element, may be monitored via one or more sensors for controlling the thermally-induced neuromodulation. In some embodiments, protective elements may be provided to reduce a degree of thermal damage induced in the non-target tissues. In some embodiments, thermally-induced renal neuromodulation is achieved via delivery of a pulsed thermal therapy.

Leung, Mark S. et al., U.S. Pat. Application No. 2011/0264075, "Catheter apparatuses, systems, and methods for renal neuromodulation," describes catheter apparatuses, systems, and methods for achieving renal neuromodulation by intravascular access. One aspect of the present application, for example, is directed to apparatuses, systems, and methods that incorporate a catheter treatment device comprising an elongated shaft. The elongated shaft is sized and configured to deliver an energy delivery element to a renal artery via an intravascular path. Thermal or electrical renal neuromodulation may be achieved via direct and/or via indirect application of thermal and/or electrical energy to heat or cool, or otherwise electrically modulate, neural fibers that contribute to renal function, or of vascular structures that feed or perfuse the neural fibers.

Bin Yin et al US 2011/0137200, describes a system and a method in which an electrophysiological signal is sensed capacitively with at least two closely spaced electrodes such that the electrodes experience strongly correlated skin-electrode distance variations. To be able to derive a motion artifact signal, the capacitive coupling between the electrodes and skin is made intentionally different. With a signal processing means the motion artifact signal can be removed from the measured signal to leave only the desired electrophysiological signal. Since the measured quantity is dependent on the electrode-skin distance itself, the system and method do not need to rely on the constancy of a transfer function. Hereby, they give reliable motion artifact free output signals.

Chii-Wann Lin et al in US 2010/0145179, describes a micro electrode of a high-density micro electrode array is connected to the same conducting wire. Serial switches enable sequential electrical connection of the micro electrode array. Given reasonable temporal resolution, the separation interval of two consecutive instances of the same micro electrode entering the ON state matches the temporal resolution. The micro electrode array has simple layout and small area, thereby maximizing the number of micro electrodes installed per unit area.

Paul Haefner in US 2007/0293896 describes an arrhythmia discrimination device and method involves receiving electrocardiogram signals and non-electrophysiological signals at subcutaneous locations. Both the electrocardiogram signals and non-electro physiologic signals are used to discriminate between normal sinus rhythm and an arrhythmia. An arrhythmia may be detected using electrocardiogram signals, and verified using the non-electro physiologic signals. A detection window may be initiated in response to receiving the electrocardiogram signal, and used to determine whether the non-electro physiologic signal is received at a time falling within the detection window. Heart rates may be computed based on both the electrocardiogram signals and non-electro physiologic signals. The rates may be used to discriminate between normal sinus rhythm and an arrhythmia, and used to determine absence of an arrhythmia.

Additional applications supporting the existing art are listed herein for reference; U.S. patent And application Nos.: U.S. Pat. Nos. 7,620,451; 7,937,143; 2006/0212078; 2006/0276852; 2009/0036948; 2010/0168739; 2010/0222854; 2011/0200171; U.S. Pat. No. 7,647,115; 2006/0142801; 2006/0265014; 2007/0129720; 2007/0265687; 2009/0076409; 2010/0174282; 2010/0249773; 2011/0257564; U.S. Pat. Nos. 7,620,451; 7,937,143; 2006/0212078; 2006/0276852; 2009/0036948; 2010/0168739; 2010/0222854; 2011/0200171; U.S. Pat. No. 7,647,115; 2006/0142801; 2006/0265014; 2007/0129720; 2007/0265687; 2009/0076409; 2010/0174282; 2010/0249773; and 2011/0257564.

The methods and the examples noted by the applications and patents listed above, further describe and elaborate on the existing art of renal denervation using electrodes technology, optical, ultrasonic and variety of techniques employing inferred radiation and x-ray. All the above methods are used in order to sense or identify the location of the nerve bundle, such as the right or left plexus located within the renal artery. All the patents and applications elaborate on the ability of the operator (physician), to manipulate the catheter by translating and rotating distal end to its intended target, e.g. the renal artery and specifically to the area where the right or left plexus is located. The patents with its collected embodiments and their associated specification clearly inform us of the inherent difficulties in navigating the catheter distal end from its origin (the vascular tree) to its relevant anatomical and significant clinical site. These challenges of navigating the catheter by manual manipulation with the aid of electro-mechanical mechanisms are the mainstay of the current applications. The ability of the operator to perform diagnostic-(identifying the location of the renal plexus), while travelling through the vascular tree, and subsequently performing a therapeutic procedure of denervation the renal artery, these functionalities of driving the catheter to its intended anatomical site and delivering energy to perform the procedure is the main challenge that this application with its novel detection and its remote navigation is solving as it is defined by the specification and embodiments of this application.

As shown above, the prior art suffers from the same limitations noted above as these techniques, methods, and examples uses the manual manipulations to drive the catheter distal end, while employing a variety of technologies to perform the clinical procedure of renal denervation. We supplement the review of the prior art, in order to clarify and emphasize the inherent limitations of the current techniques methods and examples so as to highlight the categorical difference of the prior art and the current invention. At the center of our differentiation is the ability to drive the catheter by manual technique using mechanical mechanism of influencing the distal end of the catheter so as to overcome the complex anatomy of the vascular tree in order to rotate and translate the catheter to its desired anatomical site, and once arrived to the site, the operator must identify precisely the renal plexus so as to deliver the energy for the purpose of denerving the active control of the sympathetic nerve system from influencing the metabolic control of that system.

It is therefore clear, that current art of manipulating the distal end of the catheter is limited to the mechanical degrees of freedom afforded by the use of varieties of manipulating the catheter distal end by the ability of such tools and techniques to influence the position and orientation of the catheter by means that are sub-optimal and that such methods and apparatus are subject to the limitations noted and that such limitations are directly related to the successful outcome of the clinical results. The limitations of guiding the catheter trough the vascular tree are known for those familiar with the art. The solution proposed by the invention will be clear and the advantage of using magnetically fitted catheter with its novel apparatus and system with MOSFET sensing array will improve the safety and efficacy of the current art.

As shown by the prior art review section, the mainstay of the art is the ability of the operator to manipulate the catheter relaying on manual translation and rotation of the distal end so as to acquire the optimal position of the catheter and by sensing the biopotential and relaying on the operator dexterity to place the catheter firmly in its desired location so as to be able to deliver curative energy in performing the procedure termed in the art as "renal denervation".

MOSFET Sensor Array

The prior art is primarily centered on the novelty of employing a MOSFET sensor array for the detection and recording of bioelectric potential as the use of the MOSFET sensor array embedded within a magnetically guided catheter is highlighted and a detailed description of the use of such method and its proposed apparatus in clinical procedure is described. Generally this procedure is a twofold operation it involve first the mapping of the site so as to diagnose and define the relevant optimal location of the ablation of nerve or ganglionic plexus. The functional modification is described so as to affect the performance of such bioelectrical activity. The remodeling of neural activity or neuromodulation is best achieved by the improvements proposed by this invention.

It is clear to those familiar with the art of electrophysiology mapping, that methods using electrode technologies of all different combinations as noted by the prior art, suffer from the inability to differentiate between signals emanating from near and far fields as the electrodes in the prior art are typically made of metal-electrolyte interface. The interface impedance in this relation is represented as a capacitor, and in a non-polarized electrode, the impedance is represented as a resistor. But in practice both capacitive and resistive components are present in the existing art, while the new method and the accompanying apparatus to this invention employ the MOSFET isolated junction, which measure the action potentials without the parasitic capacitive or resistive loads noted by the prior art.

The discussion relating to the prior art is set as a background in order to contrast and highlight the preferred embodiments of this application. The ability to perform a surgical intervention by minimally invasive use of catheter requires a precise and stable navigation and control of the distal end of the catheter. The use of magnetically guided tool as described by the CGCI coupled with the ability of the sensory apparatus to define accurately the site of the bioelectric potential and further the ability of the system to achieve the target by accurately arriving to the site is the main stay of the proposed application. The clear advantage of magnetic guidance and control of the catheter with its MOSFET sensor array is demonstrable and improve the art of neuromodulation as it provide for precision and safety of such operation.

The ability of MOSFET sensor array to identify the location of bioelectrical signal with fidelity that eliminate the current electrode technology with its short comings associated with "far field/near fields" averaging distortion and specifically the sensor's ability to depict a small bioelectric potential in the orders of micro-volts.

In spite of these many obstacles, recent developments in magnetic navigation on the one hand and signal detection employing a MOSFET sensor array appear to have the potential to overcome these anatomic and technical difficulties and further improve the indices of success by reducing unnecessary injury by the use of local monitoring of nerve impulse activity. We refer to the literature and the experimental work conducted by the C. Williams study, as in the example it is clear that it needs to define a local bioelectrical measurements, (not compromised by the averages associated with different dielectric and conductivity measures) is essential in preserving the fidelity and integrity of the signal measured, that the underlying mechanism of impedance variations within nervous tissue, (wherein the presence of myelinated tracts giving a relatively low conductivity), results in conductivity change of the tissue rises as the ion-containing, extra cellular fluid which provides for more conduction paths. The study further reported that typical values for white matter are 700 ohm-cm; for grey matter, 300 ohm-cm; and the skull is typically 5000 ohm-cm. This variation of conductivity in different tissues is the main reason why the bioelectric potentials need to be measured locally, so as to avoid the SNR (Signal to Noise Ratio) distortion associated with for example in measuring global EEG indications. In addition to differences in local conductivity between gray and white matter, the measurements from global EEG measurements are further compromised secondary to the use of medications administered at the time of surgery such as anesthetic agents, dexamethasone (given to reduce brain swelling), mannitol (an osmotic agent used for diuresis), and lasix (osmotic agent used for diuresis). Other drugs such as intraoperative anticonvulsants (i.e. phenytoin or keppra) may cause distortions in local neurophysiology. The net result, cell swelling, is really a combination of pressure across arterial cross section, medications administered, and anesthesia. Cellular swelling affects both neurons, of which neurophysiological changes are best, appreciated on a local intraoperative biopotential rather the prior art methods of electrodes detection with ground path with few feet away from the measurement site coupled with averaging of near and far fields due to the inability of the current electrodes technology to discern such small signal as shall be clear when reviewing the novelty proposed by the invention. Therefore, these cellular changes due to metabolic assimilation of mechanical as well as chemical changes are mirrored by electrical manifestations, resulting in a state which the current invention is solving.

BRIEF SUMMARY

Given the lack of precision and lack of physiologic or electric endpoint for existing RF renal denervation technologies, we have devised a means of directly recording nerve electrical activity in the walls of the renal arteries, using our unique MOSFT based catheter recording technology. The fundamental idea is as follows.

Firstly, nerve endings generate sporadic electrical activity (in the microvolt range) which can be recorded if the recording apparatus is sufficiently sensitive and if the S/N ratio can be adequately controlled such that random background noise is mostly eliminated. Typical nerve recordings require a S/N ratio>3:1 to meet the definition of neural activity. The exact location of the nerve endings within the wall of the renal artery is highly variable, and ranges from the outer lining of the artery (adventitia) to regions that lie within the middle of the renal artery wall. In any case, 91% of the nerves are within 2.0 mm of the artery lumen, making it likely that the MOSFT based sensor can detect their activity. Once detected, the nerve endings can be selectively targeted for ablation (destruction), with the loss of nerve electrical activity as the end-point for energy application. There are likely to be areas along the length and circumference of the renal arteries that are richer than others in nerve endings.

Secondly, existing mapping technologies such as St Jude Medical's NavX mapping system and Biosense Webster's Carto system, can create accurate 3-D representations of anatomic structures after a catheter has been navigated within such structures. To date the systems have been mostly used in the chambers of the heart. We propose that either of these systems can be used for creation of an adequate depiction of the renal arteries. This can be rapidly and efficiently done by an experienced operator, as the arteries are essentially two hollow tubes. Once created, these maps can be used for road mapping the sites of ablation, possibly by placing sites of highest nerve activity as recorded by the MOSFT amplifiers on the catheters onto the 3-D depiction of the arteries. In essence, we would create a "nerve activity 3-D map" of each of the renal arteries. Representative examples of sympathetic nerve activity recordings are provided in FIGS. 9C-9E. The nerve activity is characterized by abrupt onset and offset, not related to the activity of the heart. Low frequency perturbations such as respiratory movement of the renal artery can be readily filtered from these recordings.

The main tenants of the use of transistorized electrodes employing a MOSFET sensor array embedded in a catheter distal end, is to provide a electro-anatomical map that is specific with reference to the local tissue substrate will reveal the relationship between anatomical characteristics and the corresponding substrate map underlying the muscle tissue. Specifically, we refer to the fact that electrical activity and its vectorial trends are the results of the underlying substrate's electrical properties, i.e. conductivity ($\rho$) or ($S \cdot m^{-1}$) and with excitable cells and/or fibrotic formations which, if mapped, will enable a physician to diagnose the underlying arrhythmogenic cause of a disease model. This hypothesis is corroborated with the use of the novel MOSFET sensor array as it enables the local mapping of the underlying substrate with its electrical and magnetic components, as shall be shall be demonstrated by the ensuing paragraphs and their accompanying figures.

The three subject matters of technology that this invention improves are as follows:

A) The ability of the physician to navigate and control the translation and rotation of the catheter within the vasculature tree branching safely and accurately;

B) The ability of the mapping system to identify specific location of e.g. the renal plexus active area by measuring the biopotential with fidelity of pico volt range; and C) The ability of the guidance and control system (CGCI), to deliver the necessary amount of energy to the target site with specificity and safety not currently available by the "standard care" approach, and where the proposed technology of MOSFET sensor array detection and the CGCI guidance and control, enable a substantial improvement to the current clinical outcome.

The present application identifes the current limitations associated with the guidance and control of manipulating the catheter by the limited ability of using manual techniques and mechanisms of driving the distal end of the catheter. By mechanically manipulating the catheter's shaft through the proximal end. This application demonstrates a superior use of magnetically guided catheter methods and specific apparatus for such use.

This application further elaborates on the use of a system for the detection with its ability to discern the preferred anatomical site with its relevance to the outcome of the procedure, clinically defined as "Renal Denervation." The novel technique proposed by this application enables a coherent approach and an effective solution to such outcome, i.e. the ability to effect a neuromodulation that will reduce the negative effects of the connection between the sympathetic nerve system and by further to modulate and control the function of the kidney in controlling hypertension.

In the ensuing paragraphs we highlight the fact that cellular etiology does provide us with electrophysiological indications in support of the use of a MOSFET sensor array in assessing and evaluating the signal generated by bioelectric potential as well as direct measurements of nerve and ganglionic activities. We further instruct in this application that the use of the apparatus proposed to solve these and other problems associated with surgical ablation, and by the consistent application of the methods and embodiments of this invention a robust predictive outcome is enabled so as to dramatically reduce the incidence of morbidity associated with the use of mechanically translating and rotating catheter. While using a catheter to perform a neuromodulation by applying energy to block or redirect peripheral nerve impulse.

The invention and its embodiments as featured by the use of an integrated MOSFET Sensor Array solve this and other problem of local definition of reporting on essential electrophysiological parameters, without the compromise noted in the prior art.

Variability of biopotential value among patients can limit the detection of physiological events to only the most common patterns and can contribute to a high false rate. However, the present disclosure describes a solution to this problem by providing a system that automatically adjusts to each patient. Thus, a physician is not required to configure the system prior to each use. In one embodiment, the system is fitted with a mechanism that allows an operator to manually adjust the settings of the system. In another embodiment, a display menu is provided to allow an operator to select the appropriate item to adjust the system. In yet another embodiment, the adjustments allow for better categorization of the area, and the corresponding wave form type of that region in the question. A classifier determines to which of two classes an observation most likely belongs based on a comparison of its features with the learned features of training examples from each of the two classes. In another embodiment, the classifier includes threshold parameters. In another embodiment, the system captures the morphology of nerve impulse waveforms by measuring their energy at different time-scales in a local setting. This is possible because the sensors described herein provide superior sensitivities and capabilities for discerning biopotentials. The system can be fitted with a multiple solution wavelet decomposition which encodes spatial distribution.

Bioelectric signal measurements and the construction of cell and organ electromagnetic field activity maps based on these measurements has a wide range of biomedical applications in modeling and diagnostic procedures. The difficulty in these measurements and mapping procedures mainly relates to the degree the measuring tools interfere with the measured bioelectric fields and signals, thus affecting the fidelity of the boundary conditions from which the modeling and diagnostic maps are generated.

The minimally invasive non-contacting biosensor technique described in the present disclosure advantageously applies high impedance and low capacitance semiconductor sensing technology combined with techniques of eliminating the traditional double-layer ionic transfer and conductive charge injection effects. The double-layer ionic transfer and conductive charge injection effects distort the regular electromagnetic fields and activation potentials of the measured tissue. The system can also be used to diagnose conditions of cardiac arrhythmias providing ECG signals for electrocardiographic mapping, and provide EEG signals for the localization and analysis of spontaneous brain activities including the ability of measuring ganglionic bioelectrical activity for pre- or post-operational monitoring.

The use of high impedance and low capacitance semiconductor sensing technology has the advantages known in the art when using non-contact measurements (NCM), which is based on the ability of the apparatus to measure the bioelectric potentials. In one embodiment, the NCM is achieved by the fact that isolated IFET is achieved by the use of an integrated MOSFET array sensor system with its deferential output its high noise immunity and low static power consumption. An additional advantage is the fact that static CMOS gates are very power efficient because they dissipate nearly zero power when idle, hence do not inject additional noise to the tissue. In another embodiment, the system uses a non-invasive boundary condition sensor technique in which a plurality of measuring devices is embedded on a distal end of a catheter. The measuring devices collect simultaneous signal data sets from the surface of an area covered by the catheter adjacent for example, to the renal artery. The usefulness of the collected data is evident by: (i) the location of the data points and the measured signals (such as, for example, biopotential, pressure and temperature), which provide direct and local values of critical parameters at particular places within the renal artery region, and (ii) the data location and signal value-matrixes provide the boundary conditions of the patient's tissue so as to compute and map the field and signal propagation distribution within the volume of the artery. In the situation where the arterial structure is being monitored, this system advantageously pinpoints the main sources and high intensity loci's of spontaneous nerve activity. From the specific data (iii) the physician can monitor particular areas and symptoms, for example, using data from the plurality of measuring devices and (iv) a nerve impulse signal(s) map can be generated (e.g., using the inverse problem method as it is outlined below).

The accuracy of the measurement for both the monitoring and mapping procedures depends on the non-invasive qualities of the measuring device. The interface of the present innovation with the active biopotential region is capacitive. The dielectric between the device sense-plate and the renal artery plexus is an insulating material in the electrolyte of the blood.

The electrostatic field conditions need to be computed for this interface and for the inverse problem mapping method using Poisson's and Laplace's equations where the measured data serves as the boundary condition for all computations. The constants for dielectric coefficients of brain tissue are for example: gray matter dielectric constant, κ, is about 56; brain's white matter is about 43, while brain's meninges are about 58. Further details of the boundary condition modeling will improve the accuracy of the predictable algorithm when using the apparatus. Further specificity of the charge density coefficient of e.g. the cerebro-spinal fluid can be estimated or continuously measured for these computations, similarly blood vessel are modeled and set as parameters for comparison when actual measurements are conducted employing the MOSFET sensor array.

The Poisson's Equation teaches that the electrostatic field in a material with dielectric and charge properties is:

$$\frac{\partial^2 V}{\partial x^2} + \frac{\partial^2 V}{\partial y^2} + \frac{\partial^2 V}{\partial z^2} = -\frac{\rho_v}{\varepsilon} \qquad (1)$$

Where $\rho_v$ is the measured volume charge density, and $\in$ is the average dielectric constant.

Known solutions of partial differential equations fitting the Poisson's Equation is performed to obtain the electrostatic field distribution along the surface area of the measurement site and/or the field map within the tissue.

Laplace's Equation describes for the charge-free insulation layer of the sensing array:

$$\frac{\partial^2 V}{\partial x^2} + \frac{\partial^2 V}{\partial y^2} + \frac{\partial^2 V}{\partial z^2} = 0 \qquad (2)$$

The solution methods, using the boundary condition locations and measured signal values are similar to the Poisson's Equation. Other numerical solutions may employ a known differential equation solutions which results in a minimum error for the boundary conditions.

The non-contacting, sensing by the membrane surface has an insulated silver (or platinum) plate to sense the facing tissue electrostatic field. The electric field intensity between this plate and the tissue is calculated from the Poisson's Equation and is further simplified for the case of two parallel plates representing the capacitor formed by the insulated sensing plate, and the tissue, at distance d.

$$E_d = \frac{\rho_v \cdot d^3}{3 \cdot \varepsilon} - \frac{\rho_v \cdot d^2 \cdot d_0}{2 \cdot \varepsilon} + \frac{\rho_v \cdot d_0^3}{12 \cdot \varepsilon} [V/m] \ d \geq d_0. \quad (3)$$

Where $d_0$ is the minimum distance defined by the insulation layer.

However, using any of these methods requires accurate boundary condition measurements which produce minimum error due to the measurement itself. The present disclosure describes measuring techniques which enable such measurements.

In one embodiment, a MOSFET having a matrix form of sensors embedded therein is described which directly measures the local biopotential with its fractionated and continuous signals, analyzes such bioelectrical potentials and displays a measurement.

In another embodiment, a MOSFET array sensor system is fitted with an analyzing module for processing bioelectric signals so as to render a predictive value relative to the viability of the local tissue sampled by the apparatus is disclosed.

In an another embodiment a monitoring system for displaying measured parameters such as bioelectric potential, pressure as a measure of impedance, temperature, and impedance of the tissue underlying the MOSFET sensor array is disclosed. The sensor embedded in the catheter can take the form of any of several sensing devices which directly measures a parameter indicative of cellular metabolism, tissue blood flow, or tissue oxygenation as it is reflected by its electrical equivalent values through capacitive, conductive, and or resistive processes.

In another embodiment, a plurality of sensors is strategically mounted in a matrix like arrangement so as to monitor various parameters, such as, for example, surface tension, blood flow, tissue metabolism, bioelectric potential, EEG, or the like.

In another embodiment, the signal processing unit can be a multi-channel processor with a matrix array sensor. The signal processor is configured to convert the signals from the sensors from an analog signal to a digital signal using an ADC, digitizer, serializer, and/or a buffer.

In another embodiment, the signal is amplified and fed to a display unit which may be a strip chart recorder, CRT or LCD display, or converted to an audio tone output.

In another embodiment, an audio alarm tone generator can be used for surgical procedures where the physician can be informed of the data resulted from the sensory outputs of the invention.

In another embodiment, the protocol of the audio pitch and the duration of tone pulses can be used to indicate the status of the underlying tissue conditions based on a "look-up tables".

In another embodiment, the alarm threshold can be defined as a measure of clinically relevant values as defined by the underlying conditions of the tissue examined so as to produce a tone or other output relative to the sensed variable which deviates from a permissible window and established threshold values.

In another embodiment, the sensor array is distributed along the axial/radial dimensions of the catheter so as to clock the relative location of the individual sensor so as to provide a spatio-temporal data point coupled with its bioelectric potential value generated by such sensor and where the data forms the matrix which form the electro anatomical map of the measured site.

Nevertheless, there is a great and still unsatisfied need for an apparatus and method for guiding, steering, and advancing invasive devices and for accurately controlling their positions for providing positioning of magnetic fields and field gradient, for providing a fields configured to push/pull, bend/rotate, and by further enabling the apparatus to align the catheter to achieve controlled movement in three dimensional space. This application further improves the efficacy and safety of the procedure by providing for high fidelity sensing of the nerve bundle electrical activity which has a direct measure to the outcome of the procedure efficacy and safety.

In the ensuing paragraphs we highlight the fact that cellular etiology do provide us with electrophysiological indications, we further instruct in this application that the use of the apparatus proposed solve these and other problems associated with surgical ablation, and by the consistent application of the methods and embodiments of this invention a robust predictive outcome is enabled so as to dramatically reduce the incidence of morbidity associated with the use of mechanically translating and rotating catheter in the renal artery. While using a catheter to perform a neuromodulation by applying energy to block or redirect peripheral nerve impulse.

The invention and its embodiments as featured by the use of an integrated MOSFET Sensor Array which solve this and other problem of local definition of reporting on essential electro-physiological parameters, without the compromise noted in the prior art.

The illustrated embodiments of the invention can thus be considered as including a system for detecting or mapping and ablating a renal nerve ending within a renal artery comprising a catheter having a body and a distal end for insertion into the renal artery, an ablation tip coupled to the distal end of the catheter, a magnet coupled to the body of the catheter, a sensor array including a plurality of MOSFET modules coupled to the body of the catheter, wherein the sensor array is arranged and configured to sense a local bioelectric potential of the renal nerve ending using the plurality of MOSFET modules, a computer accessible memory that stores the measurements of the bioelectric potential of the renal nerve ending obtained by the at least one sensor array, a computer processor communicated with the memory and the sensor array, the computer processor correlating the measurements of the bioelectric potential of the renal nerve ending sensed by the sensor array with a location of the distal end of the catheter to detect or create a map of the renal nerve ending, and a controllable magnetic field source configured to guide and control the catheter through the renal artery by magnetic interaction with the magnet to the renal nerve ending as recorded on the map to controllably position the ablation tip at the mapped renal nerve ending. The MOSFET module is a sensor that detects signal at the levels of 1 µA in a local setting or near field without the sensing more global signal averages as is typical with prior art unipolar, bipolar, or multipolar electrodes which may have a ground patch 5 feet away and an impedance of 5MΩ. The MOSFET module functions a variable resistor with a ground potential of a few kΩ at the situs of sensing.

The MOSFET modules of the sensor array include MOSFET sensor pads coupled via a capacitor to a MOSFET transistor. Coupling of the pad with different dielectric media or biopoentials varies the capacitive load on the capacitor and the bias on the MOSFET transistor. The biased MOSFET transistor thus functions as a variable resistor. The performance of the effective variable resistor with a local ground with an impedance of a few kΩ achieved using a low-current MOSFET circuit allows a local biopotential in the microvolt ranges to be detected with fidelity.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The disclosure can be better visualized by turning now to the following drawings wherein like elements are referenced by like numerals.

DEFINITIONS

All technical and scientific terms used herein have the same meanings as commonly understood by one of ordinary skill in the art to which this invention belongs and as further illustrated or supplemented below. Although any methods and materials similar or equivalent to those described herein can be used in the practice or testing of the present invention, the methods, devices, and materials are now described. All publications mentioned herein are incorporated herein by reference for the purpose of describing and disclosing the materials and methodologies which are reported in the publications which might be used in connection with the invention. Nothing herein is to be construed as an admission that the invention is not entitled to antedate such disclosure by virtue of prior invention Actual Position (AP)—The six degree of freedom position and orientation of the medical device such as catheter position is measured at the center of the distal end.

Automatic Guidance—as used refers to methods of automatically advancing, steering and pushing a catheter toward a desired position.

Automatic Guidance—Methods of automatically advancing, steering and pushing a catheter toward a desired position.

Automatic Magnetic Mode—The control mode that enables the physician to automatically guide the catheter to a target with a simple point-and-click of the mouse button.

Baroreceptors—A type of mechanoreceptor sensor located in the blood vessels that detects the pressure of blood flowing through them, which can send messages to the central nervous system to increase or decrease total peripheral resistance and cardiac output.

Biot—Savart law—an equation in electromagnetism that describes the magnetic field generated by an electric current. The vector field B depends on the magnitude, direction, length, and proximity of the electric current, and also on a fundamental constant called the magnetic constant.

Catheter—A minimally invasive medical tool used for diagnostic and therapeutic medical procedures. Catheter has a wide variety of shapes, sizes and capabilities, but all are a combination of a functional end effector.

MOSFET Sensor Array—as used refers to a system where MOSFET sensors are configured as an array that provides better fidelity of the signal measurements as well as data collection and reduces the error generated by spatial distribution of the isotropic and anisotropic wave-fronts. In one embodiment, the system maps the change in potential in the vicinity of an activation wavefront. In one embodiment, the mapping system tracks the spread of excitation in biological media such as excitable cellar structure, nerve ending or ganglionic bioelectric activity while tracking the bioelectrical dynamics with properties such as propagation velocity changes.

Desired Position (DP)—The desired or target six degree of freedom position and orientation of the catheter, or the three degree of freedom desired location for a MOSFET Sensor Array with an implied optimized orientation which is based on the orientation of the target. Three degree of freedom desired positions are typically used, and the CGCI guidance system adjusts the orientation of the MOSFET Sensor Array for maintaining optimal orientation with a moving surface.

Determining MOSFET Sensor Array Axis by Intersection of its Sensor Planes—A method for detecting the orientation of a magnetic pellet in free space using at least two 3D magnetic sensors Distal—At the most distant end, or the end of the MOSFET Sensor Array furthest within the patient.

Fiducial Alignment—The use of a fiduciary sensor on the patient that monitors the patient's position and orientation with respect to the MOSFET Sensor Array apparatus, and the use of that sensor data to synchronize the patient's local geometric coordinate system.

Geometric Location—A specific Cartesian point on the geometric map which represents the average position of the tissue location that passes through that point.

Geometric Manifold—A hollow geometric shell that represents the inner surface of a coronary chamber or a vascular structure.

Geometric Normal Vectors for Tissue Contact Direction—The anatomical features be it a chamber or vascular structure-geometry is analyzed to provide the perpendicular directions at each part of the surface which are considered the directions of optimal tissue contact.

High electron mobility transistor (HEMT), also known as heterostructure FET or modulation-doped FET (MODFET), is a field effect transistor incorporating a junction between two materials with different band gaps (i.e., a hetrojunction) as the channel instead of a doped region, as is generally the case for MOSFET.

Leaky integrator—The formal expression of a leaky integrator describes the fact that a decaying signal tends to integrate with other sources of potential as they coalesce and represent itself as an "average." The reality is that the electrocardiogram signal with its systolic wave onslaught substantially contributes to the formation of the average reading, as this signal is measured in millivolts while most of the activity of SNA and ganglionic response is measured in microvolts.

Local Coordinates and Global Coordinates, Transformation Matrices—The local coordinate system is a Cartesian coordinate set that is fixed with respect to the patients frame. Using the fiducial alignment data, transformation matrices are created and used to convert positions and orientations between the patient's local coordinate system and the referenced global coordinate system.

Motion Compensation Filter—Motion compensation filters use a fiducial reference to subtract the movement of that reference position and orientation from that of the tool coordinate position. This allows the regulator to ignore the unwanted motion as it guides the catheter from the actual position to desired position.

MOSFET metal-oxide-semiconductor field-effect transistor is a device used for amplifying or switching electronic signals. The basic principle of the device is expressed by the fact that a voltage on the oxide-insulated gate electrode can induce a conducting channel between the two other contacts called ource and drain.

Nanocrystalline magnet—are used as an embedded pallet within the tool set, such as magnetically deployable tools, which further provides for large coactivity and improvement in energy density.

Obstacle Detection and Avoidance—An algorithm for seeking out a target when it detects contact with an obstacle outside of the targeting manifold and directs the navigation Al to select a different path to Desired Position (DP).

Path Planning—The analysis of the acquired mapping geometry of the anatomical site so as to optimize the path to Desired Position (DP). Path to Tissue Contact, Target Manifold—The Navigation Al selects a path to Desired Position (DP), region of expected target, and allowable error which become the targeting manifold. Contact outside of the targeting manifold is considered to be with an obstacle.

Predictive Kinematic Algorithm, Kinematic Rest Position—A mathematical simulation of the catheter position and orientation in free space under each magnetic field setting and catheter's length.

Predictive Motion Control Cursor—The use of a predictive algorithm to produce a realistic catheter's cursor that simulates the movement and final location of a catheter before the physician commands the actual cursor there.

Proximal—Closer to the point of attachment or observation. The side of the device that is the opposite of the distal end.

Relative Contraction Displacement and Velocity—The local contraction of the tissue as measured with respect to the tissue itself.

Respiration Compensation—The patient's respiration is an additional factor body motion. Low frequency filters can use the fiducial alignment sensor data to extract the motion due to respiration and use anatomical data to compensate for it.

Runge-Kutta Ordinary Differential Equation Based Physics Engine—In the absence of position detection electrodes along the entire catheter length, the CGCI uses a mathematical simulation engine used to produce a realistic line representing the catheter relative to its anatomical site. The line gives a realistic view of the amount of catheter's line in the chamber or body cavity.

Savitzky—Golay smoothing filter—a type of filter, which essentially performs a local polynomial regression on a series of values to determine the smooth value for each point. Methods are also provided for calculating the first up to the fifth derivatives.

Six Degrees of Freedom—A coordinate set that describes both the position of an object and its orientation in space.

Tactile Feedback, Haptic Joystick Controller—To expand the physician's sensory input, tactile 'Haptic' feedback may be used in the controller so the physician can feel the surfaces, motion and obstacles within the workspace.

Tissue Contact—Where the distal end of the catheter maintains continuous contact with the surface of the anatomical structure wall throughout the respiratory cycle and any dynamics.

Tissue Displacement Map, Global Displacement—The movement of the tissue with respect to an external reference.

BRIEF DESCRIPTION OF THE DRAWINGS

FIG. 1C is a graphical representation of the input and output signals of the MOSFET sensor module.

FIG. 11 is an isometric layout of the proposed catheter with its MOSFET sensor array, irrigation, and magnetic elements.

FIG. 19 is a perspective view representing a renal artery detail.

The disclosure and its various embodiments can now be better understood by turning to the following detailed description of the preferred embodiments which are presented as illustrated examples of the embodiments defined in the claims. It is expressly understood that the embodiments as defined by the claims may be broader than the illustrated embodiments described below.

DETAILED DESCRIPTION OF THE PREFERRED EMBODIMENTS

Figure 1:
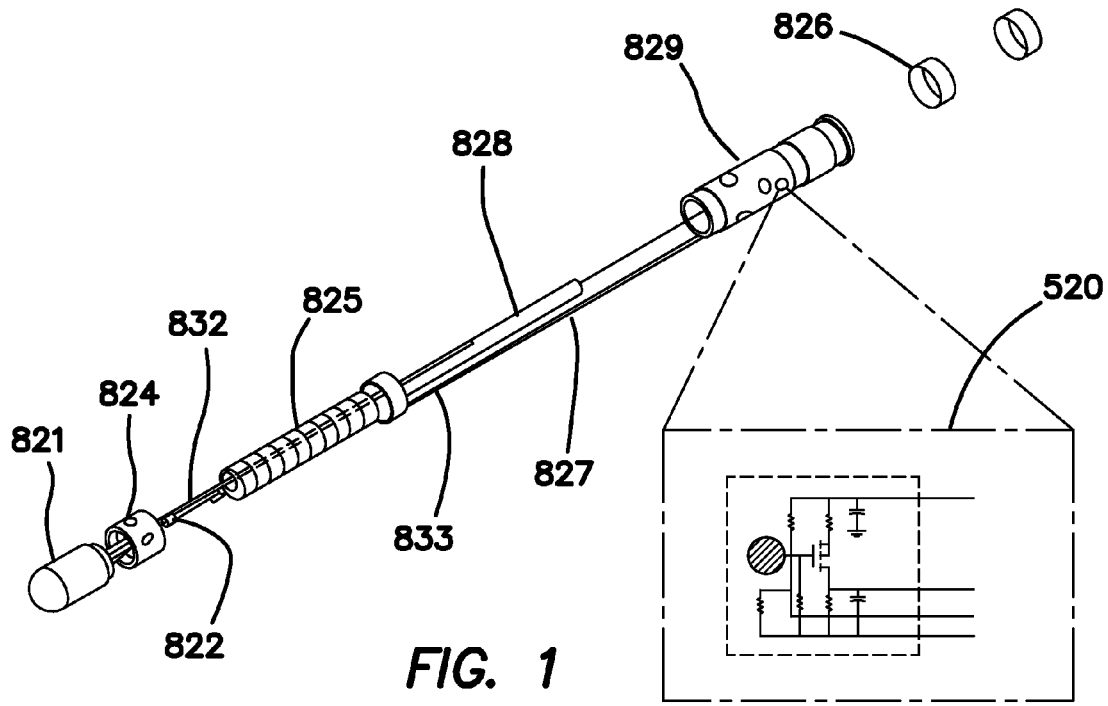
FIG. 1 is an orthographic representation of the catheter assembly comprising a MOSFET array and a RF delivery system.

FIG. 1 is an orthographic representation of the catheter 800, the assembly comprises an ablation tip 821, an irrigation manifold irrigation tube 828, a plurality of articulated permanent magnets 825, an electrode(s) 826, a sensor array holder 829, and at least one MOSFET sensor 520. In one optional embodiment of the invention, the catheter assembly 800 is configured to perform diagnostic as well as therapeutic procedures, by incorporating an irrigated manifold 824 and RF ablation tip 821, so as to enable the physician to map and ablate the desired site without the need to change tools or catheters. The use of the MOSFET sensor array 500 (seen in FIG. 4) at the site enables the operator to identify the specific site of electrical activity, i.e. bioelectric potential as well as ganglionic nerve impulse activity, while recording such event so that the operator can chose to apply the necessary RF energy to ablate which will clinically result in denerving the site or create a lesion that isolates and remodels the electrical activity so as to achieve the clinical outcome desired, e.g. electrical isolation for remodeling the electrical path to its desired standard or denerving of nerve impulse as it is commonly used in remodeling the sympathetic impulse associated with the renal plexus ganglia 345 (seen in FIG. 20) blocking on the right or left kidney.

Figure 1B:
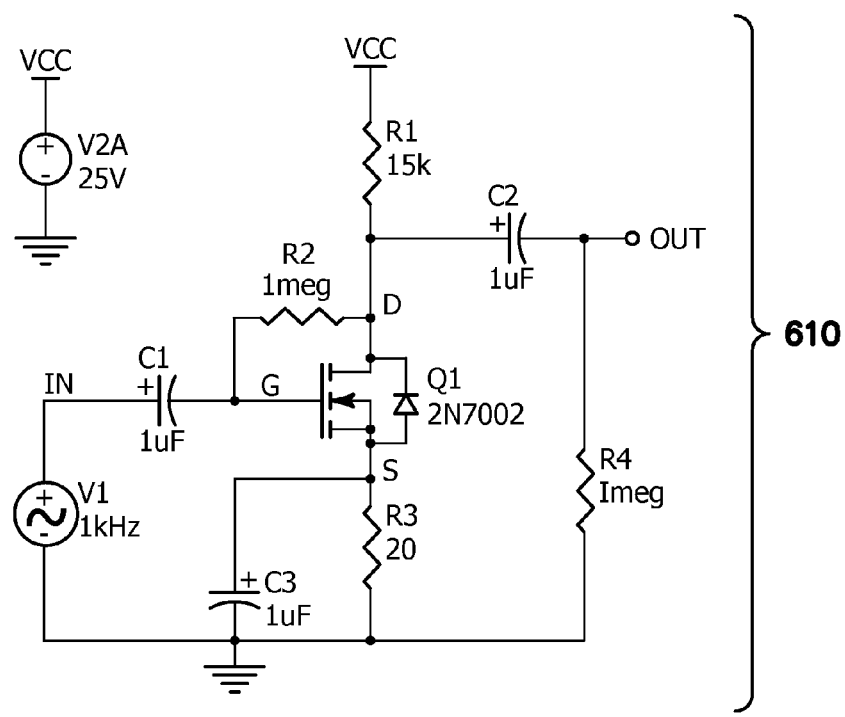
FIG. 1B is a schematic representation of a simulation layout circuit describing the basic electrical characteristics of the MOSFET sensor module.
Figure 1A:
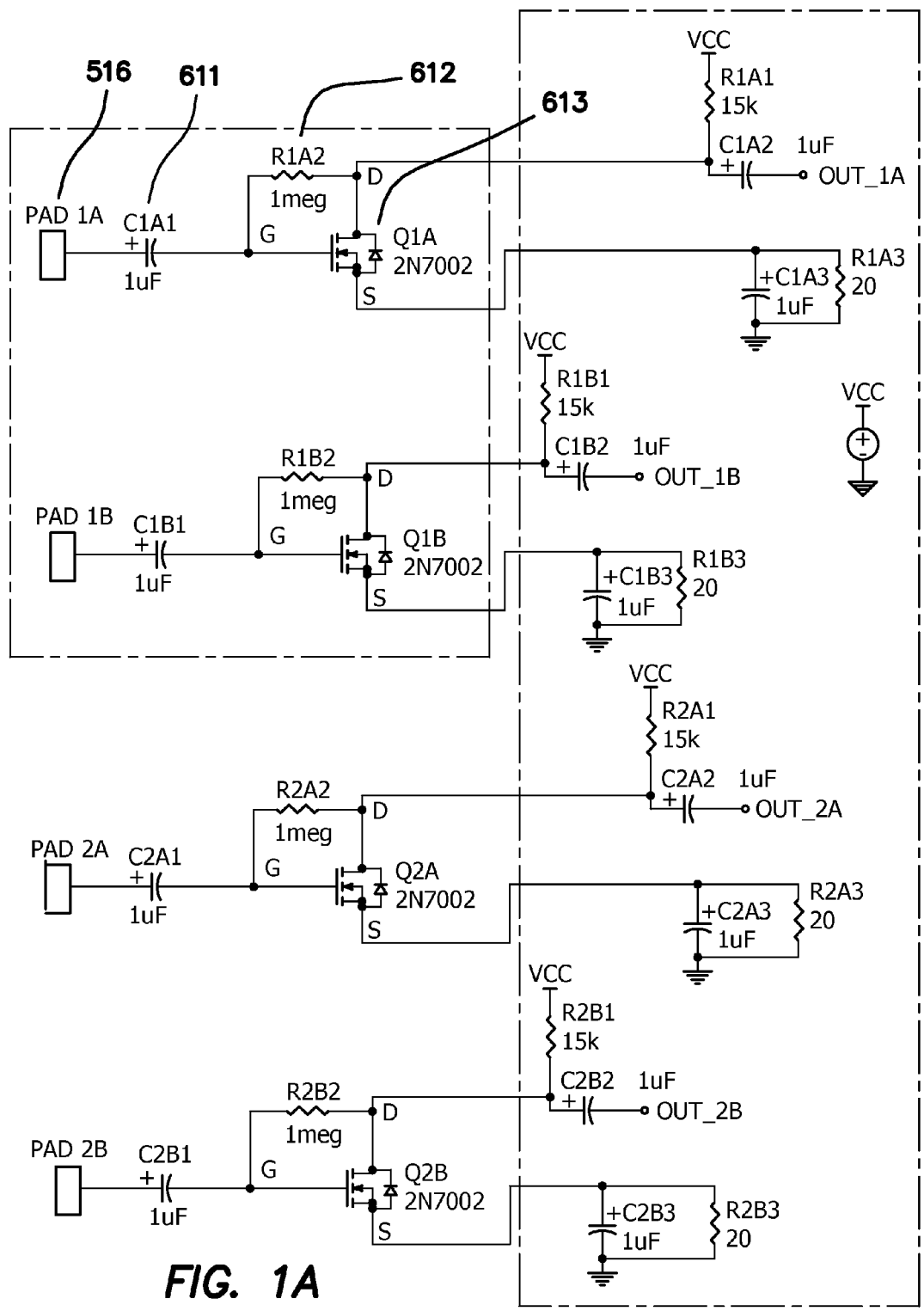
FIG. 1A is a schematic representation of a diagnostic catheter with its preferred embodiments comprising a MOSFET sensor array.

FIG. 1A is a schematic representation of a diagnostic catheter with its preferred embodiments comprising a MOSFET sensor array 500 (seen in FIG. 4) which acts as a transistorized-electrode. FIG. 1A describes an array of sensor pads connected to MOSFET common-source amplifiers. A high impedance resistor between the gate (G) and drain (D) terminals of the MOSFET biases the transistor in active mode. A resistor and capacitor between the source (S) and ground improve and stabilize small-signal gain of the circuit. Capacitors between the gate (G) and the pad, and the drain and load isolate the DC signal and ensure the small-signal (AC) amplification of the MOSFET circuit.

FIG. 1A further depicts the basic configuration of a platinum electrode-pad-1A 516 connected to a capacitor C1A1 (1 μF) 611 which provides the variable gain (G) on MOSFET transistor Q1A, (such as noted by the exemplary use of 2N7002) 613 with its resistor R1A2, (1 meg) 612.

The basic sensor module 520, form an element in a matrix array to enable the architecture of bioelectric sensor array 500 comprising of n-topple arrangements, e.g. of <8, 12, 16 or 64> members of the basic sensory inputs from a biological tissue or nerve ending firing or a summation of ganglionic plexus electrical activity.

The details of operation and the principles that govern the proposed circuit are articulated by the figures and their accompanying descriptions which demonstrate the improvements of signal fidelity of the proposed arrangements over the existing art which employ electrodes technology to capture the unipolar or bipolar characteristics of the bioelectric potential and where the ability to record electrical values of 1-2 microvolts of biopotential are limited by the physical inability to differentiate the integrated SNA signals of the systolic wave onslaught as well as the far fields propagation of multiple sources of origin generated from the various ganglionic sources. The proposed technology of MOSFET transistorized pads array is by analogy the categorical metaphor of the difference between a light microscope versus electron microscopy in differentiating a biological territory.

In other embodiments, the use of transistorized MOSFET pads 516 is to measure the local potential of a spatio-temporal event without the compromise associated with the averaging of signal and where near field response versus far field response are registered without the fidelity of local measurement capabilities available by the use of the invention. Further use of transistorized MOSFET pads 516 is to employ the device to record transmembrane ionic current flow, a bioelectric event which necessitates a fast, local and dynamic registration of the "electrical avalanche" characteristic of such biological phenomenon and further to enable the recordings of distribution's current flow in extracellular space. This type of registration enables the operator to distinguish open potential fields versus closed potential fields, and whether axons are oriented in different directions, which may cancel electrical fields (++ or −−) and hence distort the event true state.

In other electrophysiological studies, the need of using a transistorized electrode-pad is noted by Dipen Shah et al. Stating in its abstract that " . . . Additional unnecessary ablation and possibly complications can be avoided by the recognition of non-PV myocardial contributions to PV electrograms . . . " And the authors further explain that " . . . The posterior wall of the LA appendage contributes far-field electrograms to recordings from all left superior PVs (LSPV), the low lateral LA to 80% of left inferior PV (LIPV) recordings and the superior vena cava to 23% of right superior PV (RSPV) recordings. Each of these far-field components can be recognized in sinus rhythm as well as during ongoing atrial fibrillation. Finally, the creation of temporally stable and definitive PV isolation remains a currently unsolved problem." And the study concludes by stating that "A precise understanding of the electrical activation of the PVs and of the neighboring atrial structures forms the basis of the electrophysiological evaluation of PV isolation. Rigorously verified PV isolation is a cornerstone of catheter ablation for AF. Prompt recognition of non-PV electrogram components can prevent unnecessary RF ablation and may even reduce complications such as PV stenosis and phrenic nerve palsy. "Electrophysiological evaluation of pulmonary vein isolation" (Europace, 2009, 11-11)

As shown in the two examples provided, where the first example is the center on axonal nerve activity including its intensity and the signal origin, and where the second example describes one of many diagnostic dilemmas associated with the ability of the electro-anatomical as well its temporal origin of bioelectrical activities to be deciphered without the contributions of far field events which contemporaneously masks the true nature of the wave front and leads to erroneous diagnosis. The proposed transistorized electrodes technology with its spatio-temporal, local, and precise differentiation of the origin, time, intensity, frequency and multiple other matrices, is the mainstay of the proposed invention.

Figure 1D:
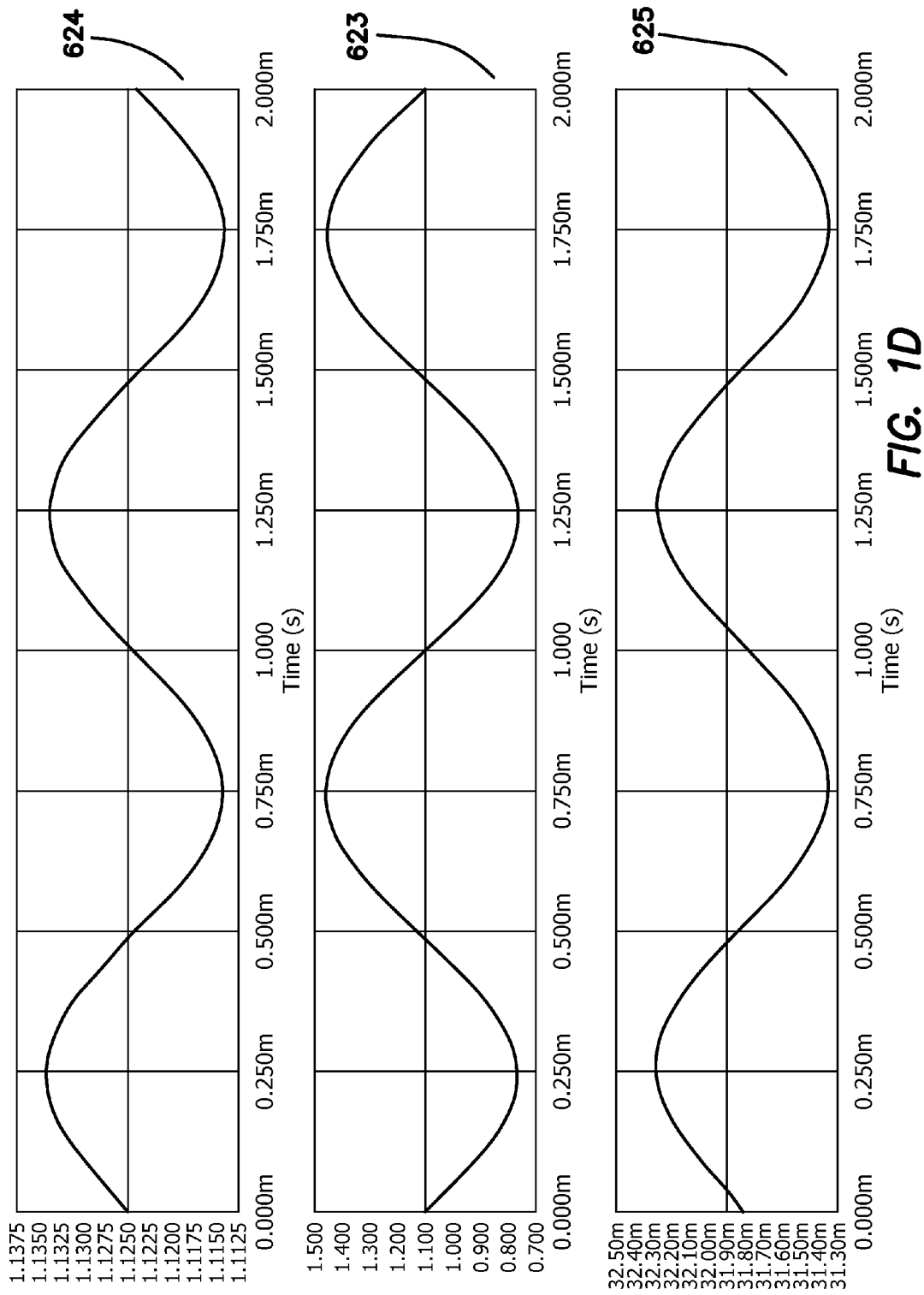
FIG. 1D is a graphical representation of the transistor gain, drain, and source outputs of the MOSFET sensor module.

FIG. 1B is a schematic representation of a simulation layout circuit 610 describing the basic electrical characteristics of the MOSFET sensor module 520, whereby the sensor module was excited with a 1 kHz using function generator (V1), and whereby the output was measured as shown in FIGS. 1C and 1D. FIG. 1B further describes a MOSFET common-source amplifier in SPICE simulation. R2 between the gate (G) and drain (D) terminals of the MOSFET biases the transistor in active mode. R3 and C3 between the source (S) and ground improve and stabilize small-signal gain of the circuit. C1 and C2 isolate the DC signal and ensure the small-signal (AC) amplification of the MOSFET circuit. The simulation indicates the ability of the circuit to vary the gain on the transistor (Q1 2N7002, N-channel enhancement mode field effect transistor) by varying the capacitance (C1) and its effect on the gain (G) of the transistor (Q1).

One skilled in the art can conceive of multiple other uses of similar MOSFET gates to perform the function as noted by this application. The essential elements proposed by this application are to enhance the ability of the sensor element to measure bioelectric potential at a site with fidelity and accuracy, including spatio-temporal representation of the local activity without the acquisition of far field and near field averages, which distort the fidelity of the local bioelectric signal. The details of the signal and its amplification without the distortion noted by the current art of employing electrodes to measure the potential with a remote ground patch is clearly noted by the current configuration proposed.

Figure 10:
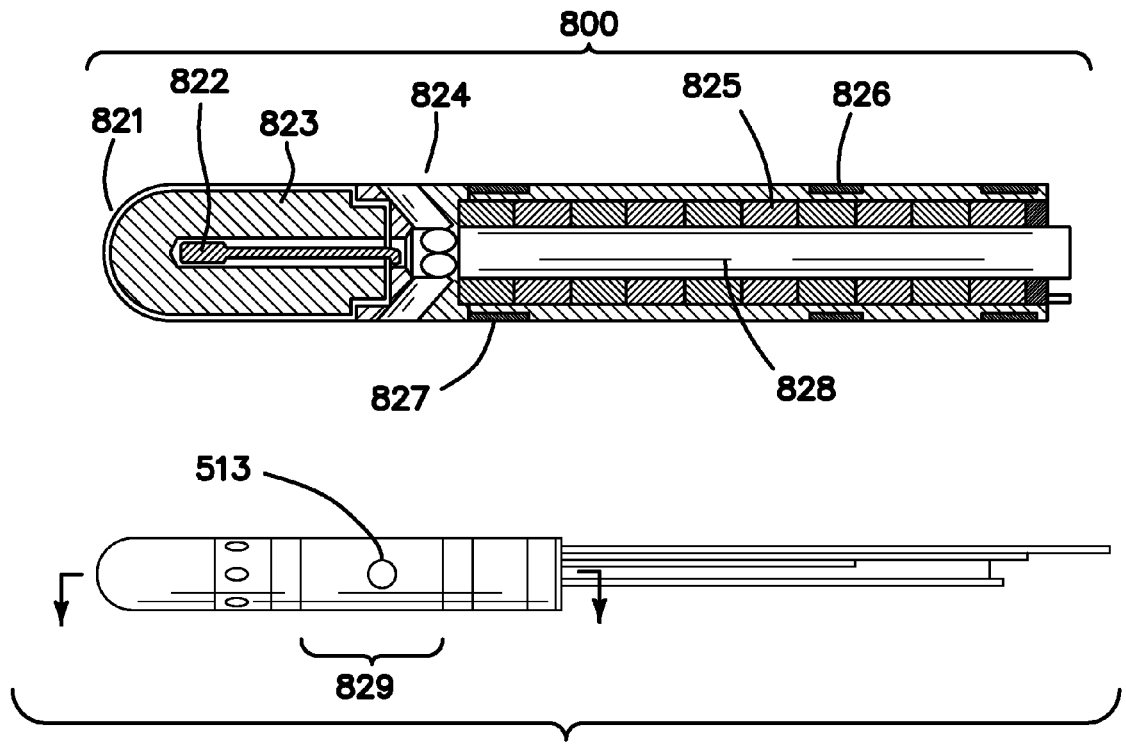
FIG. 10 is an orthographic representation of the MOSFEt sensor array depicted on the catheter assembly.

FIG. 1C is a graphical representation of the input 621 and output 622 signals of the proposed MOSFET sensor module 520. FIG. 10 further shows the input and output signal of the MOSFET simulation circuit. +/−10 mV input signal at C1 is amplified by the MOSFET amplifier circuit and produces +/−360 mV output signal at C2. Therefore, the MOSFET circuit has the small-signal (AC) amplification gain of 36.

Figure 2:
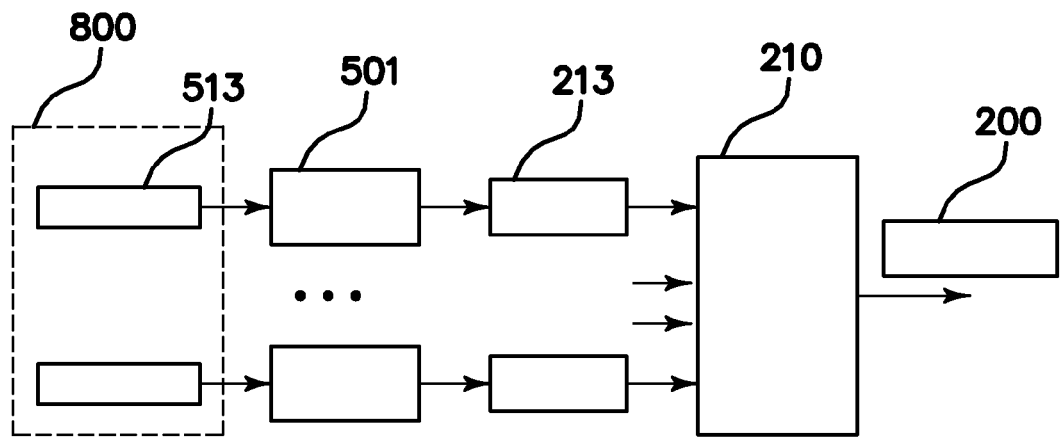
FIG. 2 is an illustration of the system block diagram for the renal denervation system.
Figure 3:
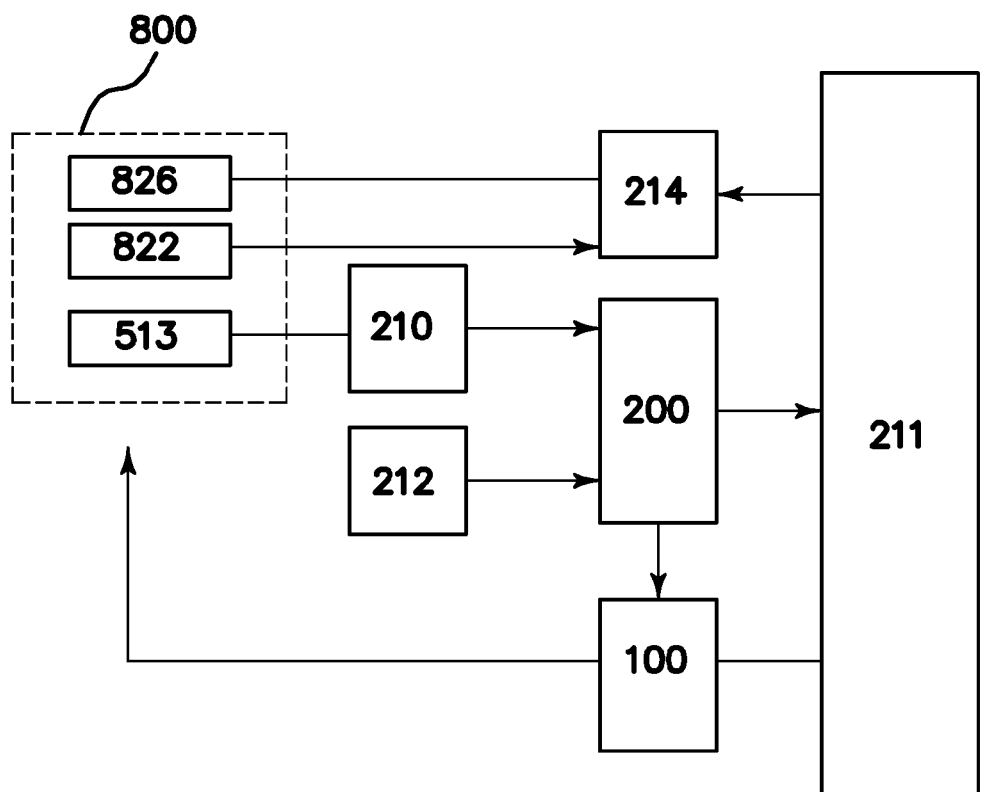
FIG. 3 is an illustration of the system block diagram for the renal denervation system with the magnetically guided and controlled navigation apparatus.

FIGS. 2 and 3 are illustrations of the system block diagram for the renal denervation system. A sensor array with MOSFET based voltage sensors 513 are located at the distal end of a catheter tip 821. The device with its supporting apparatus is employed so as to detect the location of bioelectric potential such as e.g. the right or left renal plexus. The catheter tip 821 also houses RF ablation electrodes 826 and temperature sensors 822. The catheter enables the operator to map bioelectric potential as well as the application of energy so as to denervate the nerve ending of the right or the left renal plexus after it is defined electrically and located, generating an electro anatomical map. The renal nerve detection system is located on surface of the catheter and collects the voltage readings from the surface of the tissue, the matrix of data generated by the MOSFET voltage sensors and determines proximity of the fibers of the renal plexus by identifying the bioelectric potential. The sensor data is then combined with the catheter position data by the renal nerve mapping system. The renal nerve mapping system generates the coordinates (x, y, and z) of the renal fibers so that they can be targeted for ablation. Using the renal nerve mapping data 203, and the operator console 211 the operator is able to magnetically navigate the tip of the catheter 821 with the CGCI 100 apparatus. The ablation control unit 214 controls the RF energy radiated by the RF ablation electrodes 826 at the catheter tip. Temperature sensors 822 at the catheter tip also collect readings during radiation and transmit it back to the ablation controller.

Figure 4:
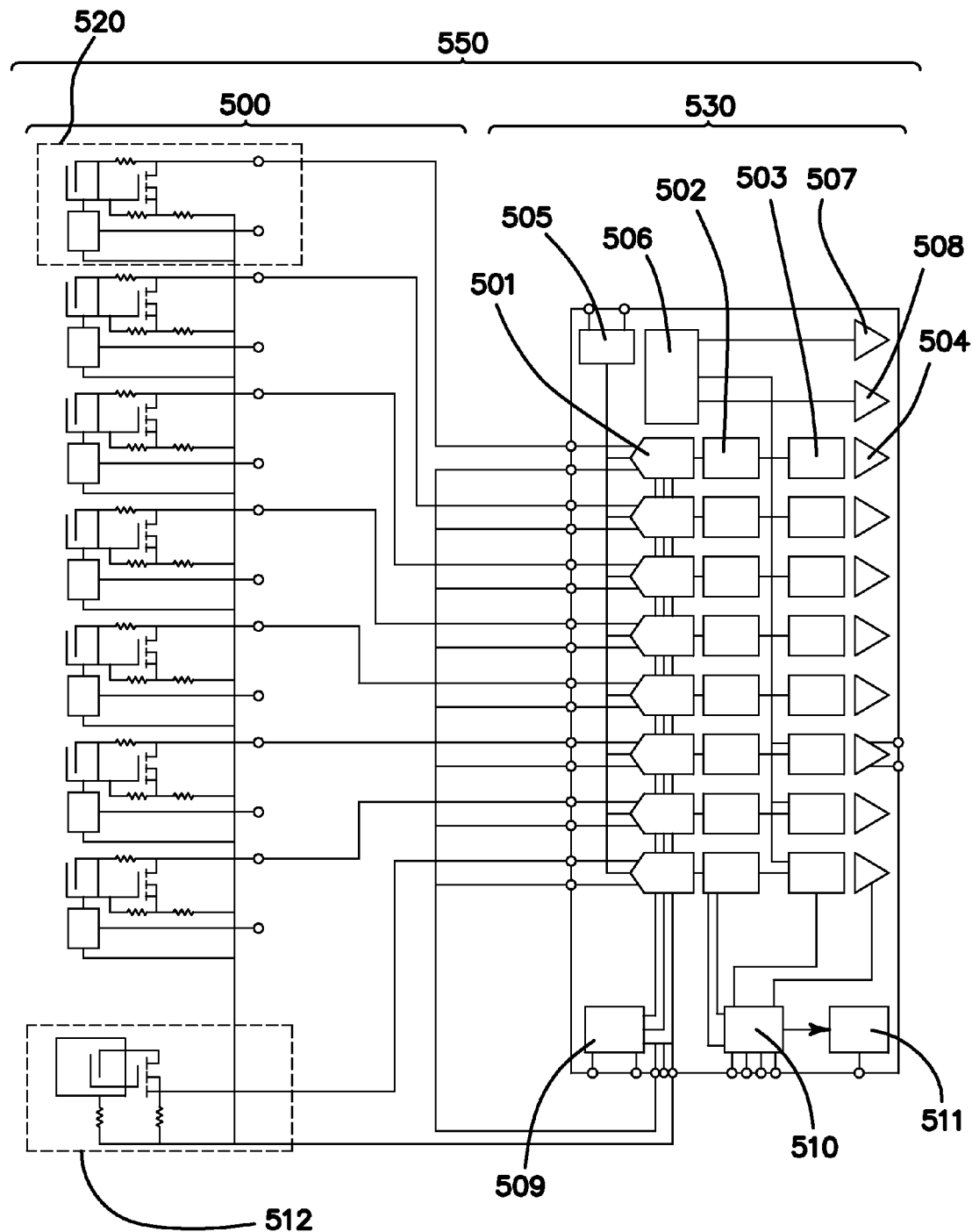
FIG. 4 is a schematic outline of the MOSFET sensor array with its associated circuitry.

FIG. 4 is a schematic outline of the MOSFET sensor array residing on the distal end of the catheter shaft depicting the architecture of enhancing the basic MOSFET sensor module 520 by demonstrating the ability of the circuit to capture, record, and analyze the bioelectric potential data generated from a local site and transmitted to a remote controller without the degradation associated with the current technology. The system architecture consists of three blocks. One of the blocks is a multi-channel integrated MOSFET sensor array 500. The array 500 includes modules 520. Modules 520 include an optional pressure transducer 515 with its extended MOSFET gate 513, biopotential detector employing a MOSFET gate, and temperature sensor 521. The circuit of the combined three sensors and its configuration are identified by reference numeral 550. The MOSFET sensor array of FIG. 4 integrated with pressure and temperature sensors provides realistic conditions for defining the sensed dielectric media as it varies from patient to patient and while the patient is under different medications. The sensor array 500 is linked to a calibration element 512. The calibration element 512 includes another MOSFET gate with a fixed value at a nominal potential. The output difference between the MOSFET 513 and the calibration element 512 provides the MOSFET output. The calibration element 512 determines the ability of the MOSFET module to self-calibrate relative to variability of the biological media due to medication, anesthesia, and fluid intake, as this process will change the gain setting of the measurement. The sensing pad 516 with its MOSFET transistor 513 and the isolated reference MOSFET 586 as a reference gate in FIG. 7C have been combined to generate a differential output which enables the circuit to detect the environment without the "noise" generated by the variability of the local setting. For example, changing of dielectric value, as noted above, would have rendered the measurements of MOSFET 516 to be inaccurate because of the environmental change.

The integrated sensor array outputs are fed to the second block 530 of the system. The second block 530 includes an analog-to-digital converter (ADC) 501, a digitizer 502, a serializer 503, an output driver 504, a clock buffer 505, a phase lock loop 506, a first clock buffer 507 and a second clock buffer 508, a reference 509, set registers 510, and ADC controls 511. In summary the integrated sensor array 500 is connected to an ADC with serial output 530 which forms an embodiment of the invention. The advantage of such an embedded MOSFET sensor array 500 is clear to those familiar with the art, as is described by the detail description of its intended operation and specifically its use in identifying the precise site of a biopotential activity and the sensor ability to discern near field from far field signals.

Figure 5:
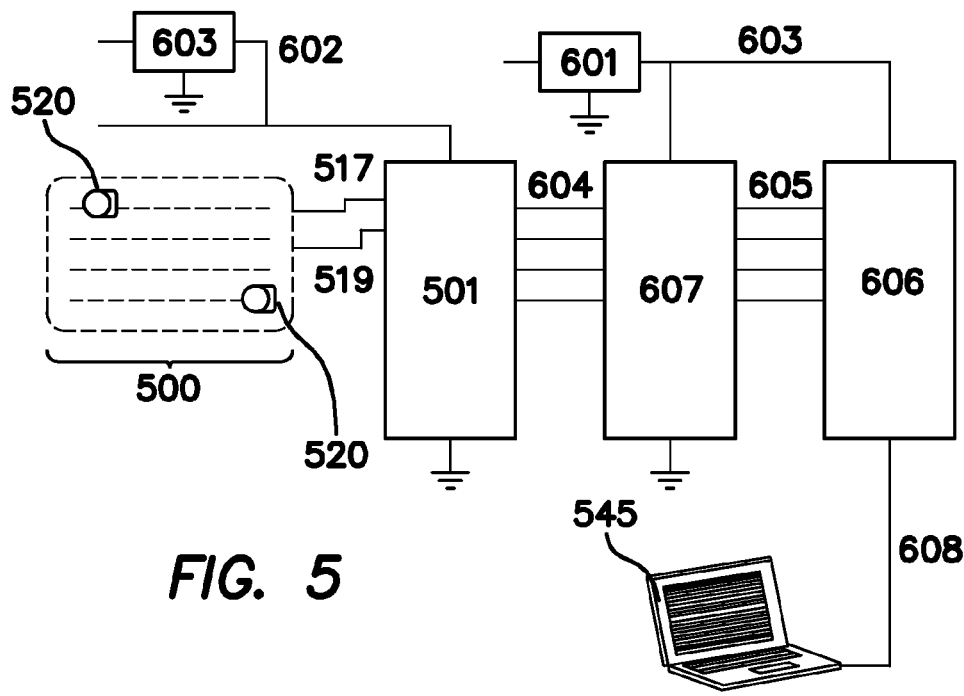
FIG. 5 is an illustration of a system block diagram for the measuring and recording of the MOSFET sensor array.

FIG. 5 is an illustration of an embodiment of the apparatus 600 for measuring and predicting electrophysiological parameters associated with the use of the MOSFET array 500 to define the proximity of the sensor to the tissue surface and for measuring the bioelectric potential of the site. The apparatus 600 is optionally fitted with pressure information relative to a correlated impedance values (known in the art as "look-up-tables"), and as shall be evident from the theory and principle of operation of the module 520. Data exerted by the catheter on the surface of the artery inner lumen further provide a measure of pressure generated while touching the arterial inner diameter of the artery by means of electrical properties such as dielectric and conductivity variation of arterial structure versus that of the vain. Blood pull impedance versus excitable cell or nerve ending. The conductivity a and relative permeability p of the tissue at the site of measurements will provide a measure of impedance which can be addressable by the look-up-tables. The sensing mechanism is a measure of the distance of the MOSFET sensor array 500 to the biological site, e.g. renal artery structure and it is based and relay on the physical properties of the medium the catheter is located in. One measure of the sensor is a correlation of impedance value as a measure of contact pressure exerted by the catheter and the site in question.

In one embodiment of the present invention, the integrated MOSFET sensor array 500 employs an integrated measure of contact as a measure of impedance value. The impedance measure derived from the sensor array 500 produces analog voltage signals corresponding to biopotential, impedance measure, and temperature information by the MOSFET sensor array 500 and its recording system 530. The bioelectric potential signal 518 is conveyed by the AC voltage at one of the outputs 517 of the biopotential due to pressure exerted between the sensor located at the distal end of the catheter, while the DC voltage of the output 519 indicates if the catheter is in contact with the arterial structure or the catheter distal end is suspended within the lumen of the vascular inner diameter. This measure is a function of the varying impedance values relative to the electrical properties of the vessel's dielectric, conductivity $\sigma$ and relative permeability $\mu$.

The basic relationship between the MOSFET sensor array 500 and the biological media while measuring impedance value take the form of $$Z = \sqrt{\frac{j\omega\mu}{\sigma + j\omega\varepsilon}}$$

where $\mu$ is the magnetic permeability, $\in$ is the electric permittivity and $\sigma$ is the electrical conductivity of the biological media/material the wave is travelling through and $\omega$ is the angular frequency of the wave. So the impedance measured by the MOSFET will yield value similar to such measure in free space, $\mu = 4\pi \times 10^{-7}$ $H/m$ and $\in \approx 8.854 \times 10^{-12}$ $F/m$.

So, the value of wave impedance in free space is approx.

$$Z \approx \frac{377}{\sqrt{\varepsilon_r}} \Omega,$$

the Z measure vary within the population, but it is clearly different when measured in the suspended state of the sensory apparatus as compared with its value when the sensory array of the catheter is touching alongside of the artery or tissue. The Z value provides the MOSFET sensor array 500 with a clear measure of determining the sensor proximity to the arterial structure or its contact. This measure is used by the current invention to facilitate a consistent application of the sensory apparatus during the mapping phase of the procedure when defining the exact location of the site, i.e. depicting the biopotential value, amplitude, frequency etc. and by enabling an accurate account of the position measured, the operator is able to deliver the curative energy to effect the intended goal of neuro modulation, and as specifically proposed by this application, the use of novel MOSFET sensory array 500 combined with precise remote magnetic navigation (CGCI) 100 to safely and effectively perform renal denervation procedure.

The array 500 sensed the displacement of the transducer 515 via membrane 516. The other output 519 produces analog voltage corresponding to the temperature device 521. These outputs (517 & 519) are connected to an analog to digital converter 501, which digitizes the bioelectric potential, the pressure as a relative variation Z value between tissue contact versus non-contact, and temperature information at 16-bit resolution and produces the output in high speed serial data format. The ADC 501, such as LM7805 is connected to a microcontroller such as MSP430F1611 unit 607, over the Serial Peripheral Interface (SPI) Bus 604. The microcontroller 607 is used for digital signal processing tasks such as filtering out the electrical noise on the signals and detecting alarms associated with device usage.

FIGS. 4 and 5 further show the MOSFET sensor array 500 system for measuring and predicting electrophysiological parameters in measuring biopotential. In one embodiment, the integrated sensor array 500 with its pressure sensor 515 produces analog voltage signals corresponding to biopotential, pressure, and temperature information from the surface of a ganglionic nerve junction peripheral nervous system 326. The biopotential signal, for example, as depicted in the ensuing figures is conveyed by the AC voltage at one of the outputs 518 while the DC voltage of the output 517 indicates the pressure sensed by the displacement of the transducer 515, via membrane 516. The other output 519 produces analog voltage corresponding to the temperature devise 521. These outputs (517, 518, and 519) are connected to an analog to digital converter 501, which digitizes the EEG, pressure/impedance correlation, and temperature information at 16-bit resolution and produces the output in high speed serial data format. The ADC 501, such as LM7805 is connected to a Microcontroller such as MSP430F1611 unit 607, over the Serial Peripheral Interface (SPI) Bus 604. The microcontroller 607 is used for digital signal processing tasks such as filtering out the electrical noise on the signals and possibly providing a detecting audio signal associated with device usage (contact or no contact of the relevant anatomical site).

The theory of operation and the functional relationship of the sensor array 500 and its operative characteristics is further defined and described by the ensuing description. The architecture of the sensor array 500 enables the detection of biopotential signals and the pressure exerted on local tissue, as well as the temperature of the site in question.

Figure 6:
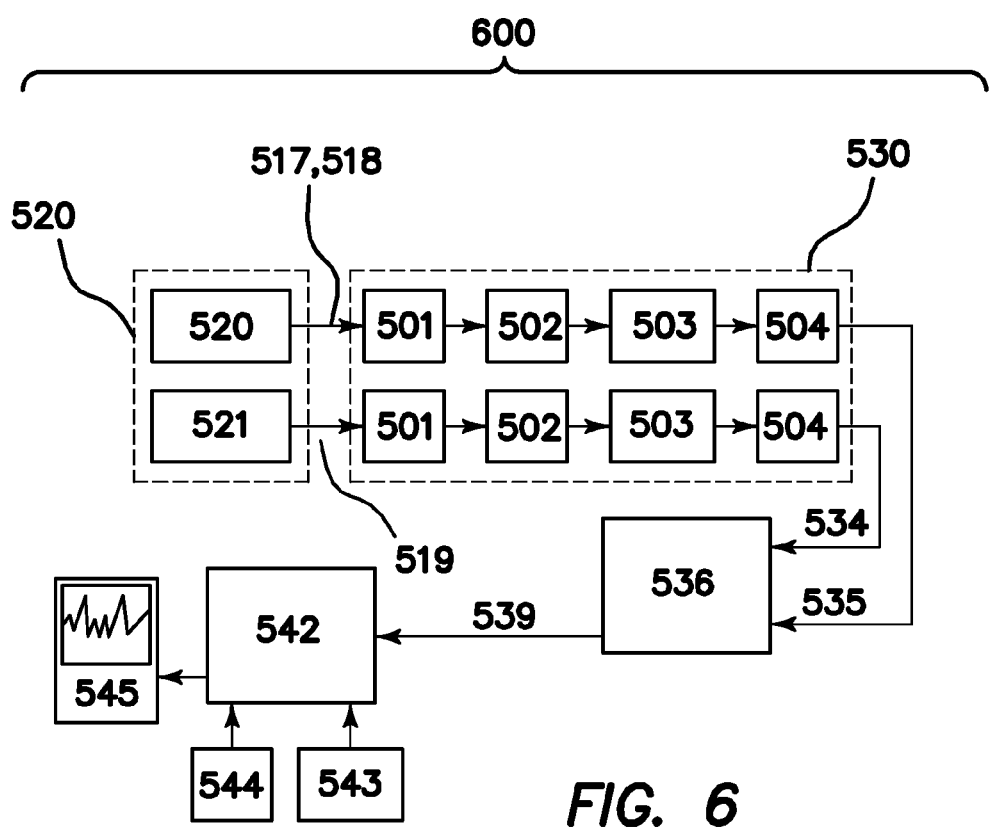
FIG. 6 is an illustration of the system block diagram with its multiple data collection channels.

FIG. 6 is a block diagram of the system 600 comprising triple signal processing modules. Each Channel 520 has three outputs. Output A 518 and Output B 517 are the bioelectric potential and pressure signals respectively. The third output 519 is the temperature measurement signal. These outputs are analogue signals. Each of these signals is converted into 16 bit data packets of digitalized information via the ADC 501, which are serially transmitted to the Microcontroller 536. The Microcontroller 536 coordinates the signal processing and display procedures. A computer console 542 with associated display 545, keyboard 543 and mouse 544 facilitates the monitoring and mapping procedures, as well as the alert system notification via the algorithm as well as parametric analysis. Further analysis that is generated by the microcontroller 536 or the host computer 542 for example includes Amplitude, Mean Frequency and or Spectral density using an FFT method.

Figure 7:
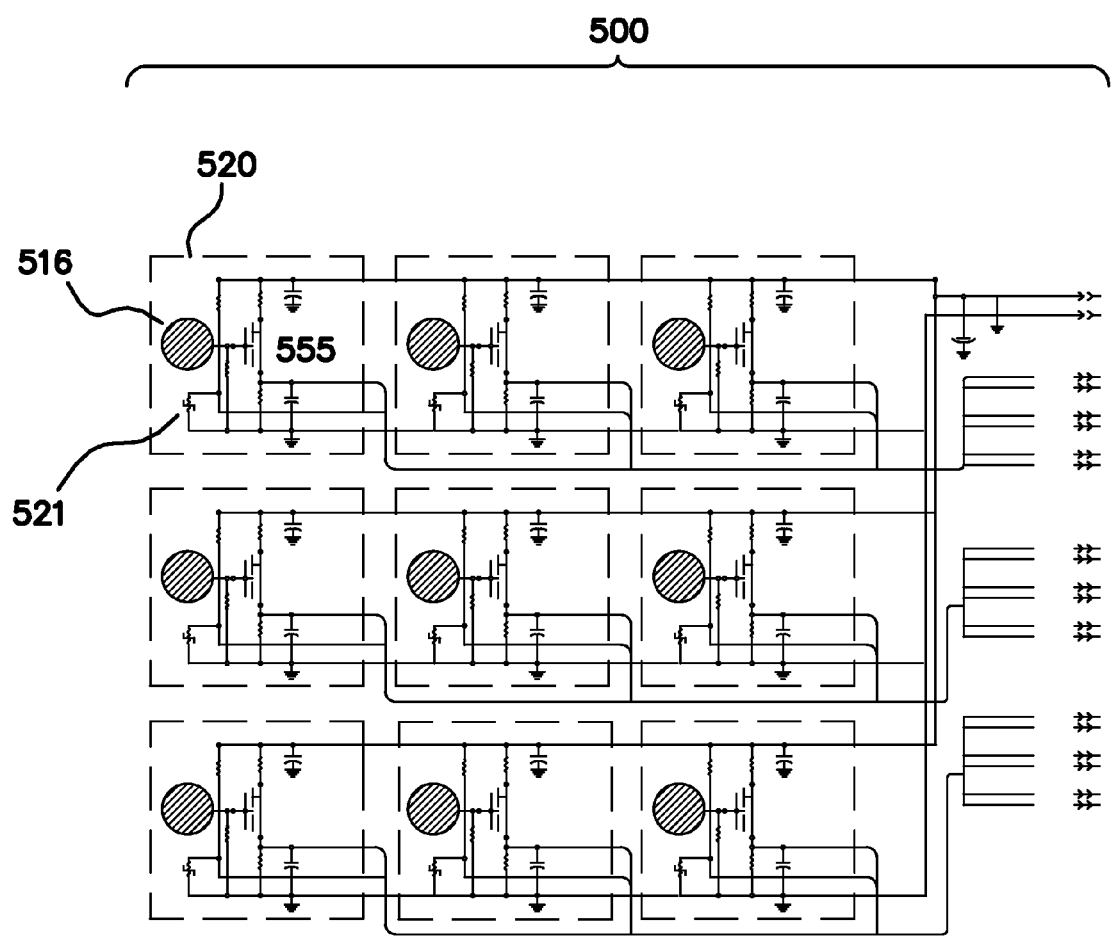
FIG. 7 illustrates an embodiment of an integrated sensor platform.
Figure 7A:
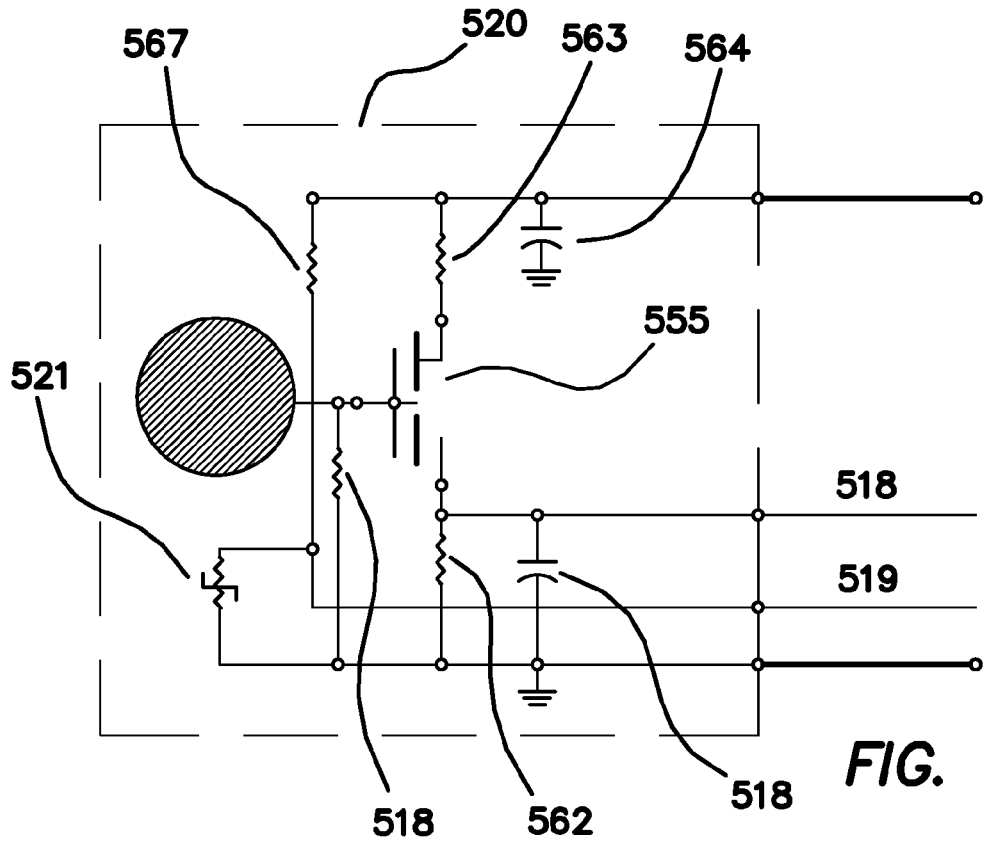
FIG. 7A is a schematic diagram of a single integrated sensory element.

FIGS. 7 and 7A illustrate an embodiment of the integrated sensor array 500, including a biopotential detection module, which employs a substitute transistor with high electron mobility transistor (HEMT), also known as heterostructure FET or modulation-doped FET (MODFET). In this embodiment, the HEMT is the combination of a junction between two materials with different band gaps (i.e., a hetrojunction) as the channel instead of a doped region, as is generally the case for MOSFET. The use of an alternate transistor can be substituted in areas where high frequency domain analysis is needed. The integrated sensory elements 520 are designated as system 500 consisting of nine channels of sensory elements 520 which form the MOSFET sensor array 500, outputting two signals (designated ST-11_P as 518 and ST-11_T as 519) per element. The basic electrostatic field sensing for each element is performed by a High Electron Mobility Transistor (HEMT) 555, a special type of field effect transistor incorporating a junction between two materials such as gallium arsenide and aluminum gallium arsenide. The sensor plate 516 is positioned along the catheter's outer wall for each HEMT 555 connected to the high impedance gate of the HEMT 555 which amplifies the electrical potential variations of the renal nerves which is sensed through the sensor plate 516 as it is touching the tissue.

FIG. 7 depicts the embodiment of a MOSFET sensor array in a matrix providing single output to a multiplexor to identify individual signal for identifying a local high-fidelity signal as opposed to an average of the total manifold.

FIG. 7A is a schematic diagram of a single integrated sensory element 520. The figure details the HEMT 555 and its associated circuitry comprising of R1 561, R2 562, R3 563, C1 564, and C2 565. In addition, a thermistor RT 521 sensing the local temperature and its bias resistor R4 217 are included in each sensory element 520 to be able to provide local temperature information. Item 518 and 519 are designated as BIO_OUT and TEMP_OUT, respectively, as the outputs of signals generated as results of biopotential sensing and temperature output, respectively. In this embodiment high-electron mobility transistors (HEMT) 555 replace the transistors 613 of FIG. 1A. The use of HEMT 555 as a replacement for the transistorized pads provides a 14 GHz transistor that has its sensitivity to dielectric variation in the sensed media.

Figure 7B:
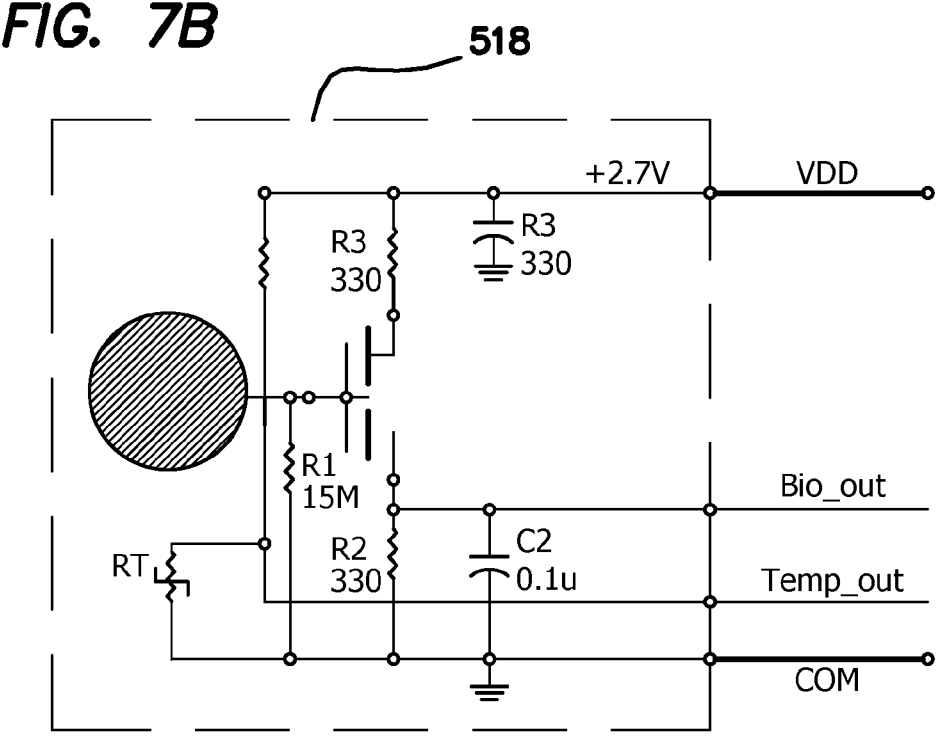
FIG. 7B is a schematic diagram showing the values of the circuit elements in a single integrated sensory element.

FIG. 7B is a schematic diagram showing the values of the circuit elements in a single integrated sensory element 520. In one embodiment, the electrical parameters of the circuit components are as follows: R1=15 Mohms, R2=330 ohms, R3=330 ohms, C1=0.1 uF, C2=0.1 uF and R4=5 kohms. The HEMT Q1 is a Fujitsu FHX04LG and the thermistor is a negative temperature coefficient thermistor NTCG163JF103FT1 from the TDK Corporation.

Figure 7C:
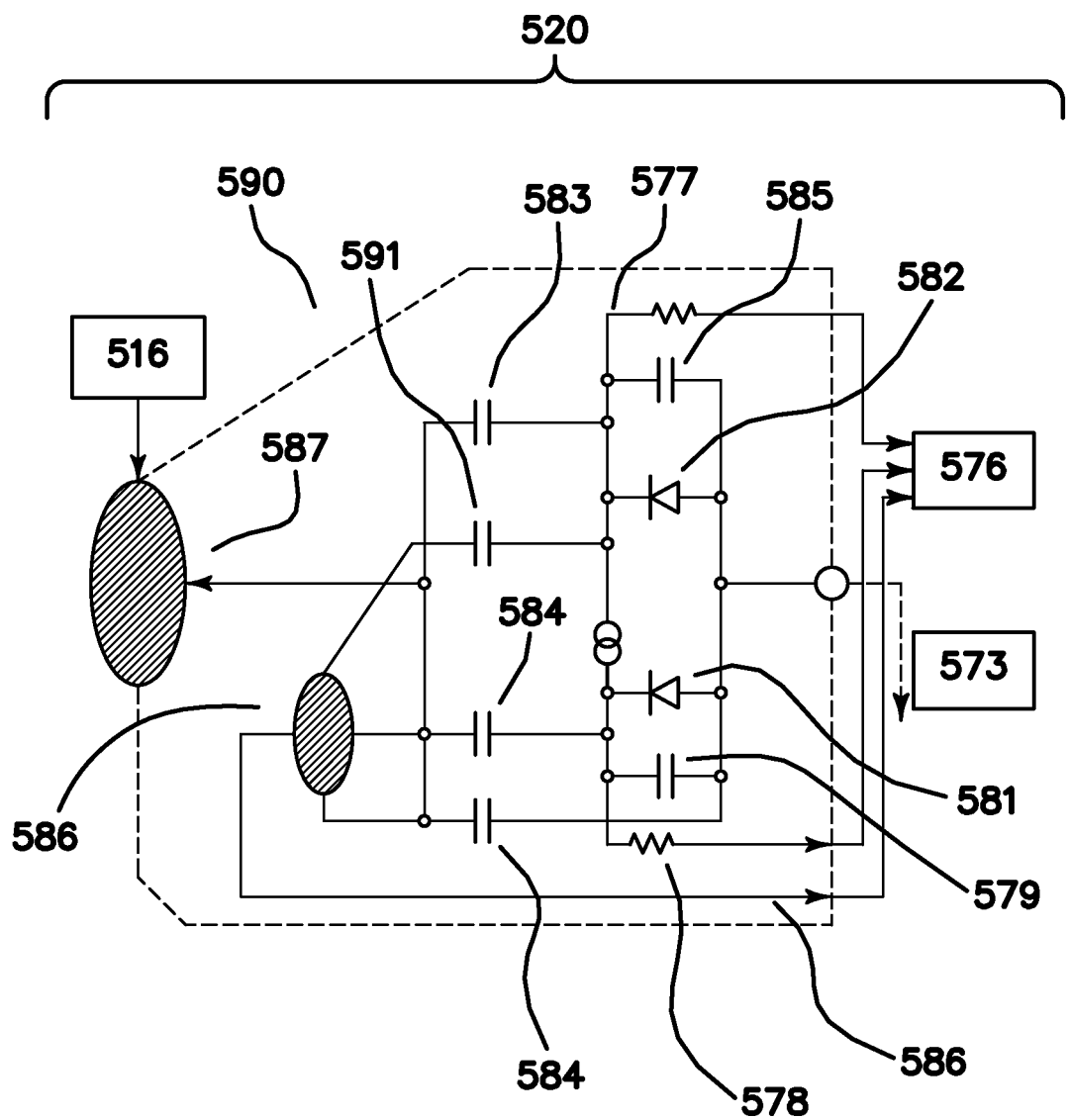
FIG. 7C is an orthographic depiction of the internal equivalent circuit of the MOSFET module.

FIG. 7C is an orthographic depiction of the internal equivalent circuit of the MOSFET module 520 (an element of the sensor array 500). In one embodiment, there are eight MOSFET sensors on the ablation and mapping apparatus 600.

The MOSFET potential sensing device is a junction field effect transistor that allows a current to flow which is proportional to an electric field, basically emulating a voltage-controlled resistor. The module 520 includes a resistor. The resistor RD 577, is a linear resistor that models the ohmic resistance of the source. The charge storage is modeled by two non-linear depletion layer capacitors, CGD 583 and CGS 584, and junction capacitors CBD 585, CGD 583, and CBS 579. The P-N junctions between the gate and source and gate and drain terminals are modeled by two parasitic diodes, VGD 582, and VGS 581. The first gate of the MOSFET sensor tip array 500 is item 587 and the second gate of the MOSFET sensor assembly 520 is item 586. The first gate 587 at the sensor tip 516 S(n) (n=1, 2, 3, . . . 8) is a relatively high impedance, insulated semiconductor structure. The module 520 behaves as voltage-controlled resistor. The potential between the gate structure 587, 586 and the drain source structure (RS 578, RD 577) semiconductor substrate defines the transconductance of the output connections 576.

By connecting the drain-source 577, 578 structure to the sensor body 590 the potential reference for measurement is established. This reference is configured as a ring 573 along with the catheter body as shown. The measurement process of probe 520 is set to a zero voltage as the drain-source 577, 578 structure, the sensor's gate junction 587 assumes the tissue 341 potential with a relatively small charging current flowing into the net parallel sum of the junction capacitors, CBD 585, CGD 583, and CGS 584. The drain-source 577, 578 voltages is then applied gradually to the device charging these capacitors from the outside power source, thereby "nulling" the current needed to form the gate so as to obtain the operating potential (about 6 VDC). The sensing procedure is relatively noninvasive to the cell as well as to the potential level and current drain of the probe 520 upon contact with biopotential of the tissue. The second gate 586 provides a biasing input so as to provide a continuous active mode for the module 520. This input is also used for self-calibration of the module 520.

Figure 7D:
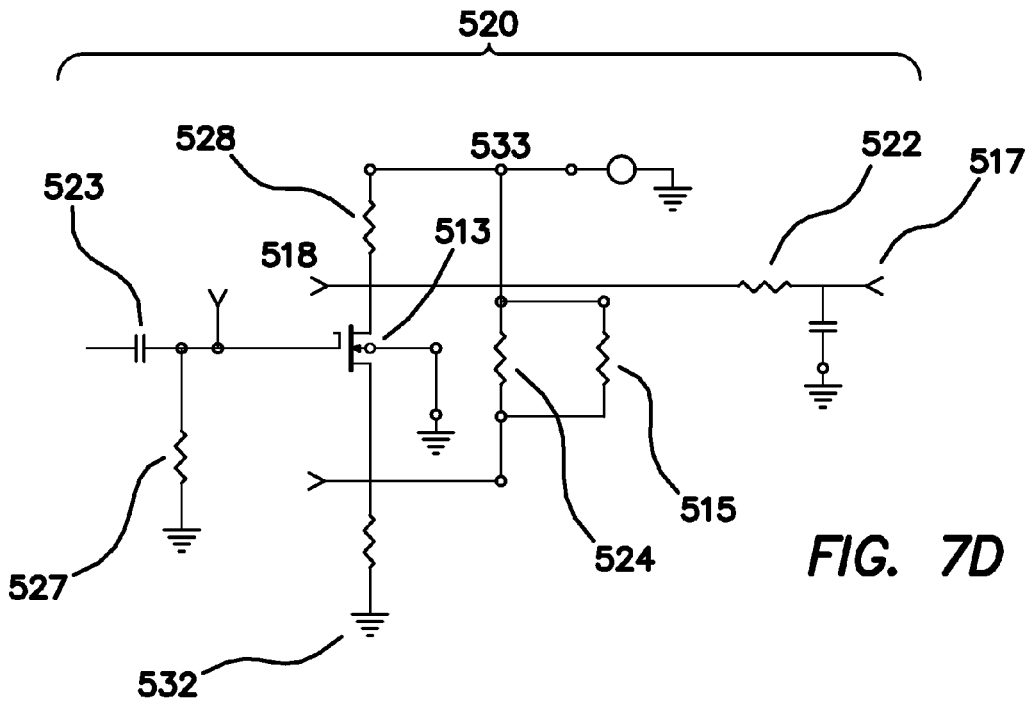
FIG. 7D is a schematic diagram (single channel) of an embodiment of the MOSFET sensing stage.

FIG. 7D is a schematic diagram of an alternative embodiment of the module 520 which is one element of a matrix array 500 comprising of the components R1 525, V1 533, R2 528, M 513, VR 517, and output temperature 519, R1 525, thermistor 521, R5 527, GRD 532, R7 522, C1 523, R3 524, and C3 531.

Figure 8:
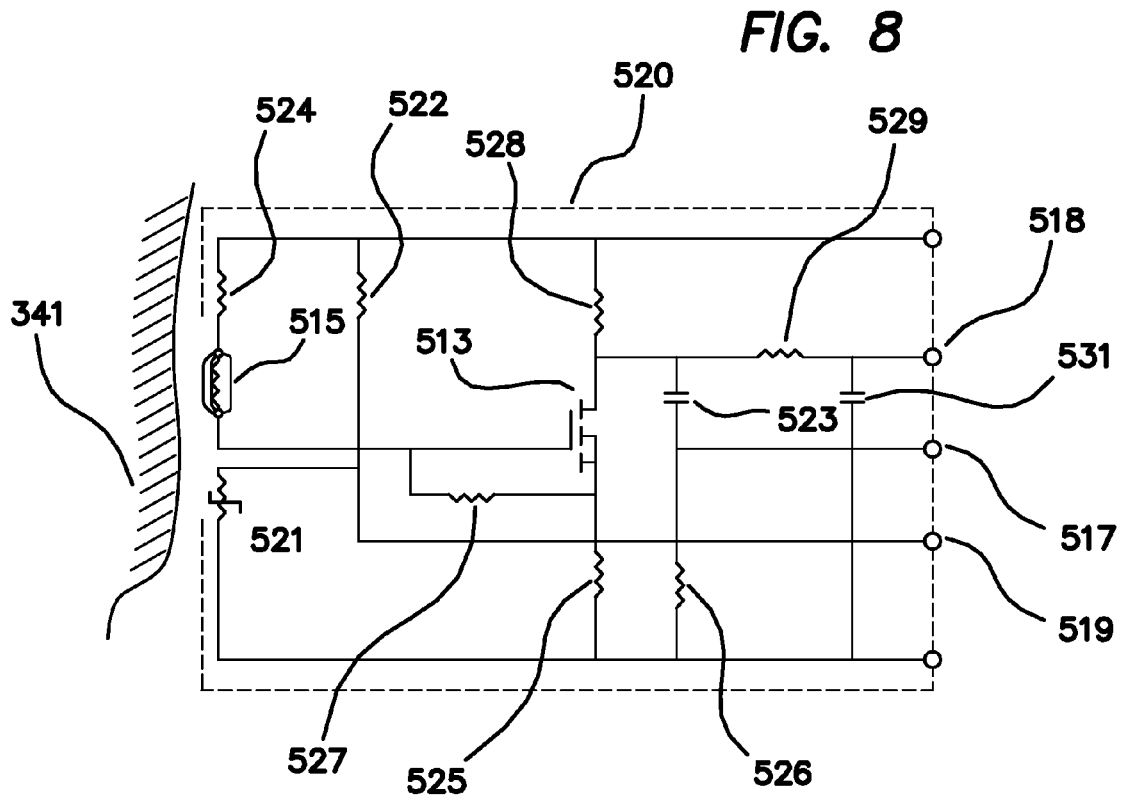
FIG. 8 is a schematic diagram (single channel) of the MOSFET sensing stage for surface contact definition detected by impedance values.

FIG. 8 is a schematic diagram of an alternative embodiment of the module 520, of the MOSFET sensing stage for surface contact definition detected by impedance values. One element of the matrix array 500 of sensors measures the effective area that is in contact with the tissue and the sensor sheath located on the catheter surface. The assembly 500 is mounted on the catheter as described, the measuring instrument for sensing pressure as well as nerve plexus or ganglionic junction bioelectric potentials are integrated using the sensing leg of the pressure sensor 515 with its insulated membrane 516, as CI capacitor 523, of the MOSFET die 513. The integration of pressure sensor 515, and biopotential data via MOSFET 513, with description of the signal flow and a schema of the circuit is further described by reviewing the signals and the respective analysis noted by the figures. A signal flow of the bioelectric IN sensing plate, CI charges as a capacitor to a potential referenced to a tissue 341 anchor point common to all sensing channels. The sensing plate is insulated from the tissue by a thin layer of insulation material. This material could be any number of insulating materials, such as Kapton, or Teflon, or any polymeric combination of these or similar materials. The capacitor plate absorbs the static and dynamic electrical charges from the adjacent surrounding tissue's 341 electromagnetic activity designated as area 342. The isolated MOSFET 513 element coupled with its pressure sensor 515 is detailed by the figure with its associated circuitry comprising of R1 525, R2 528, R3 524, R5 527, M1 513, R6 515, C3 531, R7 522, and C1 523. Items 517 and 518 are designated as the outputs of signals generated as results of displacement of the diaphragm 516 for the pressure measurements and is referred to as "Output B" and bio-elecrtric signal as "Output A". The impedance variation is used to sense the proximity of the transistor pad to the tissue. The same transistor can run via AC or DC. The impedance will increase or decrease and comparison to a predetermined or empirically threshold will indicate "contact" or "no contact."

Figure 8A:
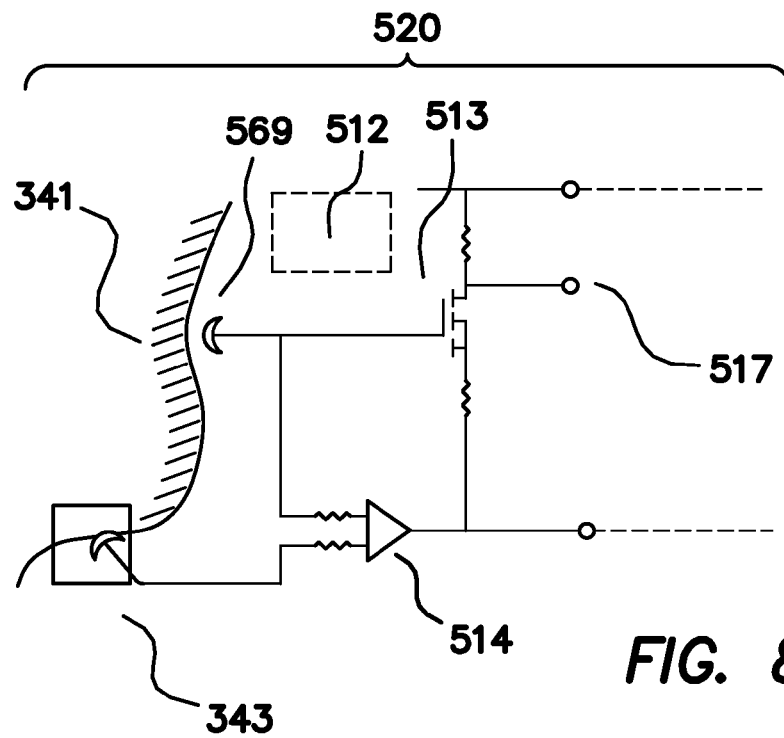
FIG. 8A is an illustration of a typical biopotential signal at the membrane.

FIG. 8A is an illustration of a typical biopotential signal at membrane 516 (signal IN) which is further clarified by observing the isolated MOSFET circuit M1 513 biases the input signal obtained through capacitor C1 523, and normalizes it to a output average signal level at VOUT such that the differentially measured signal output displays the AC and pulse components of the external bioelectric signal. The biopotential signals occurs between the two isolated MOSFET junctions designated by module 520, and potential difference (voltage) due to cell membranes permeability to K+' Cl–, Na+' resulting in variation of cellular potential with time, and it is the action potential, measured by the module 520, and the array of sensors designated as multi-channel sensors 500.

The electrodes in the prior art are typically made of metal-electrolyte interface. The interface impedance in this relation is represented as a capacitor, and in a non-polarized electrode, the impedance is represented as a resistor. But in practice both capacitive and resistive components are present in the existing art, while the current method and the accompanying apparatus to this invention employ the MOSFET isolated junction, which measure the action potentials without the parasitic capacitive or resistive loads noted by the prior art.

The figure further illustrates the embodiment of an integrated MOSFET sensor platform 520, including a biopotential detection module with output 518, pressure transducer 515 with sensing plate 516 and temperature sensor 521. The integrated sensory elements are designated as system 500. The system consists of eight channels of sensing modules 520, located along a flexible circuit board. The basic electrostatic field sensing is performed by a depletion mode field effect transistor, MOSFET, 513 in each channel. The sensor plate 516, facing the tissue 341, for each MOSFET is connected to the high impedance gate of the MOSFET which amplifies the potential variations of the tissue sensed through the insulating gap between the tissue 341 and the plate 516. The potential variations being the contact surface area between the sensor plate 516 and the tissue 341. One of the channels is used as the reference sensor 512. The average potential of the reference sensor plate 569 at this location is regulated to be close to zero in reference to a proximally placed single connection to the measured tissue 343. The voltage difference between the reference plate and the single tissue connection is measured by a high input impedance differential amplifier 514, the output of which sets the common potential for all cannels. The high impedance differential inputs to amplifier 514 reduces any conductive current below about <10~9 Amps. As a result, charge transfer is minimized. The regulated common, the auxiliary power connection (+VCC) and the reference 512 voltages are floating with the potential of sensor plate 516, all of which is now practically at zero potential relative to the facing the tissue 341. The potential difference between the reference plate 569 and the regulated common is representative of the double layer potentials and the tissue impedances between plates 516 and 569. Once regulated by differential amplifier 514 and under steady state conditions, there are no charge currents flowing between these sensing points due to the measuring procedure itself. However, during maintained monitoring, periodic variations due to blood pressure or muscle contractions modulate the common potential at the output of amplifier 514. The associated periodic charge variations average to zero. However, the absolute values of the slope-variations (derivatives) of the instantaneous common potential are mainly the function of the impedance variation between 516 and 569 sensing spots. Thus, an average can be extracted and used as the impedance reference for the other sensing channels. Relative impedance variation is then computed from the ratio of sum of the average of Output B 518 voltages divided by the reference uutput voltage and multiplied by the impedance coefficient computed from the slope average.

Figure 9:
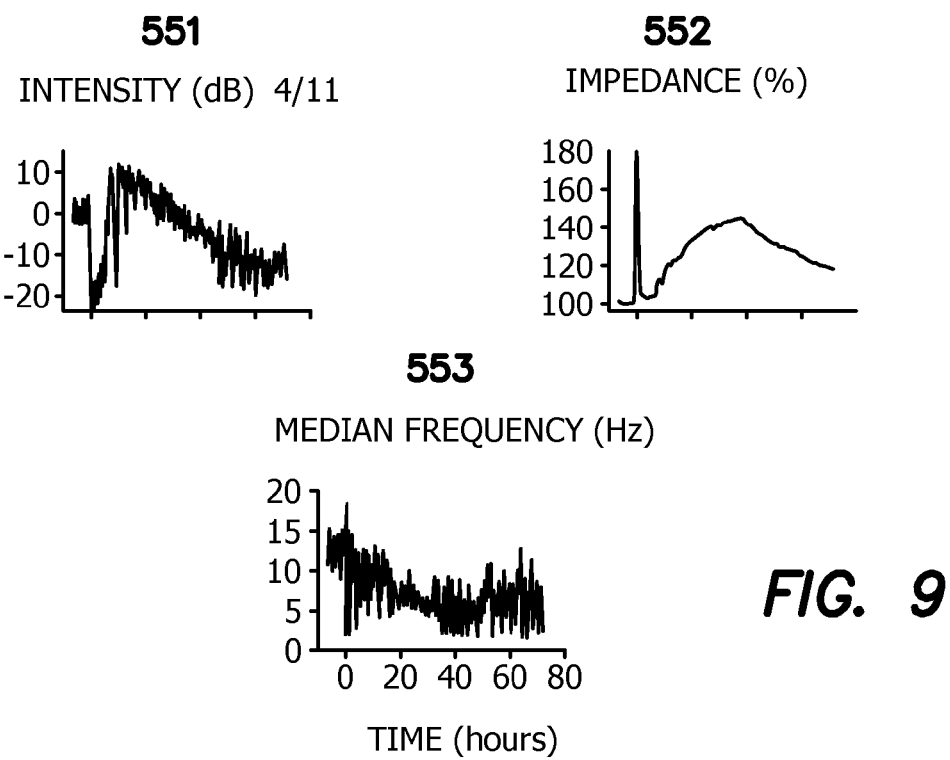
FIG. 9 is an example of a graphic display of a typical long term EEG signal recording with the corresponding Impedance and frequency-domain diagrams.

FIG. 9 is an example of a graphic display of a typical long term EEG signal recording with the corresponding impedance and frequency-domain diagrams. The impedance diagram is obtained from the measurement technique detailed by employing the MOSFET sensor array. The EEG signal is defined by the dB scale and the impedance display is in percentage for showing relative trends over time. The impedance calculation derived from the equation $$E_d = \frac{\rho_v \cdot d^3}{3 \cdot \varepsilon} - \frac{\rho_v \cdot d^2 \cdot d_0}{2 \cdot \varepsilon} + \frac{\rho_v \cdot d_0^3}{12 \cdot \varepsilon} \,[\text{V/m}] \quad d \geq d_0.$$

Figure 9A:
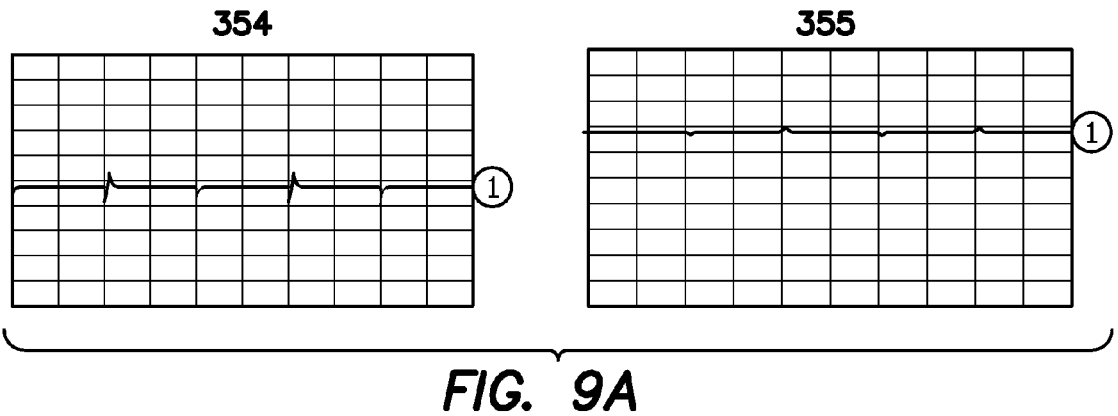
FIG. 9A is a graph which depicts the bioelectric potential signal as a function of amplitude vs. time.

FIG. 9A is a graph which depicts the bioelectric potential signal as a function of amplitude versus time. The output from the biopotential at the tissue contacts between membrane 516, and the MOSFET 513 is received by output channel B 518. Each module 520 has three outputs. Output B and Output A are the bioelectric signal 518 and pressure signals 517, respectively. The third output is the temperature measurement signal 519. These outputs are analog signals. Each of these signals is converted into 16 bit data packets of digitalized information via an ADC 501, which then are serially transmitted to the microcontroller 536. It is to be expressly understood that any number of bits could be used for the data packets depending on the system architecture without departing from the original spirit and scope of the invention.

FIG. 9A is a graph which represents the DC level following the pressure level changes of the pressure transducer 515. The membrane 516 which forms the outer layer of the transducer acts as a surface and any displacement of 516 varies the resistance at the output channel 517. This signal is extracted by putting the MOSFET output signal through a low pass filter consisting of resistor 529 and capacitor 531.

Figure 9B:
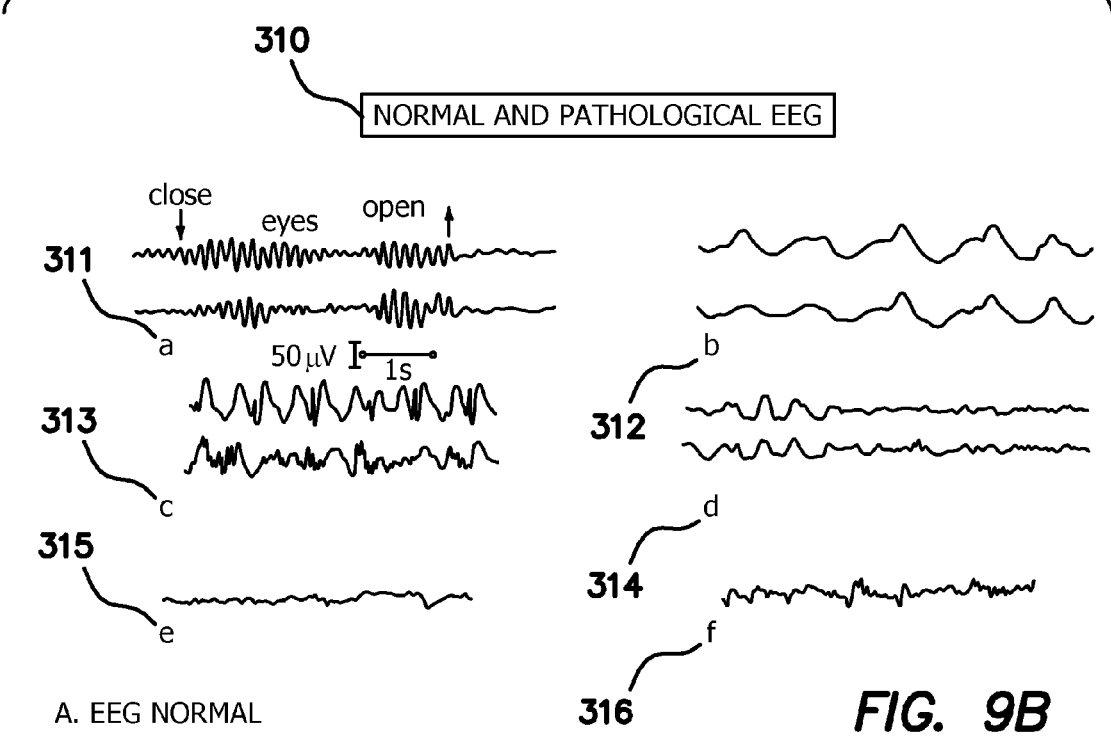
FIG. 9B is a graphical representation which depicts various brain waves.

FIG. 9B is a graphical representation which depicts various brain waves typical of rhythms, powers, or amplitude corresponding to occurrences which the presently described method is capable of identifying and isolating due to the ability of the MOSFET and its use of High Electron Mobility Transistor 555 to sense the small biopotential within the anatomical environment of brain electrical activity and by analogy, to such activity within the arterial structure of the renal artery. The mapping and ablation catheter described herein is capable of collecting, sampling and measuring the power and amplitude of the signal generated by the renal artery plexus while dynamically traveling through the vascular tree. An example of such biopotential measurements are noted when comparing normal brain wave activities versus abnormal behavior associated with increased pressure or due to pathological inducement. Panel (a) 311 corresponds to normal (under no specific conditions) electroencephalogram brain wave reading. The leftmost signal corresponds to atypical beta band waves when the person has his eyes closed. The center wave corresponds to the change in rhythm when the eyes are open, and so forth. Panel (b) 312 suggests a similar wave pattern of a person under a different task, stereotypically of 'default mode' activity that could arise in the temporal or frontal lobes under EEG readings. Panel (c) 313 corresponds to the same subject as panel (b) 312 while the person is having an epileptic seizure. The rhythms become more pronounced, with rapid ripples and increased synchronicity on the envelope of the prior wave bands. In one embodiment, the system 500 enables the physician to discern and identify these changes in power. The system 600 alerts the physician (using AI routines) on the potential seizure occurrence. Panel (d) 314 is suggestive of an unconscious person's EEG reading. The decreased power, yet stable rhythm, is suggestive of a loss of consciousness that can be alerted by use of the alert notices. Panel (e) 315 indicates the EEG reading of a lesion brain region, suggestive of the immediate effect of permanent pressure on the arterial structure or tissue 341, reflected by the sensor array reading and is identified ad-hoc by the system 600. Panel (f) 316 graphically represents the effect of overpressure such as indicated by mean arterial pressure minus the catheter surface with its MOSFET sensor array 500 pressure producing a state whereby the differential pressure is less than 70 mm Hg (<70 mm Hg) so as to generate a typical wave reading as indicated. A patient undergoing pressure of 550 mm of water shows increased wave amplitudes in the sensor array 500 indicator reading, as well as short ripples suggestive of a burst of evoked potential in the area of where the catheter is exerting its pressure. Qualitative indications of the relationship between the etiological and mechanical state of the cellular structure under pressure and its electrical nerve activity are indicated. As a reference we show below the continuous reading of the same area when no pressure is applied. Notice the similarity between over-pressured arterial region under the catheter 800 in panel (f) 316 and the permanently lesion one in panel (e) 315. All of these cases are identified and isolated by the presently described system further producing the necessary alerts indication in a form of visuals or audio notices so as to enable the operator performing the procedure that its applied axial and/or radial surface contact with the arterial branch is adequate for measuring or for delivering energy for curative purpose.

Figure 9C:
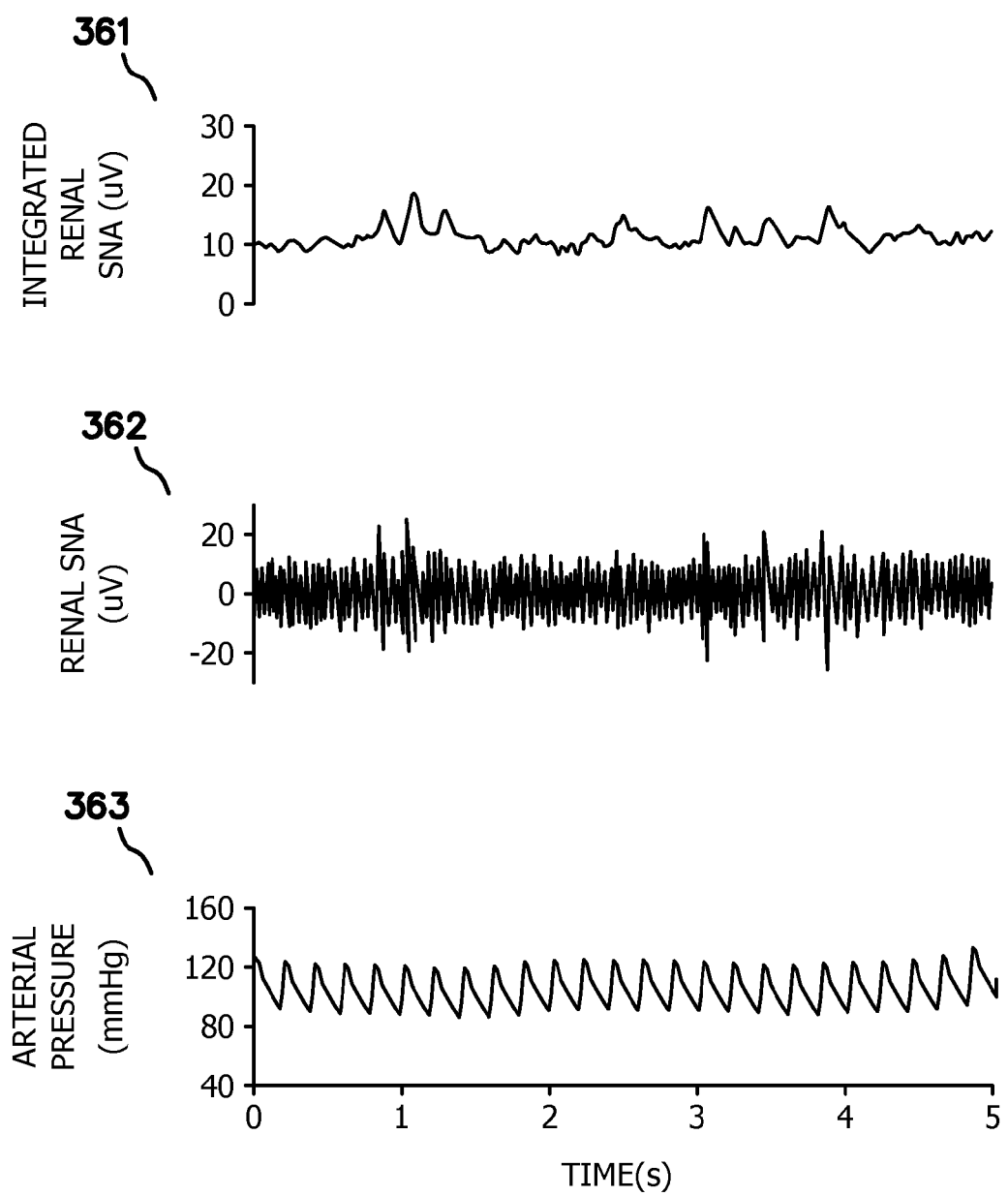
FIG. 9C is an example of a graphic display of an integrated renal SNA, renal SNA, and arterial pressure.

FIG. 9C is a graphical representation of a signal generated by a study using animals, which demonstrates the complexity of collecting bioelectrical potential signal data from ganglionic and nerve endings associated with the sympathetic nervous system (SNA). The ensuing figures, cited from Guild et al. in the study "Quantifying sympathetic nerve activity: problems, pitfalls, and the need for standardization," published in Experimental Physiology (95.1, pp. 41-50), describes "the common ways of describing SNA . . . [Assessments of] the quality of SNA are made, including the use of arterial pressure wave-triggered averages and nasopharyngeal stimuli. Calculation of the zero level of the SNA signal from recordings during ganglionic blockade, the average level between bursts and the minimum of arterial pressure wave-triggered averages are compared and shown to be equivalent." The paper further recommends that the scale of measurement of neural and ganglionic activity in various plexuses must be set at the scale of microvolts and, as shown by the figures presented, the renal artery and the baroreceptor measurements represent a difference of ±10 µV with a resolution of ≥1.45 µV.

Figure 9D:
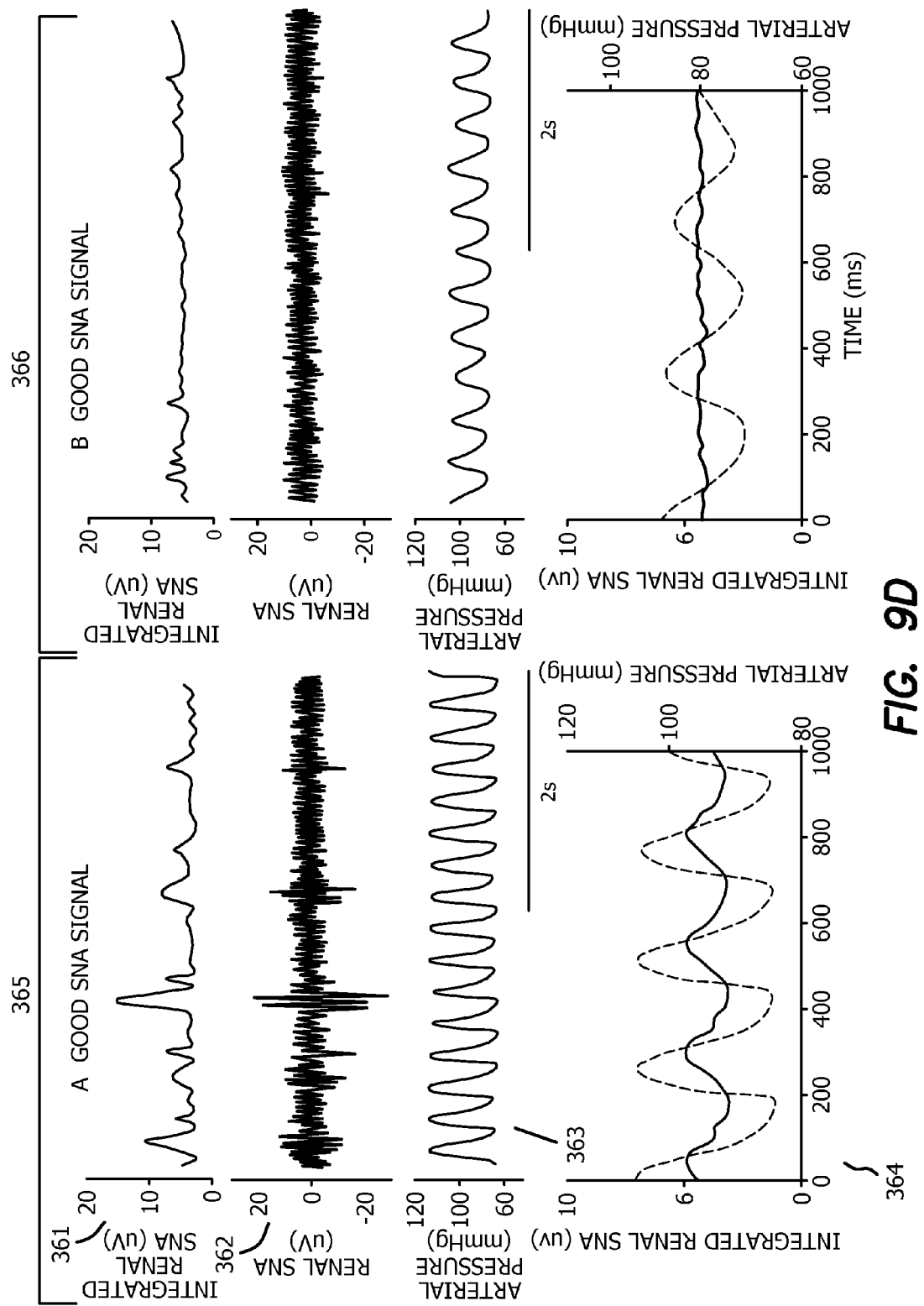
FIG. 9D is an example of a graphic display of Short recordings of integrated renal SNA, renal SNA (often termed raw SNA) and arterial pressure, along with systolic pressure-triggered averaged records of arterial pressure and renal SNA.

FIG. 9D is an example of a graphical display of short recordings of 4 s of an integrated renal SNA 361, renal SNA (often termed raw SNA) 362, and arterial pressure 363, along with systolic pressure, triggered averaged records of arterial pressure, and renal SNA.

The study noted above, and many others, describes the effects of far-field influence on local measurements of ganglionic bioelectric potential due to the onslaught of systolic wave as well as respiration. In various studies, the author (i.e., Guild) indicates that the triggered averaged records of arterial pressure and renal SNA must be filtered from one another so as to enable the termination of the fidelity of the signal. Separation of the original renal SNA signal from both the integrated renal SNA and from the arterial pressure is essential for proper control of the data received from the renal artery, for example, or for any ganglionic due to the fact that any former description that describes the signal fidelity must assume the leaky integrator as a proper representation of the biological phenomena it emulates, where the formal expression of a leaky integrator describes the fact that a decaying signal tends to integrate with other sources of potential as they coalesce and represent itself as an "average." The reality is that the electrocardiogram signal with its systolic wave onslaught substantially contributes to the formation of the average reading, as this signal is measured in millivolts while most of the activity of SNA and ganglionic response is measured in microvolts.

The solution proposed using the MOSFET sensor array 500 to detect local bioelectric potential will enable the differentiation of the original renal SNA signal from the influence exerted by this phenomenon.

In a "good" sympathetic recording, where bursts can be seen in the filtered original SNA signal and in the integrated SNA data, the systolic wave-triggered averages show a distinct phasic relationship between arterial pressure and the renal SNA (Malpas et al., 2006). FIG. 9D further describes and compares the filtered original SNA signal with a signal where the differentiation between the integrated renal SNA and the "pure" renal SNA signals are displayed and where the averages generated by a poor collection of unfiltered data result in averages which distort dramatically the signal characteristics, i.e., amplitude, frequency, and phase. The paper further reports that sometimes SNA recordings appear to contain ECG information, which can be identified by distinct sharp spikes in both the raw and integrated SNA signals. When these signals are examined as systolic wave-triggered averages, the SNA shows much sharper peaks than a typical "good" SNA signal 365.

Figure 9E:
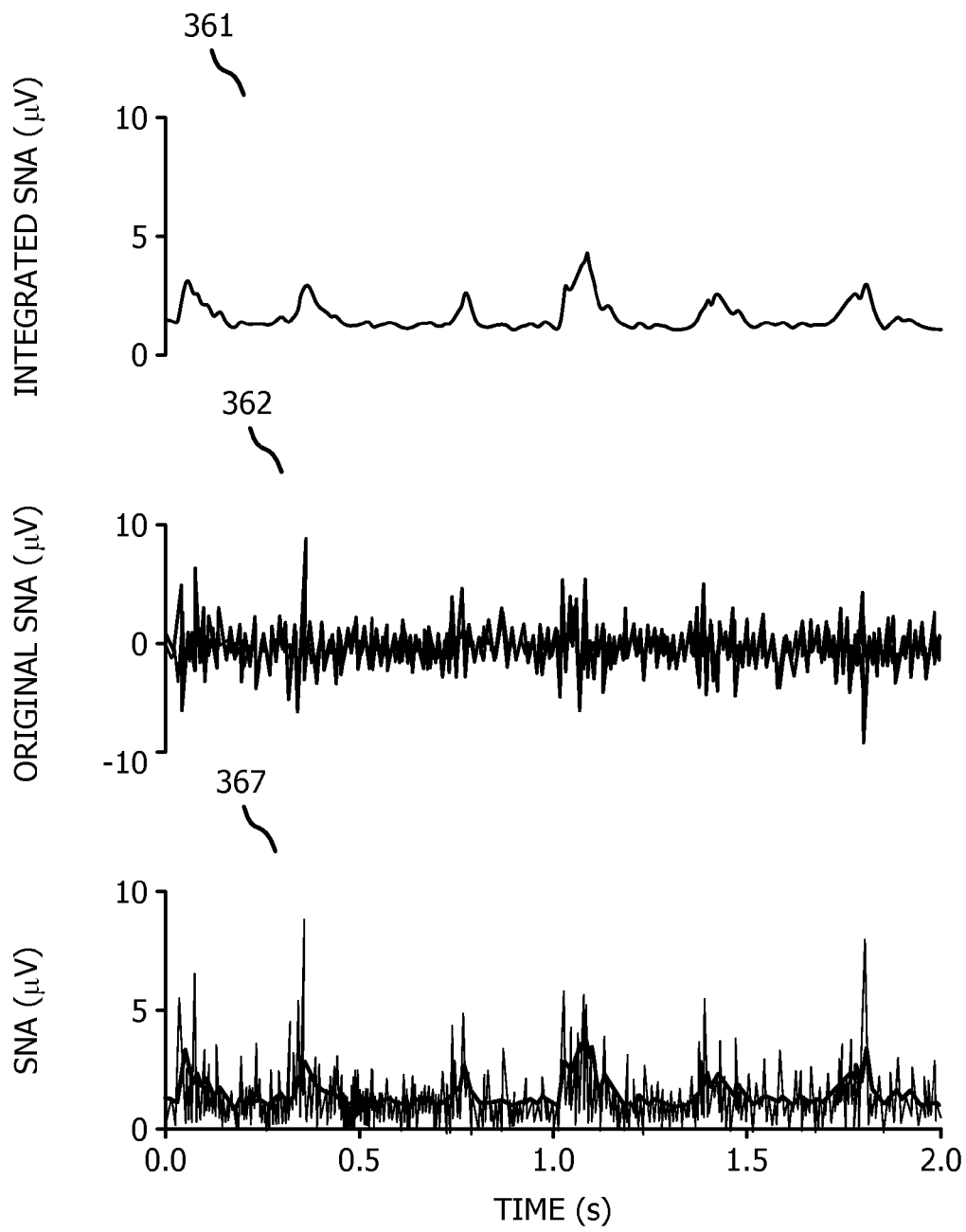
FIG. 9E is an example of a graphic display's recordings of Short (2 s) example of renal SNA from a rabbit, showing the integrated SNA, original SNA and that the integrated SNA overlays the rectified original SNA signal.

FIG. 9E is an example of a graphic display's recordings of a short (2-second) example of renal SNA showing the integrated SNA 361, original SNA 362, and that the integrated SNA (shown as the black graph shown in the bottommost graph above) overlays the rectified original SNA signal (shown as the grey graph in the bottommost graph above 367). As clearly exemplified by the figure, the use of electrode technology to identify the SNA signal and differentiate it from the ECG, electromagnetogam, and various electrical noises generated by various biological centers of control, we must find the common mode rejection to enable the collection of high-fidelity ganglionic signal.

In another embodiment of the invention, a MOSFET transistorized pad lying on the surface of a biological tissue is better suited to depict signal on the order of 1-5 µV without the distortion associated with the systolic wave emanating from the left ventricle during the cardiac cycle.

In another embodiment of the invention, one skilled in the art will continue to employ the common approach which is used to verify SNA recordings and measure the background noise level, which is to administer a short-acting ganglionic blocker. It is further known to those familiar with the art that the most common approach to recording SNA is to apply bandpass filters with a high pass around 50 Hz and a low pass of 1-5 kHz. By calibrating the amplifier, one can calculate the microvolt level of each discharge. However, because the signal displays positive and negative voltage changes centered about zero, the average level over time will be zero. To allow calculation of the overall level of SNA, either the individual spikes must be identified and counted or, more commonly, the signal is rectified and integrated. In addition, the literature recommends the use of a "leaky integrator" with a 20 ms time constant (Malpas & Ninomiya, 1992a), which serves as a low-pass filter.

Additionally, FIG. 9E indicates that the amplitude and frequency variations between bursts are clearly visible, and can serve as a measure for selecting the proper low-pass and high-pass filters by detecting the integrated signal using either a threshold voltage or a rate of rise of the voltage, or often a mixture of the two (Malpas & Ninomiya, 1992a; McAllen & Malpas, 1997).

As shown by FIGS. 9-9E and by the design of the MOSFET sensor array 500, we conduct the measurements as a bipolar measurement with a differential output so as to enable nerve preamplifiers to be represented in a differential mode so as to amplify the difference in the signals registered at the transistorized pads and enable the rejection of extraneous signals (e.g., from ECG and baroreceptors).

The invention presented herein provides for local versus far-field signal, ground potential on-site (within the transistorized pad), and fast-acting variable resistors based on MOSFET technology.

FIG. 10 is an orthographic representation of the MOSFET sensor array 500 depicted on the catheter assembly 800. The catheter assembly 800 comprises of an ablation-tip 821, an irrigation nozzle 824, at least one electrode 826 (a configuration that optionally includes a unipolar, bipolar, or Quadra polar configuration), a sensor manifold 829, a set of MOSFET sensors 513, and wires as defined by the schematic diagram noted by the figures and their accompanying descriptions. The configuration of MOSFET sensors 513 in FIG. 10 contains eight sensors, but this is meant to be for illustrative purposes only. Any optional number of the sensors within the assembly is possible without departing from the original spirit and scope of the invention.

FIG. 10 further describes a cross sectional view of the proposed mechanical layout of the catheter assembly 800 where the distal end of the assembly is an ablation tip 821 with an embedded thermistor 822, a permanent magnet 823 (NdFeB), a cross section of the irrigation nozzle 824, a set of an articulated permanent magnetic beads 825 form out of chemistry noted by NdFeB composition, an irrigation tube 828 and electrodes 826.

Figure 10A:
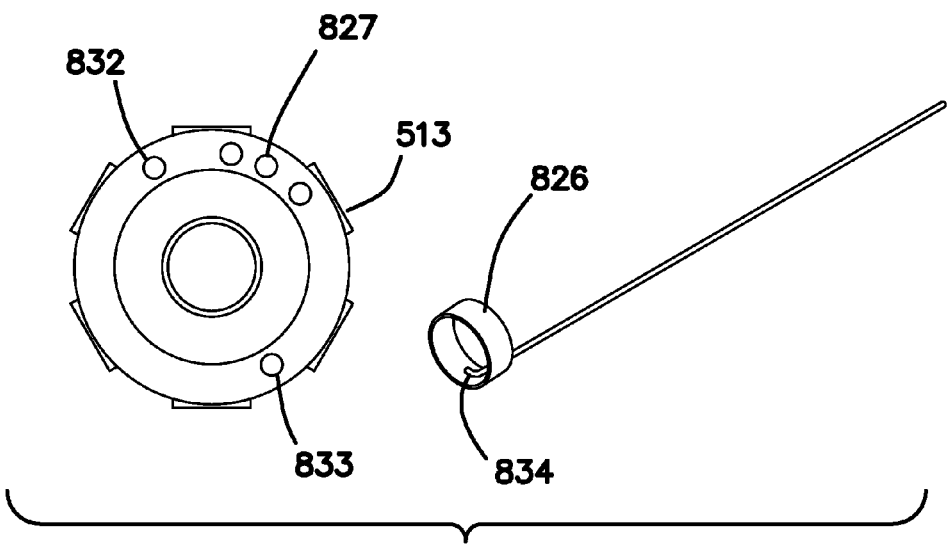
FIG. 10A is a cross-sectional view of the catheter assembly, depicting the geometrical layout of the catheter construction.

FIG. 10A is a cross-sectional view of the catheter assembly 800, depicting one embodiment of the geometrical layout of the catheter construction. The catheter 800 comprises a dimension of 7 Fr., so as to render the realistic proportions of the elements forming the embodiments of this invention. The geometry comprises of an irrigation tube 828, formed in the center of a permanent magnet (NdFeB) 825, supported by manifold 829 which holds the MOSFET sensors 513, conductors and electrode wires, and a thermistor 822. The figure further depicts an example of electrode which might assume the configuration of a unipolar, bi-polar, Quadra-polar or N-polar configurations.

FIG. 11 is an isometric layout of the proposed catheter 800 comprising ablation tip 821 with thermocouple 822 (not shown for clarity), irrigation manifold 824, articulated permanent magnet 823, electrodes 826, irrigation tube 828, sensor manifold 829, and an array of MOSFET sensors 513. The architecture of the mapping and ablation catheter 800 enables the operator to magnetically manipulate the distal end of the catheter to its desired position (DP) 172 by pushing, pulling, translating, and rotating the catheter to its destination by the use of the electromagnetic field generated by the CGCI S-system 100. The catheter 800 is fitted with an irrigation tube 828 and an ablation tip 821 to enable the operator 391 to deliver RF-energy to the desired site. For renal denervation procedures, the catheter will travel from the aortic branch to the renal artery by the use of the magnetic force so as to achieve its DP 172 at the renal artery plexus 345 while the operator 391 fixes the position of the catheter tip 821 and deliver 8-10 Watts of RF-energy for 120 seconds or any amount of energy as determined appropriate by the operator 391 so as to achieve isolation of the sympathetic nerve ending as it is configured by the renal ganglionic plexus. Further, the catheter 800 is fitted with an array of MOSFET sensors 513 such as known in the art as heterogeneous FET junctions or high electron mobility transistors 555 layered over the manifold 829.

Figure 12:
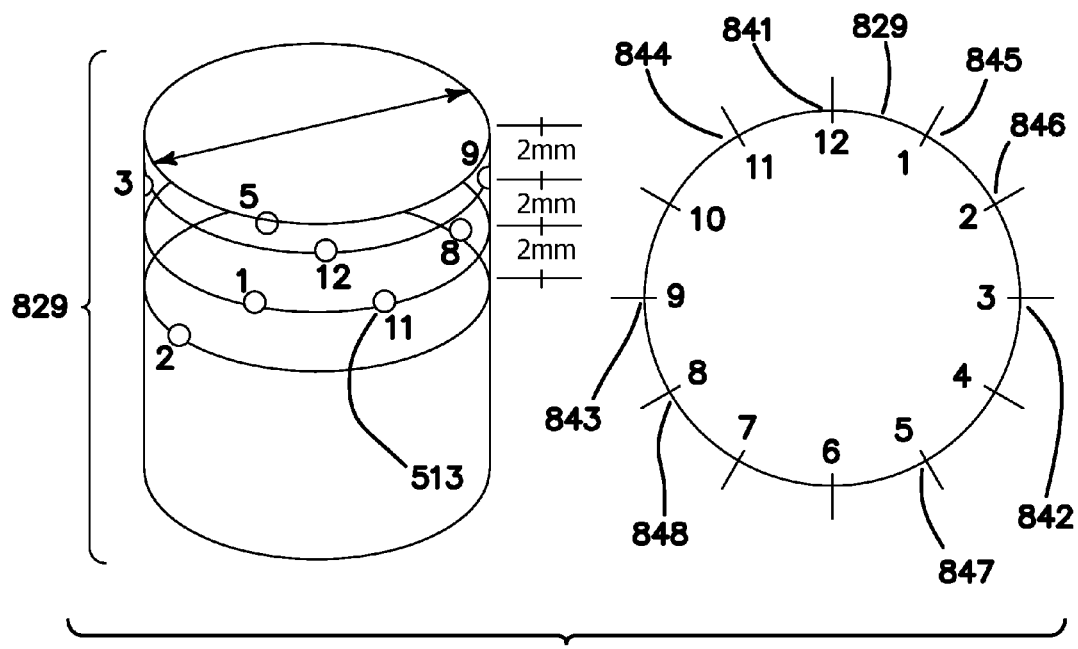
FIG. 12 is an orthographic representation of the embodiments of the MOSFET sensor array architecture and a geometrical layout of the MOSFET sensor.

FIG. 12 is an orthographic representation of the embodiments of the MOSFET sensor array 500 architecture where a geometrical layout of the MOSFET sensor 513, for example, is distributed in accordance with the principle of clocking and synchronization so as to provide for orientation in logical displacement. The spatial location of the sensors provide the system 600 with global synchronization of the sensor network applications that require precise mapping of the collected sensor data with the time of the events relative to the proximity of the sensor to the tissue surface, while providing a clear indication for sensor output which are not in contact with the tissue. The geometrical location and distribution of the sensor on the manifold 829 enables the system reporting to physically distinguish between near and far fields and further reduce the averaging error associated with the electrode technology. The embodiment of tracking and surveillance of bioelectric signals generated by ganglionic plexus signal coordinates are true to its indication without further manipulation by means of algorithmic separation and filtering as it is based on a node-based approach, a hierarchical cluster based method, and a fully localized diffusion-based method. Many emerging sensor network applications require that the sensors in the network agree on the time. A global clock in a sensor system will help process and analyze the data correctly and predict future system behavior by matching the sensor location and sensing time, the sensor system may predict the catheter moving direction and speed. Without a global agreement on time, the data from different sensors cannot be matched up. Navigation guidance and any other application that requires the coordination of locally sensed data and mobility is benefiting from such distribution of the sensors. Clock synchronization may also help to conserve energy in a sensor network, by allowing a coordinated way to set nodes into sleeping mode.

FIG. 12 further depicts the geometrical layout of the sensor array on manifold 829. The geometry of the manifold is divided into three (3) planes such that planes A, B, and C define the location of the MOSFET sensors 513 with clocking of the first sensor 841 relative to the watch dial where the 12 o'clock position acts as the imaginary center line of the manifold 829. Further stipulated is that between any two successive sensors on the same plane—A, B, or C—the sensor is separated by 90° between each successive sensor. For the purpose of illustration of the embodiment and if we assume a 7 Fr scale where the diameter is 2.45 mm resulting in an arc section of 1.924 mm of the circumference on plane A.

The arrangement results in locating the first sensor 841 at 12 o'clock, the second sensor 842 at 3 o'clock, and the third sensor 843 at 9 o'clock. FIG. 12 further describes the location of the fourth sensor 844 on plane B, with 2 mm separation between any two successive planes. This arrangement results in locating the fourth sensor 844 at 11 o'clock and the fifth sensor 845 at 1 o'clock on plane B. On plane C, sensors would be located as follows: the sixth sensor 846 at 2 o'clock, the seventh sensor 847 at 5 o'clock, and the eighth sensor 848 at 8 o'clock.

To further describe the illustration employing a 7 Fr catheter, the following definition will apply. The distal-most surface is closest to the 12 o'clock ring-sensor—i.e., sensor 12 is 2 mm down the length of the MOSFET sensors assembly 513 on the first ring and is defined as the zero point. Then, traversing from the distal end to the proximal end: the third sensor 843 is 2 mm down and 90° clockwise (+1.924 mm) on the first ring; a ninth sensor is 2 mm down and 90° counterclockwise (−1.924 mm) on the first ring; sensor 1 is 4 mm down and 30° clockwise (+0.6414 mm) on the second ring; sensor 11 is 4 mm down and 30° counterclockwise (−0.6414 mm) on the second ring; sensor 2 is 6 mm down and 60° clockwise (+1.283 mm) on the third ring; sensor 5 is 6 mm down and 150° clockwise (+3.207 mm) on the third ring; and sensor 8 is 6 mm down and 120° clockwise (−2.565 mm) on the third ring.

The use of the MOSFET sensor array 520 and used in combination with the guidance control provided by the CGCI apparatus 100. The combination of guidance control and detection of the apparatus, provide for precision, accuracy, and safety.

Figure 13:
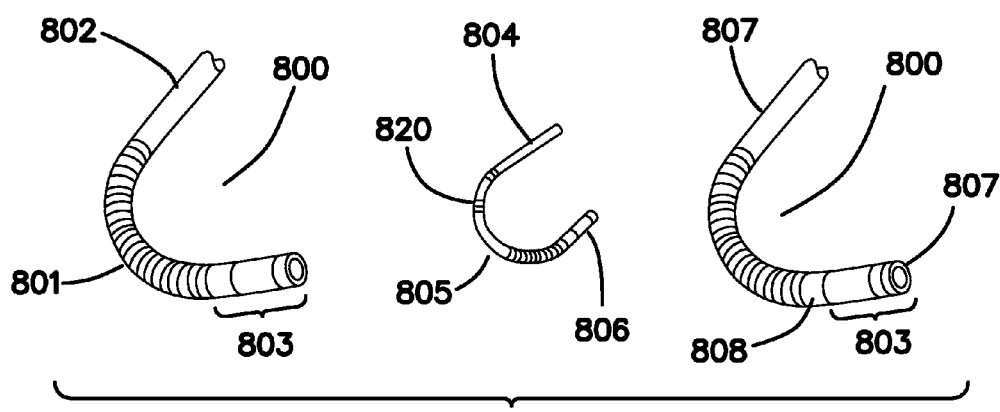
FIG. 13 is a series of perspective views of a catheter assembly and guidewire, fitted with a magnetic pallet for use with the CGCI System.

FIG. 13 is a series of perspective views of the catheter assembly 800. FIG. 13 illustrates the location of the magnetic element embedded within the catheter shaft which enables the apparatus 100 to push, pull, rotate, and advance the catheter 800 to its desired location based on operator command generated by the joystick 118 and a guidewire assembly 820 used with the GCI system 100. The catheter assembly 800 is a tubular tool that includes a catheter body 807 which extends into a flexible section 801 that possesses increased flexibility for allowing a more rigid responsive magnetic tip 803 to be accurately steered through a torturous path. The magnetic catheter assembly 800 in combination with the GCI apparatus 100 reduces or eliminates the need for the plethora of shapes normally needed to perform diagnostic and therapeutic procedures. This is due to the fact that during a conventional catheterization procedure the surgeon often encounters difficulty in guiding a conventional catheter to the desired position, since the process is labor intensive and relies on manual dexterity to maneuver the catheter through a tortuous path of, for example, the retroperitoneal location of the kidney, increases the technical difficulty of access to the nerves. In spite of these many obstacles, recent developments of magnetically guided procedure such as noted by the apparatus titled CGCI 100 appear to have the potential to overcome these anatomic and technical difficulties and to provide new hope for the treatment of resistant hypertension and perhaps other clinical conditions commonly associated with increased renal sympathetic nerve activity. Thus, the use of a plethora of catheters in varying sizes and shapes are made available to the surgeon in order to assist him/her in the task are eliminated by the use of the catheter 800, since such tasks require different bends in different situations due to natural anatomical variations within and between patients we devised a comprehensive solution to navigation within the arterial tree by using the CGCI apparatus 100, where only a single catheter is needed for most, if not all patients, because the catheterization procedure is now achieved with the help of an electromagnetic system that guides the catheter 800 and guidewire assembly 820 to the desired position within the patient's body 390 as dictated by the surgeon's manipulation of the virtual tip 105, without relying on the surgeon pushing the catheter quasi-blindly into the patient's body 390. The magnetic catheter 800 and guidewire assembly 820 provides the flexibility needed to overcome tortuous paths.

The guidewire assembly 820 includes guidewire body 804 and a flexible section 805, which possesses increased flexibility for allowing a more rigid responsive tip 806 to be accurately steered around sharp bends so as to navigate a torturous path. The responsive tips 803 and 806 of both the catheter assembly 800 and the guidewire assembly 820 respectively, include magnetic elements such as permanent magnets. The tips 803 and 806 include permanent magnets that respond to the external flux generated by the electromagnetic cluster. The tip 803 of the catheter assembly 800 is tubular, and the responsive tip 806 of the guidewire assembly 820 is a solid cylinder. The responsive tip 806 of the catheter assembly 800 is a dipole with longitudinal polar orientation created by the two ends of the magnetic element positioned longitudinally within it. The responsive tip 806 of guidewire assembly 820 is a dipole with longitudinal polar orientation created by the two ends of the magnetic element 803 positioned longitudinally within it. These longitudinal dipoles allow the manipulation of both responsive tips 803 and 806 with the CGCI apparatus 100, as the upper electromagnetic cluster will act on the tips 803 and 806 and "drag" them in unison to a desired position as dictated by the operator.

Figure 14:
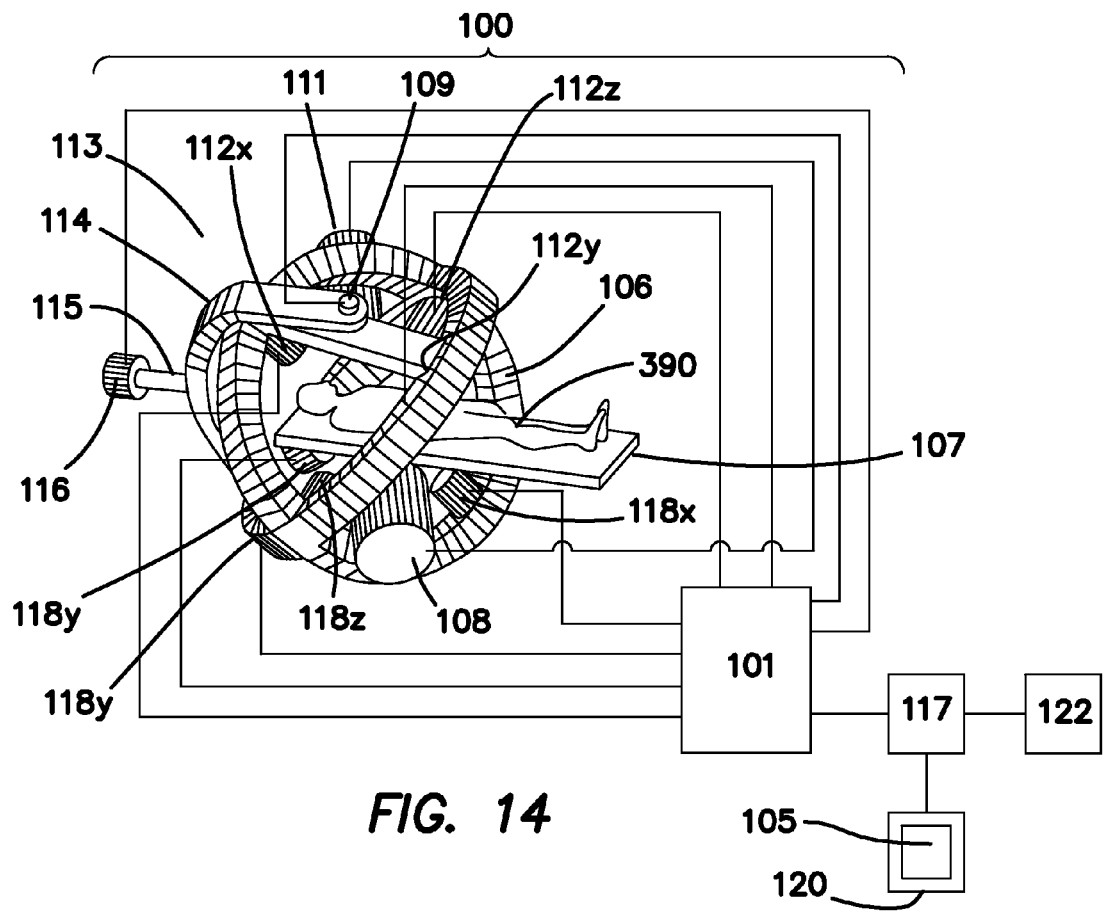
FIG. 14 is an isometric representation of the remote magnetic navigation apparatus, referred to as the CGCI system.

FIG. 14 is an isometric representation of the remote magnetic navigation unit, also referred to as the CGCI 100. FIG. 14 shows the arrangement of electromagnetic coils which are geometrically arranged as noted by the reference designators; 112X, 112Y, 112Z, 118X, 118Y, and 118Z in a polar configuration, 113 and the geometry is further supplemented with additional two coils 112$^{xz}$ and 112$^{yz}$ enabling a fields radiation pattern of mixed fields. The above geometrical configuration illustrates the use the CGCI apparatus 100 with an alternate magnet system using a bi-plane support mechanism to facilitate the return of stray magnetic field to the circuit. The geometry increase the magnetic chamber efficiency and comfy the magnetic fields radiation to the chamber perimeter, hence eliminating the needs to shield the room form the strong magnetic fields and its unnecessary harmful interference with other auxiliary medical electronic devices located within the operating room. FIG. 14 further illustrates the overall relationship between the elements comprising the CGCI apparatus 100, which includes an operating table 107 and the patient 390.

The geometrical layout of the CCGI 100, configured as polar configuration where the axial radiation pattern of (+) x to (−) x is superimposed with a z axis component so as to enable a gradient along the desired vector. The additional translational force along the axis of the catheter movements, is due to additional coils 112$^{xz}$ 112$^{yz}$ radiation geometry 113, providing the CCGI chamber with a mixed magnetic field and is contrasted with a symmetric approach where the electromagnets 112X through 118Z are configured as part of a toroid in a cluster that its topological spherical manifold enable a computational symmetry within the effective magnetic area.

The polar configuration reduces the complexity of regulating the magnetic field and its gradient. The topological selection of a spherical chamber with coils located in a polar geometry is resulting in a linear (additive) representation of the vector field by superposition of the magnetic flux density along the great axis of the permanent magnetic tip 823 on or within the distal end of the catheter or medical tool(s). The CGCI 100 with its algorithm is detailed by U.S. Pat. No. 7,769,427, which is incorporated herein in its entirety. The CGCI 100 solves the problem noted by the prior art by providing a remote robotic maneuvering of a catheter or medical tool to freely rotate and translate it within the vascular tree and/or body cavity for the purpose of diagnostic or therapeutic procedure and with ease and safety which improve the current art of manual or mechanical means.

The architecture shown in FIG. 14 is advantageous as the strength of the electromagnetic field B increases towards the center line of the gap, and the gradient peaks at the edge of the gap, enabling the CGCI 100 to form a lobed magnetic field structure which is not as easily obtainable by the use of the bi-plane axio-symmetric layout noted in FIG. 14. The CGCI 100 incorporates such an arrangement so as to provide the benefits of pushing, pulling, and guiding the magnetically coupled catheter tip 803 in a polar configuration.

Figure 15:
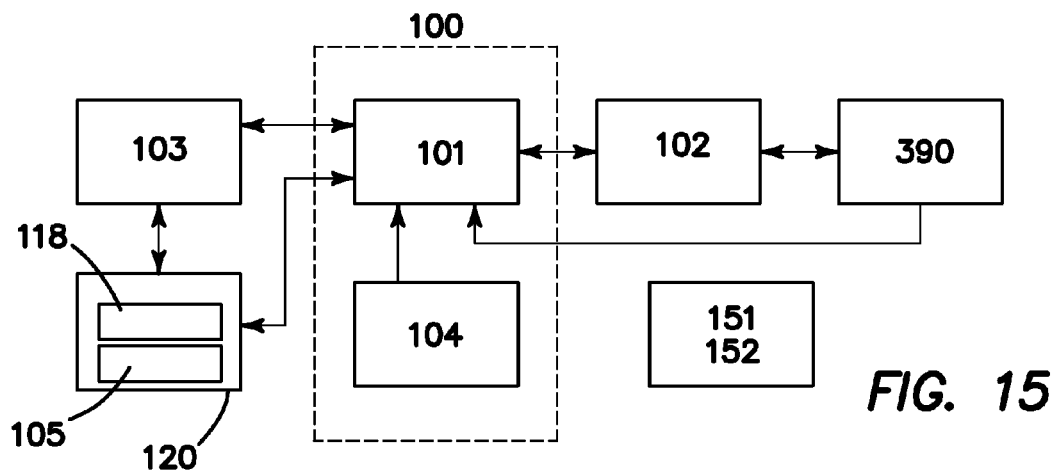
FIG. 15 is a system block diagram for a surgery CGCI System that includes an operator interface.

FIG. 15 is a system block diagram for a surgery system that includes an operator interface 103, the Catheter Guidance and Imaging (CGCI) system 100, surgical equipment 102 (e.g., a catheter tip 821 with MOSFET sensor array 500, irrigation pump 151, and energy delivery generator 152), one or more user input devices 120, and a patient 390. The user input devices 120 can include one or more of a joystick 118, a mouse, a keyboard, a Virtual Tip 105, and other devices to allow the surgeon to provide command inputs to control the motion and orientation of the catheter tip 821 so as to identify the location of interest such as the renal sensory afferent nerves, using the MOSFET sensor array 500. The CGCI system 100 includes a controller 101 and an imaging and synchronization module 104 known as a CARTO JJ BioSense Webster or EnSite of St. Jude Medical.

FIG. 15 further illustrates the overall relation between the various functional units and the operator interface 103, the auxiliary equipment 102, and the patient 390. In one embodiment, the CGCI System Controller 101 calculates the Actual Tip (AT) position of a distal end of a catheter as further described in the text in connection with FIG. 15A below. Using data from the virtual tip (VT) 105 and the imaging and synchronization module 104, the CGCI system controller 101 determines the position error, which is the difference between the actual tip position (AP) and the Desired tip Position (DP). In one embodiment, the controller 101 controls electromagnets to move the catheter tip in a direction selected to minimize the position error. In one embodiment, the CGCI system 100 provides tactile feedback to the operator by providing force-feedback to the VT 105, as described in connection the following figures and specification.

Figure 15A:
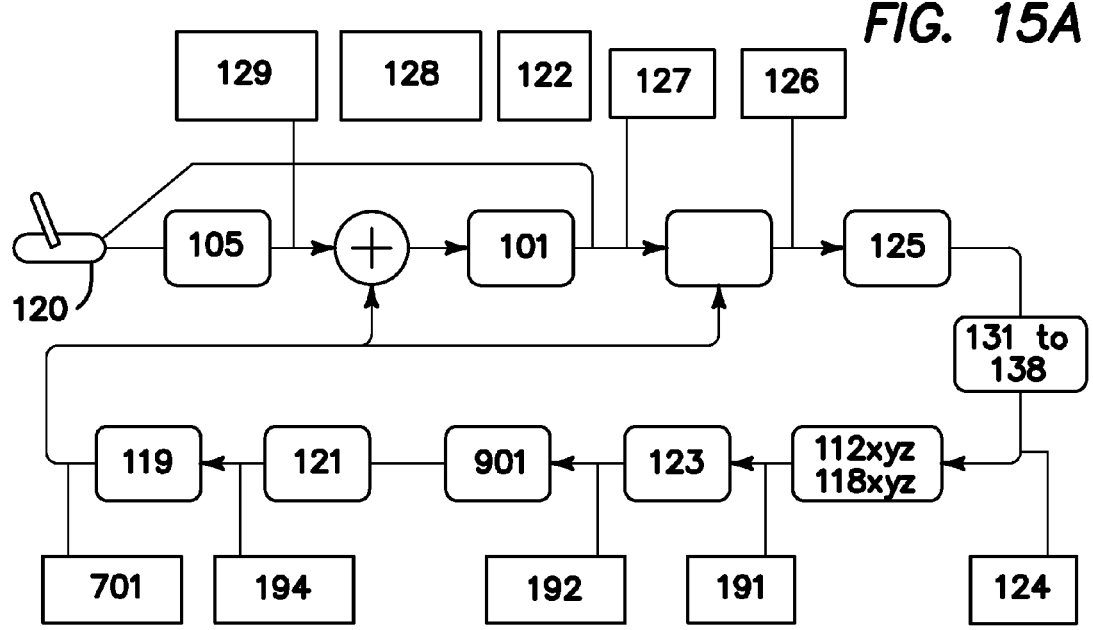
FIG. 15A is a system block diagram which further describes the operation of the CGCI apparatus's principles of operation.

FIG. 15A is a system block diagram which further describes the operation of the CGCI apparatus 100 by showing the procedure wherein the hand motion of the surgeon operating the user input devices 120 (such as the virtual tip 105) is captured and translated into a movement command. An optimization of the power versus force required to move the catheter tip 821 while using the amplifiers 131 through 138 to generate the necessary currents for the coils 112X through 118Z is provided. The coils produce a B field at the tip of catheter 821, responding to the force/torque generated at the tip 192 according to Maxwell's equations. The movement of the catheter tip 821 is tract by mapping apparatus 104 which detect, record, and display the position and orientation of the catheter 800 travel in real time and by the MOSFET sensor array 500, where the catheter tip position and orientation 194 information are displayed through a process of synchronization of the image 193 using fiduciary markers, thereby gating the position as well as the reflected force/torque generated by the actual distal end of the catheter tip 821. This process continuously repeats itself so as to respond to the operator's movement by the user input devices 120. The above procedure noted is clear and intuitive to those familiar with the art.

FIG. 15A further illustrates the process of guiding, controlling, and detecting the desired target and it is a possible rendition of the embodiments of this application:

i) the operator adjusts the physical position of the virtual catheter tip (VT) 105 to a desired position (DP) 172, ii) a change in the virtual tip 105 position is encoded in the controller 101, producing new position data from 193, received at the controller 101, iii) controller 101 generates commands sent to a servo system control module, iv) servo system control module controls the amplifiers 131 to 138 to optimize the position and orientation of the catheter magnetic tip 821, v) current is sent to the coils 112X to 118Z causing the position of the actual magnetic catheter tip 821 within the patient's body 390 to change, vi) the new position of the actual catheter tip (AP) is then sensed by system and the catheter position is superimposed on the image produced by fluoroscopy and/or other imaging modality 193, vii) feedback is provided to the servo system control apparatus and the monitoring system 101 of the operator interface.

Figure 16:
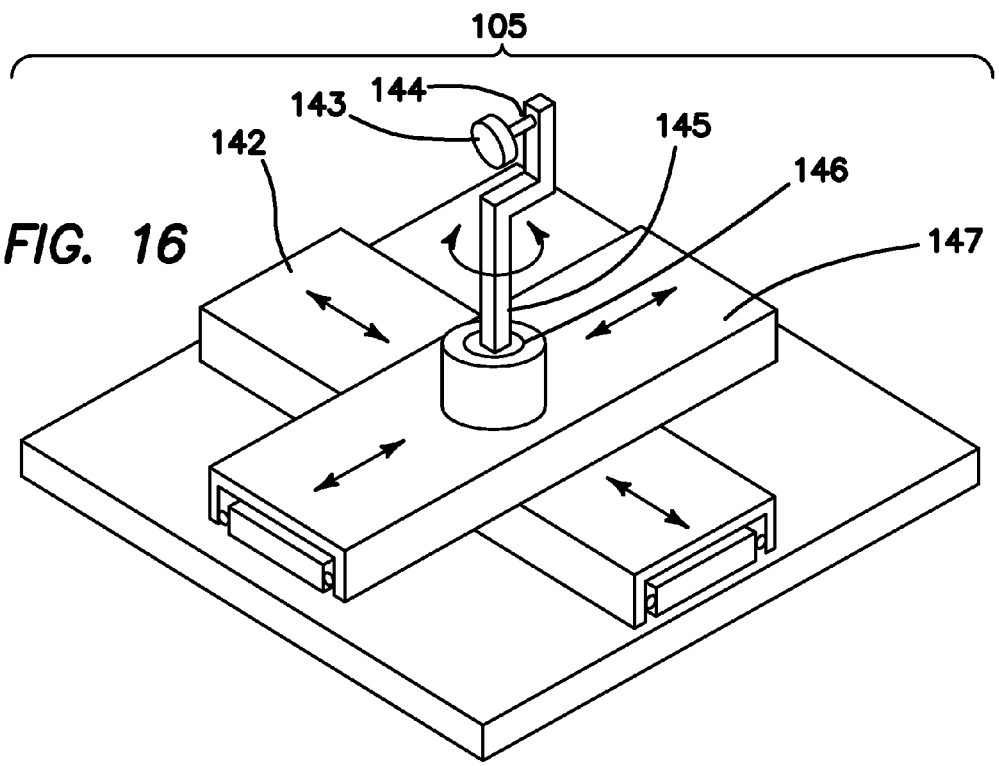
FIG. 16 is a perspective view showing one embodiment of the Virtual Tip user input device.

FIG. 16 is a perspective view showing one embodiment of the Virtual Tip user input device 105. The Virtual Tip 105 is a multi-axis joystick-type device that allows the surgeon to provide inputs to control the position, orientation, and rotation of the catheter tip 821.

In one embodiment, the Virtual Tip 105 includes an X input 142, a Y input 147, Z Input 145, and a phi rotation input 146 for controlling the position of the catheter tip 821. The Virtual Tip 105 further includes a tip rotation 143 and a tip elevation input 144. As described above, the surgeon manipulates the Virtual Tip 105 and the Virtual Tip 105 communicates the surgeon's movements to the controller 101. The controller 101 then generates currents in the coils to effect motion of actual catheter tip 821 to cause actual catheter tip 821 to follow the motions of the Virtual Tip 105. In one embodiment, the Virtual Tip 105 includes various motors and/or actuators (e.g., permanent magnet motors/actuators, stepper motors, linear motors, piezoelectric motors, linear actuators, etc.) to provide force feedback to the operator to provide tactile indications that the catheter tip 821 has encountered an obstruction of obstacle.

Figure 17:
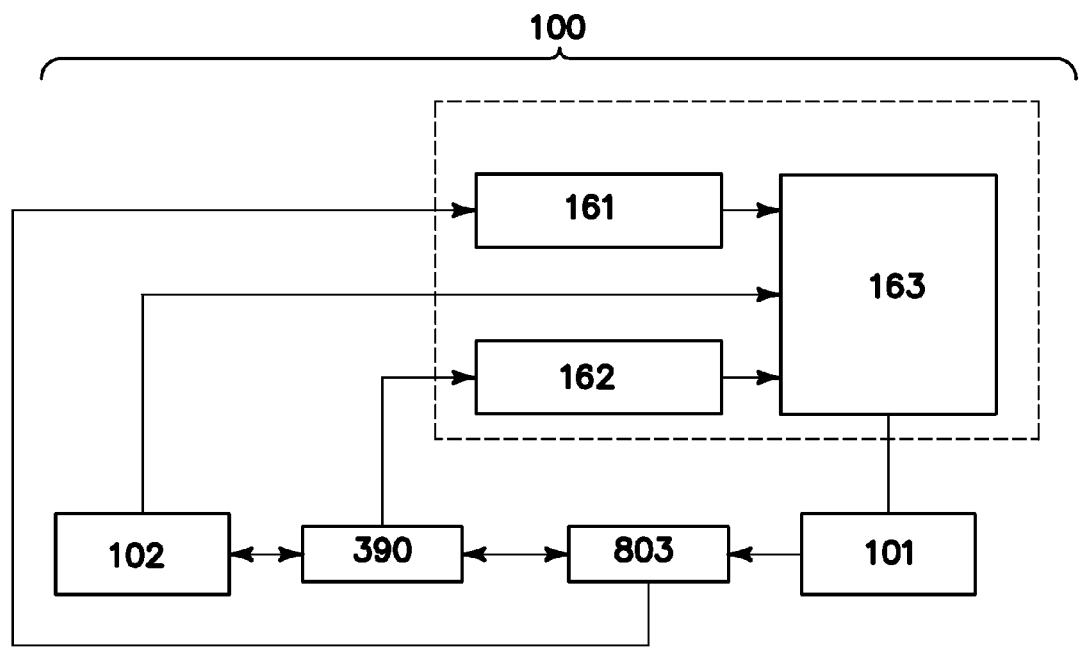
FIG. 17 is a block diagram of a CGCI unit which includes an imaging and synchronization unit

FIG. 17 is a block diagram of a CGCI unit 100 which includes an imaging and synchronization unit 104, a fiducial alignment system 162, and an operation console 163. In the CGCI Unit 100, the operator navigates a magnetically tipped catheter 800 within a patient 390 using a six-degree of freedom haptic joystick 105, while visualization of the progress of a virtual catheter tip 105 within the operation console's three dimensional virtual environment 163. The catheter tip position detection system 104 provides the current position of the catheter tip or actual position (AP) via the catheter detection unit 161, and the operator's position movement commands to move the catheter to a desired position (DP) via the operation console 163 are sent to the catheter tip position control system or the CGCI controller 101.

Use of a magnetic chamber with an adaptive regulator, while using a joystick/haptic device for operator control and method for detecting a magnetically tipped catheter is described in U.S. patent application Ser. No. 10/621,196. "Apparatus for Catheter, Guidance, Control, and Imaging" and is hereby incorporated by reference in its entirety. The technique and apparatus is further explained by U.S. patent application Ser. No. 11/331,781, "System and Method for Controlling Movement of a Surgical Tool" hereby incorporated by reference in its entirety. The magnetic apparatus for generating controlled movement in the patient's body is detailed by U.S. application Ser. No. 11/331,994, "Apparatus and Method for Generating a Magnetic Field" which is hereby incorporated by reference in its entirety. The method for controlling a surgical tool within the patient's body and the technique for such use is described by U.S. application Ser. No. 11/331,485, "System and Method for Magnetic Catheter tip," U.S. application Ser. No. 10/690,472, titled, "System and Method for Radar Assisted Catheter Guidance and Control," which are hereby incorporated by reference in their entirety. The magnetic chamber, its geometry and the formation of servo closed loop is detailed by U.S. application Ser. No. 11/140,475, "Apparatus and Method for Shaped Magnetic Field Control for Catheter, Guidance, Control and Imaging," which is hereby incorporated by reference in its entirety. The use of a magnetically tipped catheter while guided, controlled, and imaged by the apparatus noted above, is used in cardiology and specifically while mapping the electrical characteristics of the human heart to allow a controlled, accurate and efficient delivery of ablating RF energy. The use of the CGCI method and apparatus detailed above for use in electrophysiological mapping and ablation is noted by U.S. application Ser. No. 11/362,542, "Apparatus for Magnetically Deployable Catheter with MOSFET Sensors and Method for Mapping and Ablation," which is incorporated herein by reference in its entirety.

In one embodiment, the CGCI system 100 advances and controls the catheter tip 821 using a servo closed loop where the magnetic field in the chamber is controlled so as to generate magnetic force and force gradient to translate and rotate the catheter tip 821 within the magnetic chamber. This process of controlling the catheter-tip in magnetic chamber is dependent on the ability of the CGCI apparatus 100 to detect, calculate, and define accurately and in real-time the position and orientation of the catheter tip.

The system 100 allows a surgeon to move a catheter and other invasive tools within the patient's body while accounting for catheter position and orientation coordinates: while moving from AP to DP, and where the heart dynamics (systole, and diastole) are gated during movement of the catheter tip from AP to DP, the system 101 enable a definition of the rib cage displacement during respiratory cycle and is accounted for during the process of establishing the tip of the catheter tip, the system determined the coordinates of the virtual catheter tip 821 relative to the auxiliary imaging apparatus orientation to allow the orthogonal representation of the image capture with the specific anatomical feature of the patient's heart or the vascular tree, relative to the position and orientation of the virtual tip 105.

The system 100 allows a surgeon to move a catheter and other invasive tools while accounting for global transformation relative to the local transformation of any of the above mentioned variables while the catheter tip translation and/or rotation are fixed relative to each other.

The system 100 allows a surgeon to move a catheter and other invasive tools to inform a controller to form a servo closed loop modality for manipulating the catheter tip from AP to DP while accounting for the dynamic state of the independent variables noted above.

The operation console 163 includes the display screens, the haptic joystick 118 and a mouse. In the displays, the virtual catheter tip 105 is shown in relation to the user-selected three dimensional anatomical models 203. The view can be rotated and zoomed in and out for the proper perspective. Additional navigational reference icons show the global view of the patient and the local view of the anatomy of interest respectively.

The haptic joystick controller 118 is used to command the catheter tip 821. The system causes the catheter tip to follow movements of the virtual catheter tip 105. When the virtual tip is moved, a new desired position (and orientation), DP, is sent to the CGCI controller 101. The controller 101 controls the electromagnets of the system 100 to move the catheter tip 821 to the new position and orientation, DP. If the position and orientation, DP, cannot be obtained by the CGCI controller 101, the haptic joystick 118 forces the haptic stylus to provide tactile feedback to the operator using internal motors, informing the operator that the location is blocked (an obstacle is encountered). This allows the operator to sense the contours and blockages of the patient's anatomy 390 and prevent to the patient. In one embodiment, the amount of force provided as tactile feedback is computed as a function of the error between the desired position and the actual position. In one embodiment, the amount of force provided as tactile feedback is computed as a function of the error between the desired orientation and the actual orientation of the tip.

A procedure using the CGCI 100, such as ablation in the renal plexus, includes aligning the patient 390 on the operating table and traveling through the vascular tree, during which the MOSFET sensor array 500 sense the potential generated if any so as to arrive and locate the renal plexus on the right or the left of the kidneys. The procedure is guided and controlled by the use of the magnetic guidance system (CGCI) 100, the procedure and its embodiments are known to those familiar with the art.

Figure 17A:
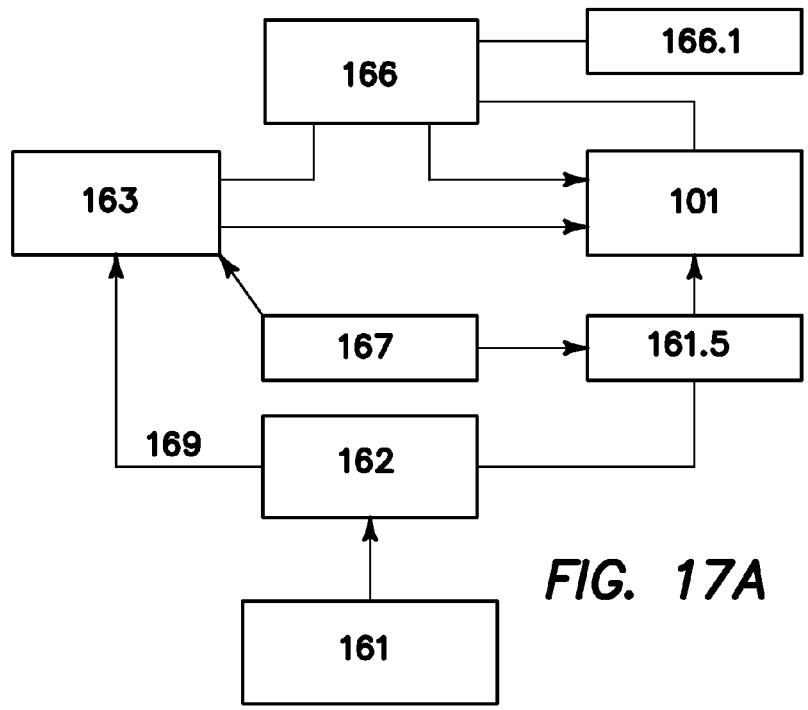
FIG. 17A is a system block diagram of the catheter guidance and control imaging (CGCI) system for position definition and guidance to locate and maintain tissue contact while acquiring data.

FIG. 17A is a system block diagram of the catheter guidance and control imaging (CGCI) system for position definition and guidance to locate and maintain tissue contact while acquiring data. The CGCI system for imaging and control of a catheter tip is described in U.S. patent application Ser. No. 11/697,690 "Method and Apparatus for Controlling Catheter Positioning and Orientation" and U.S. Pat. No. 7,280,863 "System and Method for Radar-Assisted Catheter Guidance and Control" and are hereby incorporated by reference in their entirety.

An actual position (AP) 169 and orientation of the distal end of the catheter is defined by external or internal subsystems of the CGCI system. Position detection can be globally referenced, or with respect to a six degree of freedom fiducial catheter, such as a custom coronary sinus catheter. Where the AP is defined with respect to the CGCI global coordinate system a fiducial alignment unit 162 maintains alignment with the patient's local coordinate system and converts between local and CGCI global coordinates. An operation console 163 defines the desired position (DP) 172 of the catheter tip. A CGCI controller 101 is given an initial tracking point on the tissue path and magnetically steers the catheter to point to a tracking point. The CGCI controller 101 sends the remaining positional error, the "closest proximity", between the AP 169 to an impedance seeking unit 166.

Contact confirmation with the surface of the vascular structure can be done by several methods, including, but not limited to, measuring surface conductivity. The impedance seeking unit 166 generates a tissue contact signal based on the degree of tissue contact, namely, a small DC direct current is injected at each location of tissue contact and the conduction is measured. If the tip of the catheter is in contact with the surface, the conduction is higher than if it was within the blood stream. The level of conductivity is recorded in the data set for future use. A minimum value can be set to limit data collection to good surface contact.

The impedance seeking unit 166 advances the catheter using a magnetic slide until continuous tissue contact is found by monitoring the tissue contact signal, or until the point is reached. If the desired point is reached before continuous contact is made, the CGCI controller 101 advances the point in a positive direction along the tissue path by a desired distance (e.g., 2 mm at a time), so as to maintain a predictable and repeatable approach to tissue contact. When full tissue contact is maintained, the impedance seeking unit 166 signals the CGCI controller 101 to stop all regulation and the catheter tip 821 is allowed to ride with the tissue surface under the current magnetic forces. If full tissue contact is made, but the location is too far from the tissue path, the impedance seeking unit 166 retracts the catheter 800 a distance (e.g., 5 mm) to allow the CGCI controller 101 to redirect the catheter tip 821.

Figure 18:
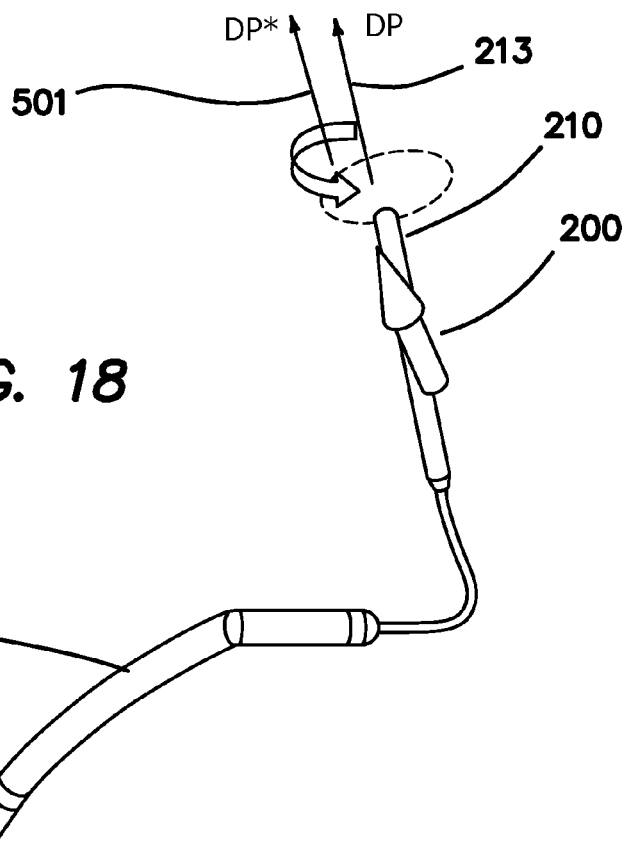
FIG. 18 is an illustration showing the relationship between the catheter's desired position (DP) and its modified desired position (DP*).

FIG. 18 is an illustration showing the relationship between the catheter's desired position (DP) and its modified desired position (DP*). The catheter 800 emerges from within the sheath 814 and is magnetically manipulated through the use of magnetic forces and torques. The magnetic indicator 173 indicates the actual direction of the magnetic field. The desired position, DP 172, is represented here as being identical to the actual location and direction of the catheter tip (AP), which is representative of a catheter that has been moved to its closed loop rest position. The modified desired position, DP* 171 is a vector in the same direction as DP, but orbits at a relatively fixed distance. The catheter with its MOSFET sensor array 500 provides for continuous monitoring of bioelectric potential as the operator advance the catheter through the vascular tree, once an appropriate signal is identified the operator can fix the actual position (AP*) and perform the necessary diagnostic and or therapeutic procedure.

The desired position, DP 172, is defined on or near the surface of the target (e.g. renal plexus). The path 325 can be selectively defined as the surface normal of the geometric model at the point DP 172. The tracking point TP is the closed-loop regulator target point sent to the CGCI controller 101, a catheter 800 is inserted e.g. into the left renal artery 325. The magnetic tip 821 is guided to the tracking point by the CGCI controller 101. Once the catheter is set at the DP 172 the operator can elect to fix the catheter 800 at that site by the use of the CGCI regulator/controller 501 and proceed with the therapeutic stage of the treatment, by applying energy, such as it is known in the art remodeling of electrical activity and generally defined as neuromodulation. This procedure is achieved by employing RF energy to transfer energy to the required site and by setting the RF generator 152 to deliver 8-10 watts of RF energy for 120 seconds. This process is repeated for each of the relevant points identified by the electro anatomical map 203 produced during the initial diagnostic phase of the operation and as described by the ensuing figures and its accompanying descriptions.

Figure 18A:
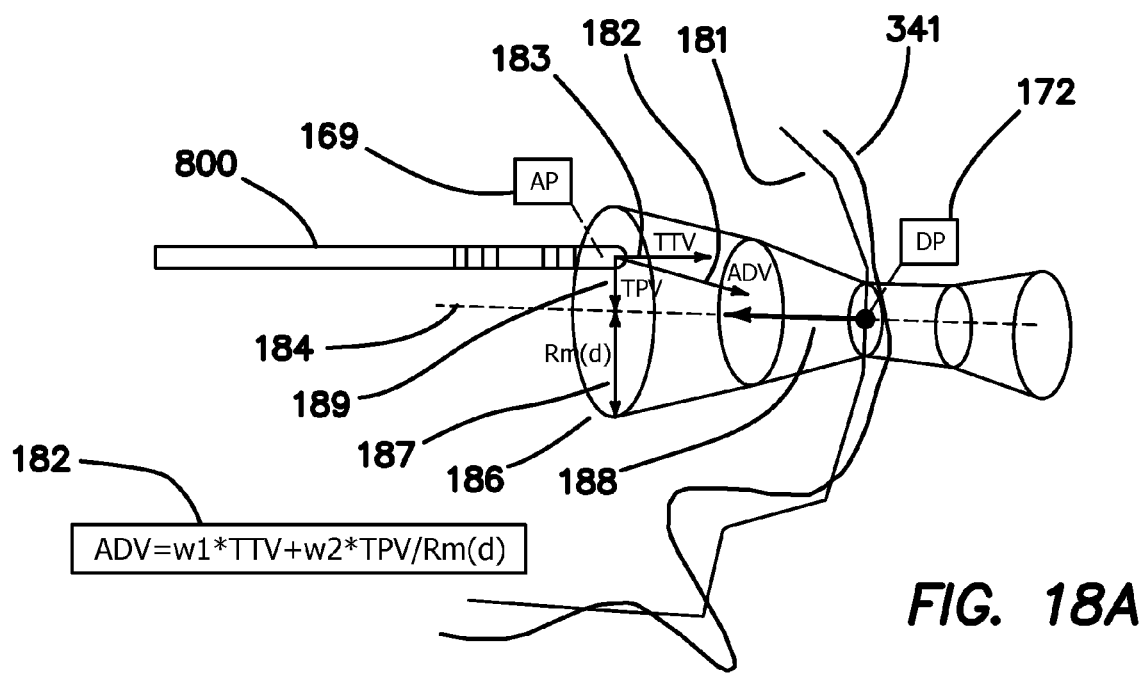
FIG. 18A is a schematic diagram of a catheter in relationship to the virtual and real tissue surface with associated control vector information.

FIG. 18A is a schematic diagram of a catheter 800 in relationship to the virtual and real tissue surface with associated control vector information. The catheter with its MOSFET sensor array 500 is guided by the Guidance Control and Imaging System 100 from its current Actual Position and Orientation, AP 169, through the Desired Position and Orientation, DP 172. DP 172 is on the surface of the CGCI's Geometric Map 181, and not on the actual Patient artery Surface 341, so the catheter is guided on a path to the surface, called the CISD Tissue Contact Targeting Manifold 186 until it makes continuous contact with the tissue surface, as indicated by the tissue contact detector.

If the continuous contact found signal is located outside of the CISD Tissue Contact Targeting Manifold 186, the Catheter Impedance-Seeking Logic employing the MOSFET sensor array 500 is used to identify and report the surface contact signal while the apparatus 100 corrects for any translation or rotation of the catheter from its surface contact by employing the closed loop of the CGCI system 101 so as to achieve the DP 172 by informing the CGCI Controller/regulator 101 so as to adjust the catheter to its new path i.e. its tissue surface contact. The CISD Tissue Contact Targeting Manifold 186 is a set of radius values for the targeting manifold at each distance from the desired position, DP 172. The accuracy of contact surface tangent point is adjured based on operator demand and is defined as concentric radius from the vector normal of surface.

FIG. 19 is a perspective view representing a renal artery signal map 203 containing both low level signal areas 201 and high level signal areas 202 as well as a visualization of the catheter 800.

Figure 19A:
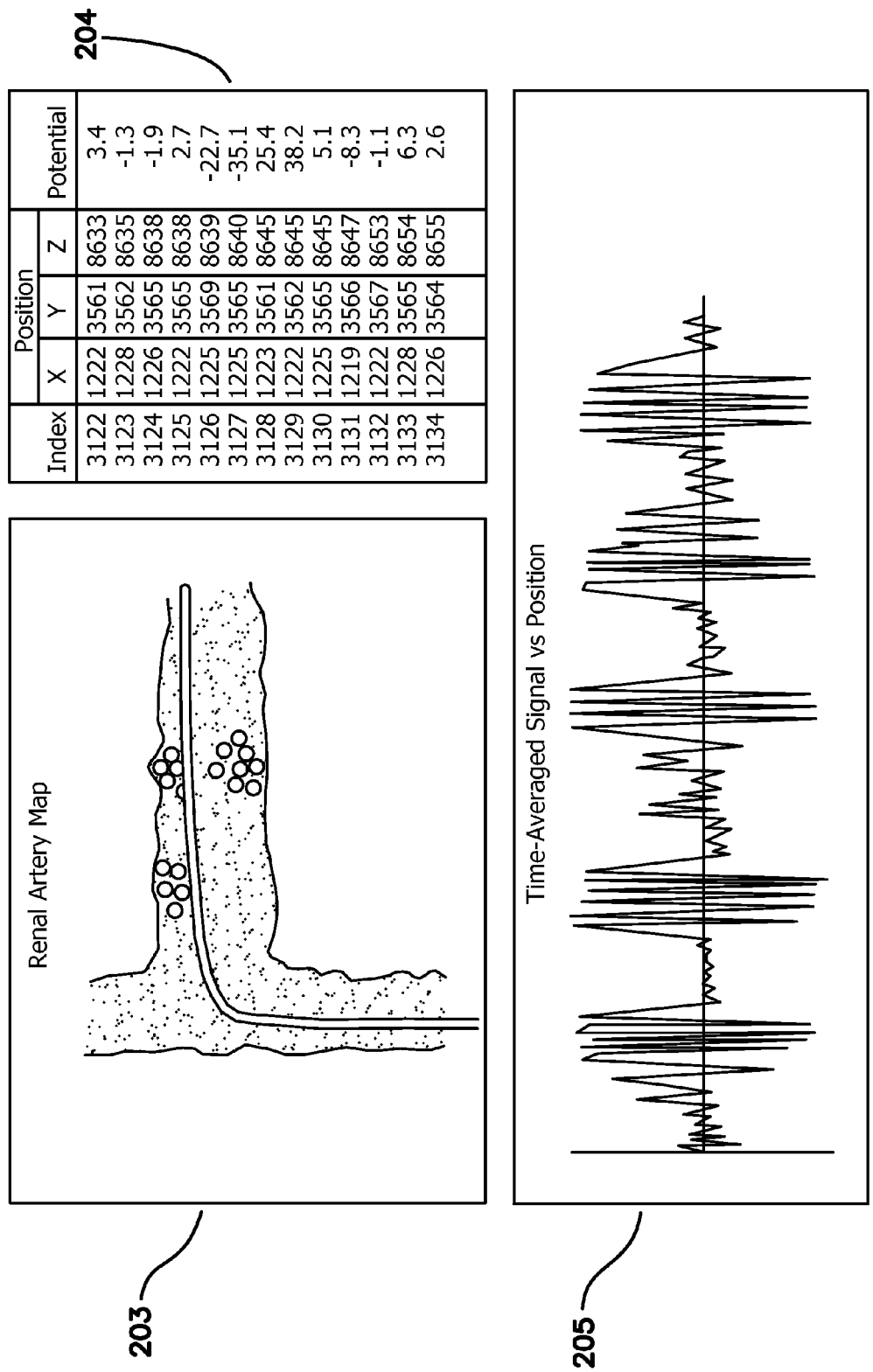
FIG. 19A illustrates a catheter with its MOSFET sensor array guided to the target site by the CGCI System.

FIG. 19A illustrates catheter 800 with its MOSFET sensor array 500 as its guided to the target site by the CGCI system 100. The catheter 800 is first performing the electro anatomical mapping procedure where the arterial structure is identified and the bioelectric potentials 205 are recorded. The data set 204 is emulated so as to form a graphic representation of the anatomy 203 with its associated dimensional coordinates, the bioelectrical potential values measured by the sensors 205 are then correlated, so as to form a data set comprising of an order set 204 (X, Y, Z, <IMPΩ>T°), and where the X, Y, Z is the coordinates of the specific sensor 520 from the array 500 and, <IMPΩ>, is the impedance value of the site and where T°, is the temperature of the site. The operator or physician use the generated map produced by the MOSFET sensor array 500 and its graphical display 203 to proceed with the therapeutic phase of the procedure.

FIG. 19A further describes graphically the renal sympathetic efferent and afferent nerves, which schematically represented adjacent to the wall of the renal artery 325. As described previously, this activity contributes to the pathogenesis of hypertension. Because the causative factors of hypertension change over time, guidance and control of mapping catheter of the type proposed by the invention of both efferent and afferent nerves should affect the outcome of the treatment due to the remodeling and or attenuation of the renal plexus activity and its contribution to hypertension. The importance of proper mapping of the axonal terminus of the nerve laying in and within the renal nerves in patients with hypertension can now be defined with the novel development of percutaneous minimally invasive mapping and with the use of RF energy to perform neuromodulation so as to achieve renal denervation from within the renal artery. The use of the novel transistorized MOSFET sensor array 500, enables the formation of accurate and spatial-temporal definition of the electro-anatomical characteristics of the renal artery nerve endings. The embodiments of the apparatus are directly related to the nature of MOSFET device 513 due to its ability to collect electrical data in the order of 5-10 micro-volts. This class of value of electrical activity achieved by renal plexus is as shown by studies thus far indicating that catheter-based renal denervation in patients with refractory hypertension lowers systolic blood pressure 27 mm Hg by 12 months with estimated glomerular filtration rate remaining stable. An attenuation of hypertension of this magnitude by catheter-based renal sympathetic denervation in combination with pharmacologic therapy is likely to be valuable in decreasing the risks of stroke, left ventricular hypertrophy, heart failure, and chronic renal failure.

During the renal denervation procedure at the target site, the catheter 800 is fixated at the target site, moving from actual position (AP) 169 to desired position (DP) 172 is magnetically manipulated so as to achieve contact and collect the bioelectrical potential measurement repeatedly as part of a mapping procedure. Contact between the MOSFET 513 and HEMT 555 sensors on the catheter tip 821 allow measurement of a potential change on a dynamical basis, spatial as well as temporal variations. This potential change is calibrated for the patient and thresholds are determined for the various states of interest (e.g. catheter contact with circulatory system membranes, catheter position within the blood pool, general circulatorylarterial potential, and circulatory/arterial potential membrane potential at the renal artery). Further shown is an example of data collected by the invention during a mapping procedure. The catheter's position and orientation are both crucial for accurate mapping and localization of treatment. As such, the table shows assignment of a number to the data point, its location on the mapping system in x, y, and z coordinates, the time of the collection of the data point, and the potential/resistance measured in Ω or milliohms.

Figure 20:
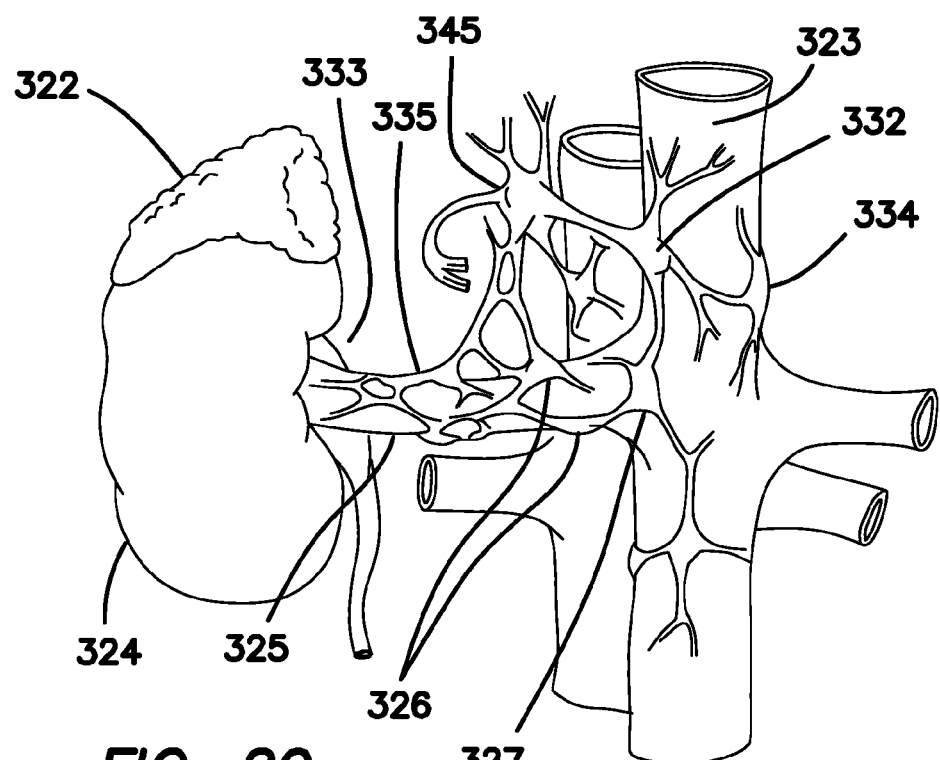
FIG. 20 is an illustration of a right kidney and renal vasculature.

FIG. 20 is an illustration of a right kidney 324 and renal vasculature including a renal artery 325 branching laterally from the abdominal aorta 323. Reference is made herein to both right and left kidneys and associated renal vasculature and nervous system structures, all of which are contemplated within the context of embodiments of the present invention.

In another embodiment of the invention we use the example of ganglionic plexus as an analogue signal so as to demonstrate the use of the catheter sensing capabilities and to enable a consistent and measurable application of contact force within the anatomical structure and by further providing a safe and optimal contact force between the catheter distal end and the arterial structure. This measure is essential for the fidelity of the measurement of the site, as nerve activity is subject to the physical inverse law and hence the operator needs to know that the biopotential of the site in question is a measure of a bioelectric potential of near field as oppose to far fields carried by the blood flow transfusing through the renal artery.

The theory which underlies the use of a matrix array of transistorized pads as noted is due to the inherent bioelectric potential behavior and the ability of the novel use of such technology to mimic the complexity as well the dynamics of such activity. Neurons and muscle cells create ion currents through their membrane when excited, causing a change in voltage both inside and outside the cell. When recording on the MOSFET sensor array 500, the activity of the tissue substrate transducer the change in voltage from the environment carried by ion into currents carried by electrons. When stimulating, the MOSFET sensor array 500 transduces the electronic currents into ionic currents through the media. This triggers the voltage-gated ion channels on the membranes of the excitable cells, causing the cell to depolarize and trigger an action potential if it is a neuron. The size and shape of a recorded signal depends upon several factors: the nature of the medium in which the cell or cells are located (e.g. the medium's electrical activity, capacitance, and homogeneity); the nature of contact between the cells and the MOSFET sensor array 500 (e.g. area of contact and tightness); the nature of the electrode itself (e.g. its geometry, impedance, and noise); the analog signal processing (e.g. the system's gain, bandwidth, and behavior outside of cutoff frequencies); and the data sampling properties (e.g. sample rate and the nature of the digital signal processing algorithm). For the recording of a single cell that partially covers a planar electrode, the voltage at the contact pad is approximately equal to the voltage of the overlapping region of the cell and electrode multiplied by the ratio the surface area of the overlapping region to the area of the entire electrode, or:

$$V_{pad} = V_{overlap} \times (A_{overlap}/A_{electrode})$$

assuming the area around an electrode is well insulated and has a very small capacitance associated with it. The equation above, however, relies on modeling the electrode, cells, and their surroundings as an equivalent circuit diagram. An MEA can be used to perform electrophysiological studies on tissue it can be seen that the voltage amplitude on the MOSFET sensor pad is inversely related to the distance from which a cell depolarizes. Allowing the placement of multiple electrodes at once rather than individually. With respect to MOSFET sensor array 500 however, the major advantage over electrode technology is the high spatial resolution and where MOSFET sensor array 500 allow signals to be obtained from individual neurons enabling information such as position or velocity FIG. 20A is an illustration of the right renal architecture depicting a catheter 800 fitted with a MOSFET sensor array 500 being magnetically guided.

In the ensuing paragraphs we highlight the fact that cellular etiology provides us with electrophysiological indications, and by the consistent application of the methods and embodiments of this invention a robust predictive outcome is enabled so as to dramatically reduce the incidence of morbidity associated with the use of mechanically translating and rotating catheter in the renal artery while using a catheter to perform a neuromodulation by applying energy to block or redirect peripheral nerve impulse.

Figure 20A:
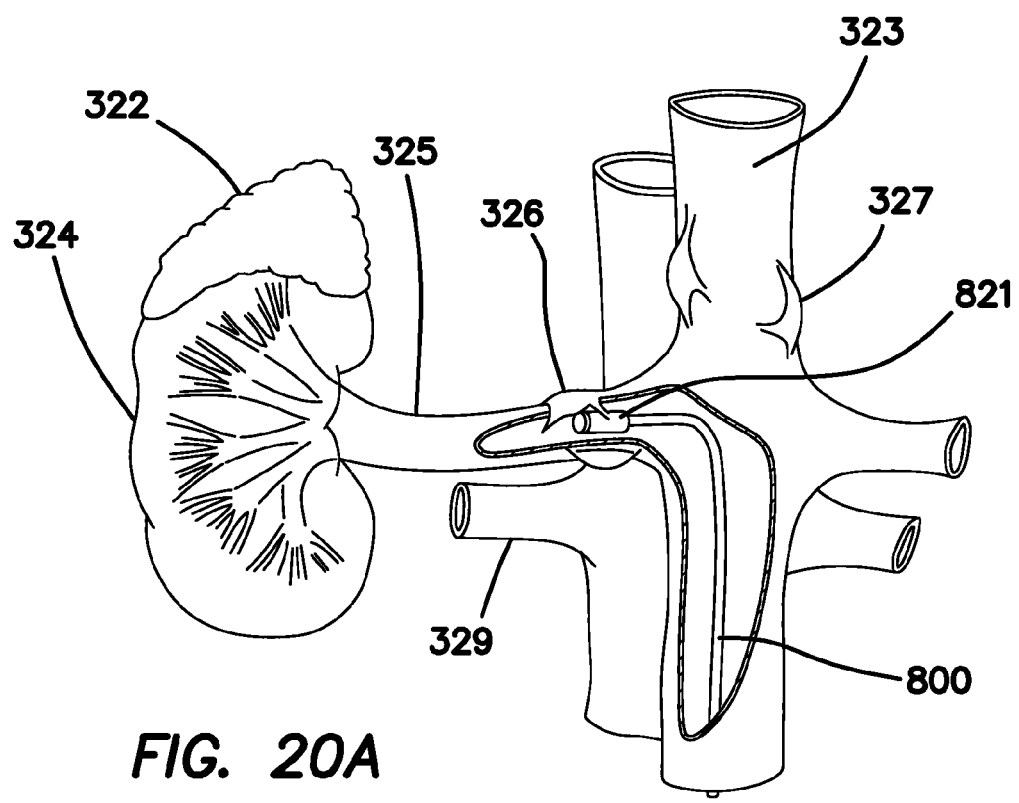
FIG. 20A is an illustration of the right renal architecture depicting a catheter fitted with a MOSFET sensor array being magnetically guided.

FIG. 20A further illustrates the incorporation of apparatus for facilitating remote magnetically guided delivery of a MOSFET mapping and ablation catheter 800 to innervated tissue and ganglia that contribute to renal sympathetic nerve activity in accordance with embodiments of the invention.

In another embodiment, the RF ablation catheter 800 is used cooperatively with an imaging system such as known the art for example, an impedance mapping apparatus by such as the St. Jude Medical ENSITE or magnetic localization system, as exemplified as CARTO by J&J BioSense Webster, which enables a catheter to locate target within anatomical context and by provide geometrical coordinates of specific anatomical destination e.g. renal nerves. This process of defining an anatomical site such as a renal plexus ganglia so as to effect a change of nerve signal or generally enhance a procedure we generally classify as neuromodulation or a renal denervation. Specifically, where a surgical and/or electrical intervention deactivates the ability of the sympathetic nerve or its ganglia to influence the activity of the sympathetic autonomic nervous system so as to achieve a clinical outcome.

The desired clinical outcome is best accomplished by employing the MOSFET sensor array 500 within the catheter 800 in a stable position whereby the MOSFET sensor array 500 registers a high bioelectrical potential and when the impedance sensor 826 indicates a contact with a specific impedance value, the catheter 800 is than activated to deliver energy with a set value of 8-10 watts of RF energy. FIG. 20A describes a MOSFET sensor array 500 and its irrigated RF ablation catheter 800 configured for maintaining the catheter in a stable position and orientation as detailed by the use of the embodiments noted by patent referenced above and by delivering the necessary energy to denervate the active site. The system and its methods provide the operator with the means to effect the modulation of nerve activity and achieve the desired goal of neuro-attenuation.

The process described is governed by the use of the apparatus' ability to first provide an indication of position and orientation of the catheter 800 with constant impedance value indicating surface contact with the vessel lumen so as to be enable to deliver the necessary RF energy through the adventitia and where the ablating energy is transmitted to the renal nerve and the gangilia in an optimal and safe mode.

The deployment of the MOSFET sensor array 500 with its irrigation catheter, is further integrated with a magnetic element embedded as shown by FIGS. 10 and 11 to enable the use of external magnetic fields to rotate and translate the catheter movements to its desired destination of the specific arterial branch such as the renal artery plexus and place the catheter in its desired position and by further holding the catheter 800 in its proper position and while orienting the distal tip of the catheter so as to enable a stable, consistent and reliable localization of the catheter 800. This functionality of guiding and controlling the catheter to its desired location is best described in FIGS. 18 and 18A. The MOSFET sensor array 500 is employed alternatively as a Field Effect Transistor for locally measuring the bioelectric potential 202 which is generated by the nerve endings of the sympathetic plexus, while the apparatus switch the MOSFET sensor array 500 to provide a reliable measure of the vessel contact impedance. The impedance of the vessel inner diameter is typically at a value of 75 to 90 ohms, while a typical measure of the catheter with its MOSFET sensor array in direct contact with the vessel 325 is yielding a value of more than 120 ohms.

According to one embodiment, the irrigated ablation catheter 800 with its integrated MOSFET sensor array 500 is delivered to a location within a patient's renal artery 325. The MOSFET sensor array catheter 800 preferably includes a mapping device, such as EnSit Navix of St. Jude Medical or other mapping device such as CARTO produced by J&J BioSense Webster.

The mapping device 102 identifying the position and orientation of the MOSFET sensor array catheter 800, enables the operator (the physician) to guide the catheter 800 using the joystick 118 so as to properly positioned in a proximate area to the renal artery 325, MOSFET sensor array catheter 800 is advanced into the renal vein 329, typically accessed via the inferior vena cava. The MOSFET sensor array catheter 800 preferably includes a steering mechanism comprising of the magnetically guided system 100 which enables suitable steering of the catheter to its desired destination, by pushing, pulling, rotating, and advancing the catheter 800 in any direction along the X, Y, and Z axis is enabled by the use of the permanent magnet 823 encapsulated in the tip as shown in FIG. 10 which further carries the preferred embodiment of MOSFET sensor array catheter 800.

The MOSFET sensor array catheter 800 includes a transistorized High Electron Mobility voltage sensitive device 555 as described above. Using the catheter 800 positioned adjacent a renal vein wall location, the MOSFET sensor array 500 with its energy delivery capability is delivered to isolate the conduction path in the renal vein. With aid from the MOSFET catheter 800, the catheter 800 is advanced by magnetic manipulation through the arterial tree and navigated around the exterior of the renal artery 325 to a location adjacent a target nerve or ganglion, such as a renal ganglion 326.

RF energy is applied using the irrigated catheter 800 to ablate the target tissue in a manner previously described, so that all renal sympathetic nerve activity associated with nerve fibers included within the target tissue is permanently terminated. The MOSFET mapping and its delivery of RF energy combined with its magnetic navigational capabilities as described above can be navigated to any electro-anatomical location of the renal artery or abdominal aorta 323, such as a location of the renal artery 325 that includes a renal nerve 335, the aortio-corenal ganglion 327, the superior mesenteric ganglion 334, or the celiac ganglia 332 or plexus 345.

The MOSFET sensor array catheter 800 is manipulated, pushed, pulled, rotated, and translated through to an appropriate intravascular location by the aid of magnetic navigation so as to position the MOSFET sensor array 500 with its irrigated ablation catheter 800, so as to locate it within its optimal location within the renal vein 329.

In accordance with various embodiments described herein, one or more physiologic parameters can be monitored during the ablation procedure to determine the effect of the ablation on the patient's renal sympathetic nerve activity. For example, a matrix of MOSFET sensors 520 is situated in contact with the inner or outer wall of the renal artery 325 near opposing sides of the renal artery 325 by the use of the method of CISD and the continuous contact of the catheter with the anatomical surface 341. The MOSFET array 500 may be configured to measure the nerve impulses transmitted along renal nerve fibers in a continuous node, enabling a measured delivery of energy so as to provide the operator with controlled and safe delivery of the RF energy without the adverse effects known in the art as stenosis (artery) as well as thrombi generation which might deteriorate the kidney function. By way of further example, one or more physiological parameters that are sensitive to changes in renal sympathetic nerve activity may be monitored, and the efficacy of the ablation procedure may be determined based on measured changes in the physiological parameter(s).

Many alterations and modifications may be made by those having ordinary skill in the art without departing from the spirit and scope of the embodiments. Therefore, it must be understood that the illustrated embodiment has been set forth only for the purposes of example and that it should not be taken as limiting the embodiments as defined by the following embodiments and its various embodiments.

Therefore, it must be understood that the illustrated embodiment has been set forth only for the purposes of example and that it should not be taken as limiting the embodiments as defined by the following claims. For example, notwithstanding the fact that the elements of a claim are set forth below in a certain combination, it must be expressly understood that the embodiments includes other combinations of fewer, more or different elements, which are disclosed in above even when not initially claimed in such combinations. A teaching that two elements are combined in a claimed combination is further to be understood as also allowing for a claimed combination in which the two elements are not combined with each other, but may be used alone or combined in other combinations. The excision of any disclosed element of the embodiments is explicitly contemplated as within the scope of the embodiments.

The words used in this specification to describe the various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the embodiments.

We claim:

1. A system for detecting or mapping and ablating a renal nerve ending within a renal artery comprising:
   a catheter having a body and a distal end for insertion into the renal artery;
   an ablation tip coupled at the distal end of the catheter;
   a plurality of annular ablation electrodes disposed circumferentially around the body of the catheter;
   a temperature sensor disposed in the distal end of the catheter within the ablation tip;
   a magnet disposed in the distal end of the catheter within the ablation tip;
   a plurality of articulated magnetic beads disposed in the body of the catheter;
   a sensor array including a plurality of MOSFET modules coupled to the surface of the body of the catheter, wherein the sensor array is arranged and configured to sense a local bioelectric potential of the renal nerve ending using the plurality of MOSFET modules;
   a computer accessible memory that stores the measurements of the bioelectric potential of the renal nerve ending obtained by the at least one sensor array;
   a computer processor communicated with the memory and the sensor array, the computer processor correlating the measurements of the bioelectric potential of the renal nerve ending sensed by the sensor array with a location of the distal end of the catheter to detect or create a map of the renal nerve ending; and
   a plurality of electromagnetic coils configured to create a controllable magnetic field source that is configured to guide and control the catheter through the renal artery by magnetic interaction with both the magnet disposed in the distal end of the catheter within the ablation tip and with the plurality of articulated magnetic beads disposed in the body of the catheter to the renal nerve ending as recorded on the map to controllably position the ablation tip at the mapped renal nerve ending.

2. The system of claim 1 where each MOSFET module of the sensor array comprises a capacitor, a MOSFET transistor, and a sensor pad coupled via the capacitor to the MOSFET transistor so that coupling of the sensor pad with different dielectric media or biopoentials varies the capacitive load on the capacitor and the bias on the MOSFET transistor so that the biased MOSFET transistor functions as a variable resistor with a local ground having an impedance of a few $k\Omega$ to allow a local biopotential in microvolt magnitudes to be detected with fidelity.

3. The system of claim 2 wherein each one of the MOSFET modules of the plurality of MOSFET modules further comprises a pressure sensor and a MOSFET temperature sensor to provide realistic conditions for defining the sensed dielectric media as it varies from patient to patient and while the patient is under different medications.

4. The system of claim 2 where the sensor array includes a calibration element having a MOSFET gate with a fixed value at a nominal potential and where a difference between the output of the MOSFET transistor and the output of the calibration element provides a MOSFET module output, so that the calibration element determines the ability of the MOSFET module to self-calibrate relative to variability of the biological media due to medication, anesthesia, and fluid intake and to avoid noise associated with variability of the situs of detection.

5. The system of claim 2 where the plurality of MOSFET modules comprising the sensor array are disposed within the sensor array in an asymmetrical pattern.

6. The system of claim 1 where the MOSFET module comprises a high-electron mobility transistor (HEMT) which is sensitive to a dielectric variation.

7. The system of claim 1 where the plurality of articulated magnetic beads are coupled to a longitudinal surface of the catheter.

8. The system of claim 1 further comprising a calibration element and to an analog-to-digital converter, where the sensor array is coupled to the calibration element and to the analog-to-digital converter.

9. The system of claim 1 where the plurality of MOSFET modules in the sensor array are coupled in a multiplexed matrix to provide a selected local high-fidelity signal.

10. A method for mapping and ablating a renal nerve ending within a renal artery comprising:
    inserting a catheter including an ablation tip disposed on its distal end into the renal artery;
    sensing a local bioelectric potential with a sensor array including a plurality of MOSFET modules disposed on the catheter;
    correlating the sensed local bioelectric potential with a location of the distal end of the catheter to create a map of a site of ganglionic nerve impulse activity within the renal artery;
    manipulating a magnetic field source to guide and control that catheter through the renal artery;
    guiding the catheter to a site of ganglionic nerve impulse activity within the renal artery as identified by the map; and
    ablating the renal nerve ending at the site of ganglionic nerve activity within the renal artery.

11. The method of claim 10 where sensing the local bioelectric potential with the sensor array disposed on the catheter comprises measuring the impedance between the surface of the renal artery and at least one of a plurality of MOSFET modules comprising the sensor array.

12. The method of claim 11 further comprising converting the measured impedance signal between the surface of the renal artery and at least one of the MOSFET modules of the plurality of MOSFET modules into a digital signal and transmitting it to a microcontroller.

13. The method of claim 10 where sensing the local bioelectric potential with the sensor array disposed on the catheter comprises differentiating between bioelectric signals emanating from near fields and those emanating from far fields.

14. The method of claim 10 where ablating the renal nerve ending at the site of ganglionic nerve activity within the renal artery comprises applying RF energy to the site of ganglionic nerve activity and denerving the nerve ending within the renal artery.

15. The method of claim 10 where manipulating the magnetic field source to guide and control the catheter in the renal artery comprises moving the catheter from an actual position to a desired position in the renal artery by changing the direction and magnitude of a magnetic field generated by the magnetic field source.

16. The method of claim 15 further comprising inputting movement control of the catheter by use of a six-degree-of-freedom haptic joystick.

17. The method of claim 10 where sensing the local bioelectric potential with the sensor array disposed on the catheter comprises using impedance variation of at least one MOSFET module in the sensor array to sense the proximity of a transistor pad to tissue by comparison of impedance to a predetermined threshold to indicate "contact" or "no contact".

18. A system for mapping and ablating a nerve ending within a vascular system comprising:
   a catheter having a body and a distal end for insertion into the vascular system;
   an ablation tip coupled to the distal end of the catheter;
   a magnet coupled to the body of the catheter;
   a sensor array including a plurality of MOSFET modules coupled to the body of the catheter, wherein the sensor array is arranged and configured to sense a local bioelectric potential of the nerve ending using the plurality of MOSFET modules;
   a computer accessible memory that stores the measurements of the bioelectric potential of the nerve ending obtained by the at least one sensor array;
   a computer processor communicated with the memory and the sensor array, the computer processor correlating the measurements of the bioelectric potential of the nerve ending sensed by the sensor array with a location of the distal end of the catheter to detect or create a map of the nerve ending; and
   a controllable magnetic field source configured to guide and control the catheter through the vascular system by magnetic interaction with the magnet to the nerve ending as recorded on the map to controllably position the ablation tip at the mapped nerve ending.

19. The apparatus of claim 18 where the plurality of MOSFET modules are asymmetrically disposed about or in the sensor manifold.

20. A method for mapping and ablating a nerve ending within a vascular system comprising:
   inserting a catheter including an ablation tip disposed on its distal end into the vascular system;
   sensing a local bioelectric potential of the nerve ending with a sensor array including a plurality of MOSFET modules disposed on the catheter;
   correlating the sensed local bioelectric potential with a location of the distal end of the catheter to detect or create a real-time recorded map of the nerve ending within the vascular system;
   manipulating a magnetic field source to guide and control the ablation tip of the catheter through the vascular system to the site of the nerve ending as identified by the real-time recorded map; ablating the nerve ending within the vascular system; and
   sensing for a local bioelectric potential of the ablated nerve ending with the sensor array including a plurality of MOSFET modules to confirm elimination of nerve activity at the site of the nerve ending.

* * * * *